(12) United States Patent
Schüler et al.

(10) Patent No.: US 11,844,904 B2
(45) Date of Patent: Dec. 19, 2023

(54) TAKING UP SYSTEM AND PROCESS WITH A FILTER UNIT FOR THE RECEIVING OF GAS FROM A MEDICAL APPARATUS

(71) Applicant: Drägerwerk AG & Co. KGaA, Lübeck (DE)

(72) Inventors: Hans Ulrich Schüler, Lübeck (DE); Ralf Heesch, Lübeck (DE); Robert Schmid, Lübeck (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 307 days.

(21) Appl. No.: 17/344,724

(22) Filed: Jun. 10, 2021

(65) Prior Publication Data

US 2021/0386955 A1 Dec. 16, 2021

(30) Foreign Application Priority Data

Jun. 12, 2020 (DE) ..................... 10 2020 115 602.2

(51) Int. Cl.
*A61M 16/10* (2006.01)
*B01D 46/00* (2022.01)
(Continued)

(52) U.S. Cl.
CPC ........ *A61M 16/105* (2013.01); *A61M 16/104* (2013.01); *B01D 46/0005* (2013.01);
(Continued)

(58) Field of Classification Search
None
See application file for complete search history.

(56) References Cited

U.S. PATENT DOCUMENTS 8,356,596 B2 1/2013 Brandt et al.
8,997,741 B2 4/2015 Heesch et al.
(Continued)

FOREIGN PATENT DOCUMENTS

CN 101896216 A 11/2010
DE 4340764 A1 * 12/1994 ............ A61M 16/08
(Continued)

OTHER PUBLICATIONS

DE4340764A1_ENG (Espacenet machine translation of Schwarzmann) (Year: 1994).*

(Continued)

*Primary Examiner* — Gabriel E Gitman
(74) *Attorney, Agent, or Firm* — McGlew and Tuttle, P.C.

(57) ABSTRACT

An taking up/receiving system (100) and a process for taking up/receiving of gas from a medical apparatus (1) are provided. The taking up/receiving system includes a feed line (6), a discharge line (8), a filter unit (4) with a filter and at least one buffer storage device. The feed line establishes a fluid connection between the medical apparatus and the filter unit. The discharge line establishes a fluid connection between the filter unit and a fluid taking up/receiving unit (7). The gas is discharged from the medical apparatus and is passed through the feed line to the filter unit and from there through the discharge line to the fluid taking up/receiving unit. The filter filters at least one gas component out of the gas that is passed through the filter unit. The one or more buffer storage device absorbs and again discharges gas from time to time.

35 Claims, 28 Drawing Sheets

(51) Int. Cl.
  *A61M 16/20* (2006.01)
  *B01D 53/04* (2006.01)
  *B01D 46/44* (2006.01)

(52) U.S. Cl.
  CPC ..... *B01D 46/0036* (2013.01); *B01D 46/0086* (2013.01); *B01D 46/0087* (2013.01); *B01D 46/0097* (2013.01); *B01D 46/442* (2013.01); *B01D 46/444* (2013.01); *B01D 53/0407* (2013.01); *A61M 16/209* (2014.02); *B01D 2259/4533* (2013.01); *B01D 2279/35* (2013.01)

(56) References Cited

U.S. PATENT DOCUMENTS

| | | | | |
|---|---|---|---|---|
| 9,314,766 | B2 * | 4/2016 | Filipovic | B01J 20/3483 |
| 9,770,569 | B2 | 9/2017 | Heesch | |
| 10,173,157 | B2 * | 1/2019 | Dong | B01D 35/30 |
| 2001/0022181 | A1 * | 9/2001 | Masson | A61M 16/22 |
| | | | | 128/205.12 |
| 2001/0025640 | A1 | 10/2001 | Pessala | |
| 2005/0247316 | A1 * | 11/2005 | Orr | A61M 16/009 |
| | | | | 128/205.12 |
| 2011/0048417 | A1 * | 3/2011 | Ahlmen | A61M 16/009 |
| | | | | 128/205.27 |
| 2014/0102450 | A1 | 4/2014 | Broborg et al. | |
| 2015/0144135 | A1 * | 5/2015 | Heinonen | A61M 16/22 |
| | | | | 128/203.14 |
| 2015/0336042 | A1 * | 11/2015 | Welke | B01D 53/00 |
| | | | | 55/482 |
| 2016/0001102 | A1 * | 1/2016 | Huh | A62B 7/10 |
| | | | | 128/206.17 |
| 2017/0056610 | A1 | 3/2017 | Hunt et al. | |
| 2018/0110947 | A1 | 4/2018 | Brown | |

FOREIGN PATENT DOCUMENTS

| | | | | |
|---|---|---|---|---|
| DE | 196 05 695 | A1 | 8/1997 | |
| DE | 19605695 | A1 * | 8/1997 | ......... A61M 16/009 |
| DE | 10 2006 008320 | A1 | 8/2007 | |
| DE | 102006027052 | B3 | 8/2007 | |
| DE | 10 2006 053216 | A1 | 5/2008 | |
| DE | 102008057180 | B3 | 4/2010 | |
| EP | 2114499 | A1 | 11/2009 | |
| JP | 2001252358 | A | 9/2001 | |
| WO | 2019/038566 | A1 | 2/2019 | |
| WO | WO-2019038566 | A1 * | 2/2019 | ............ A61M 16/00 |

OTHER PUBLICATIONS

DE19605695A1_ENG (Espacenet machine translation of Dittmann) (Year: 1997).*

Jodi D. Sherman, MD, and Lauren Berkow, MD, FASA, Scaling pp Inhaled Anesthetic Practice Improvement: The Role of Environmental Sustainability Metrics, Anesthesia & Analgesia, Jun. 2019, vol. 128, No. 6, pp. 1060-1062.

* cited by examiner

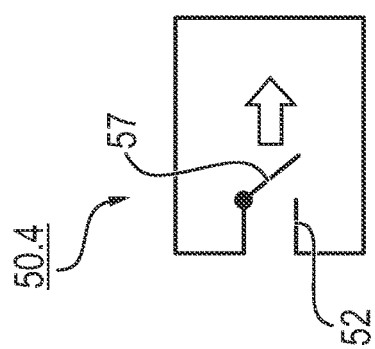
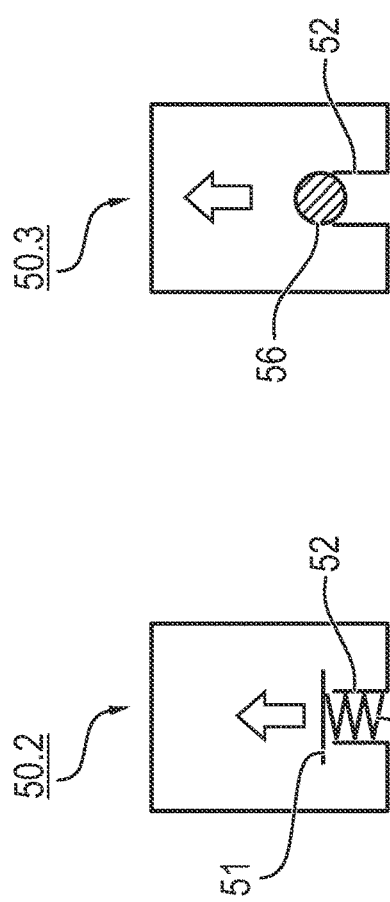
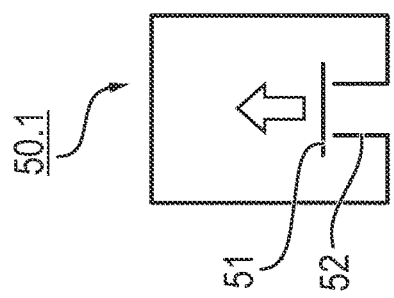
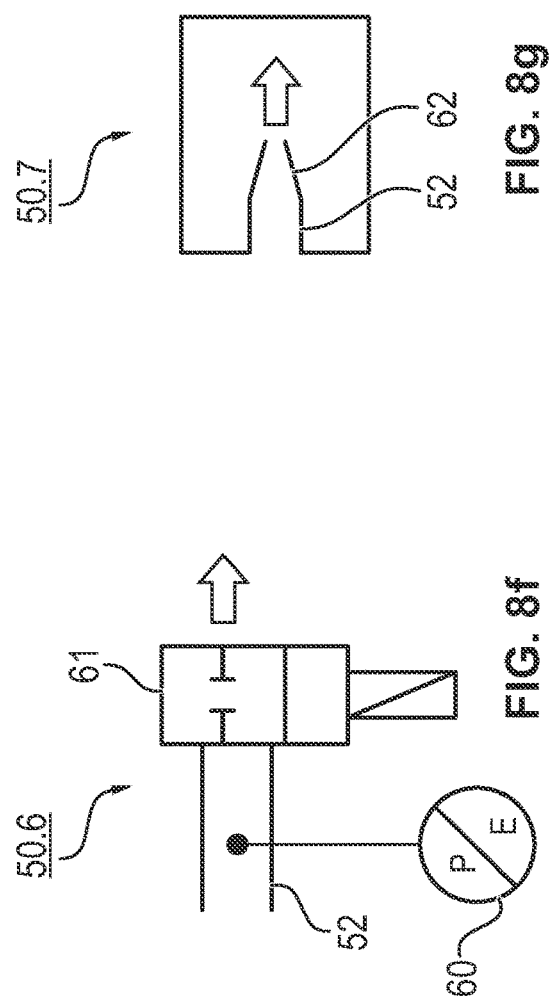
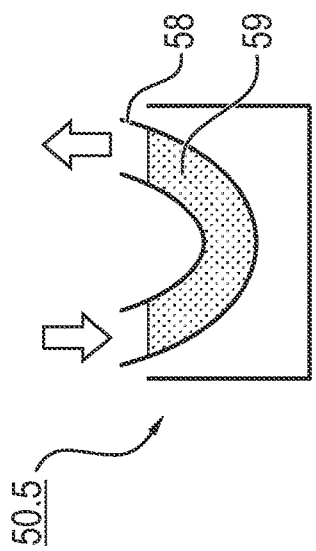

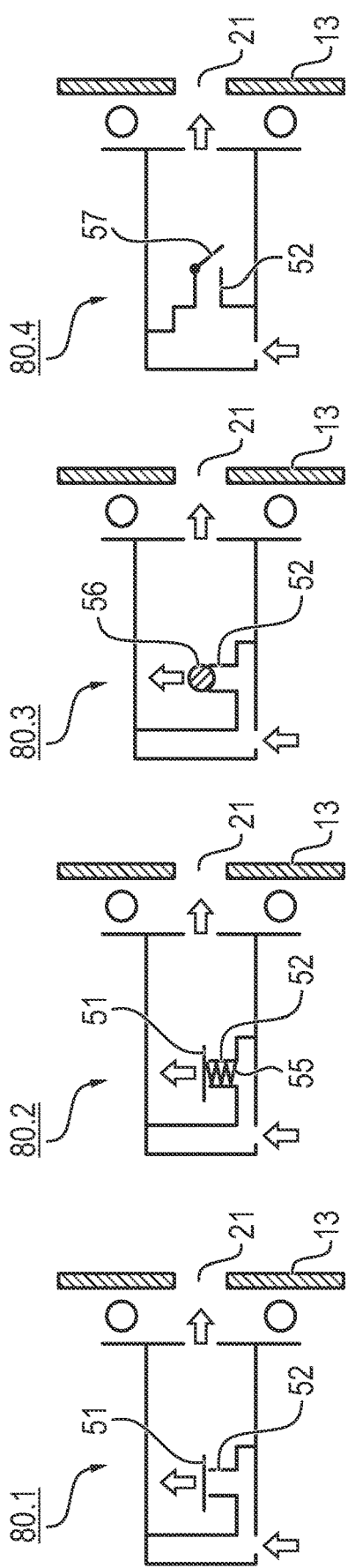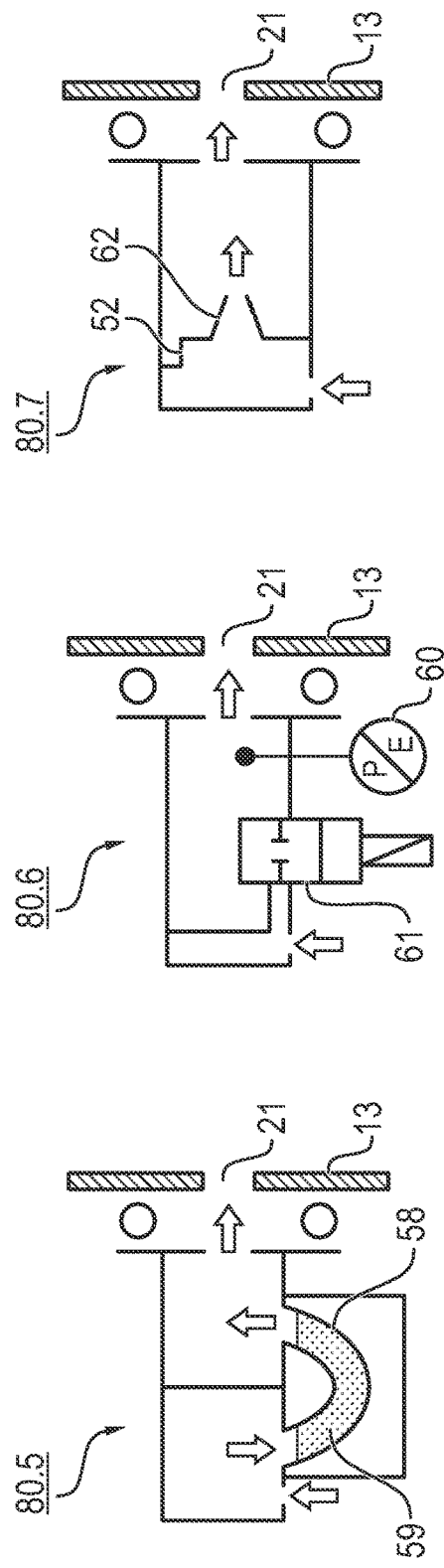

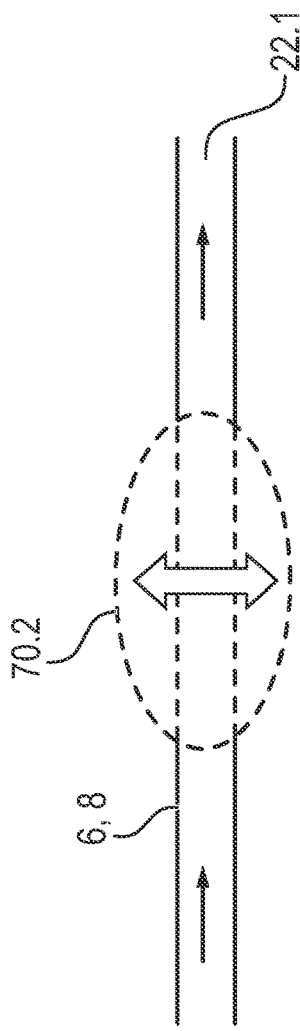
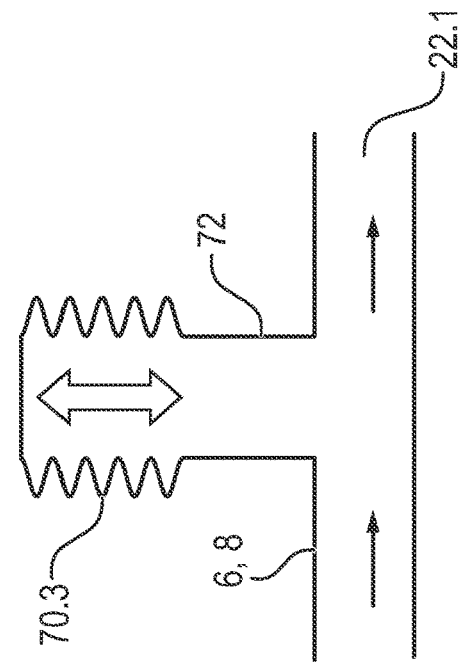
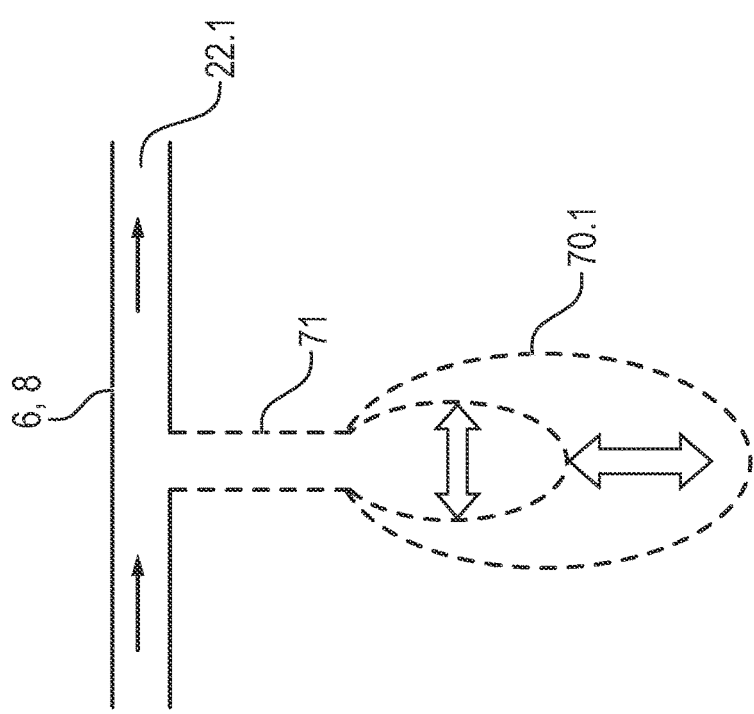

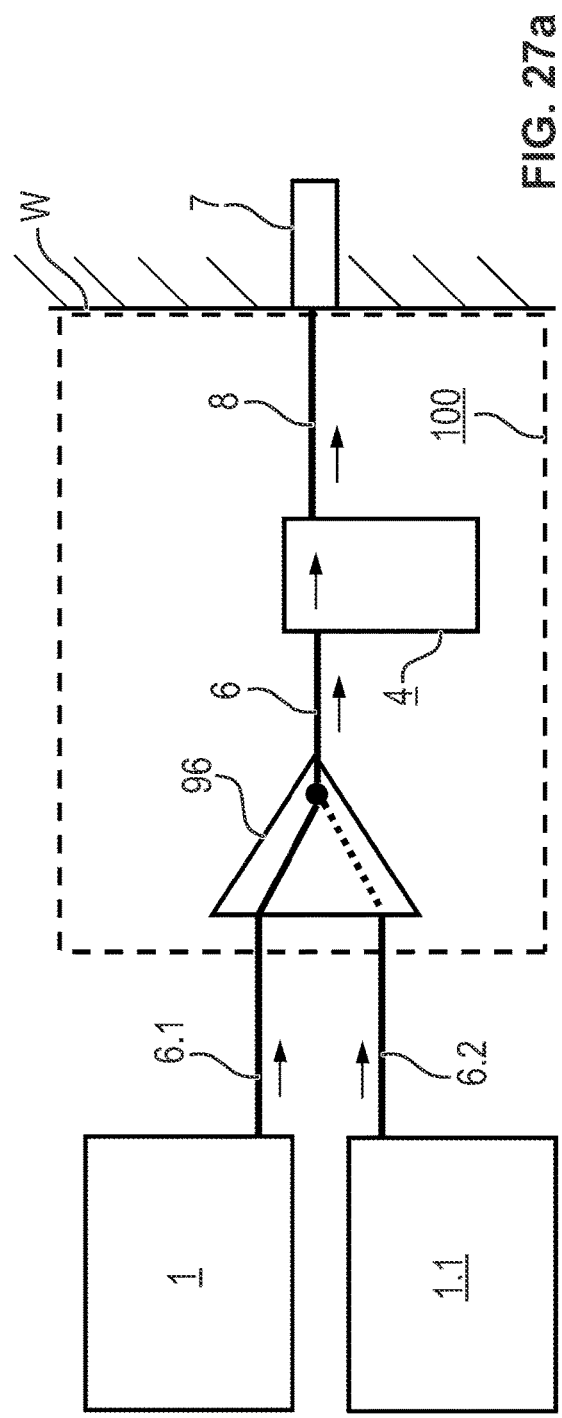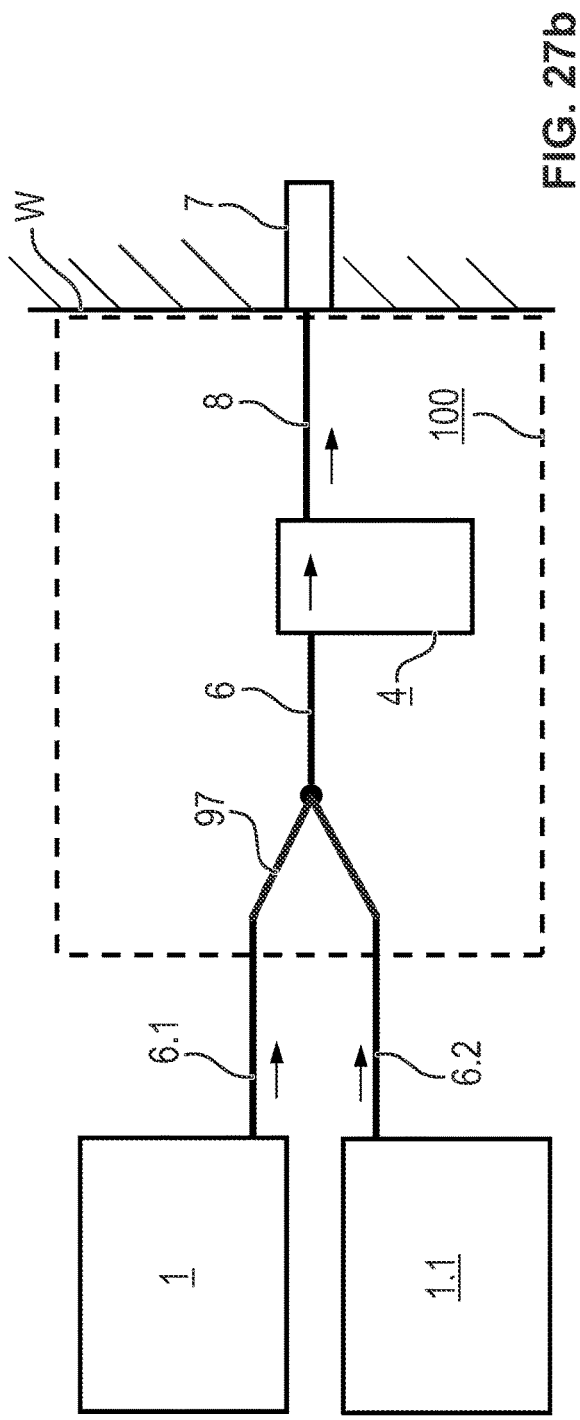

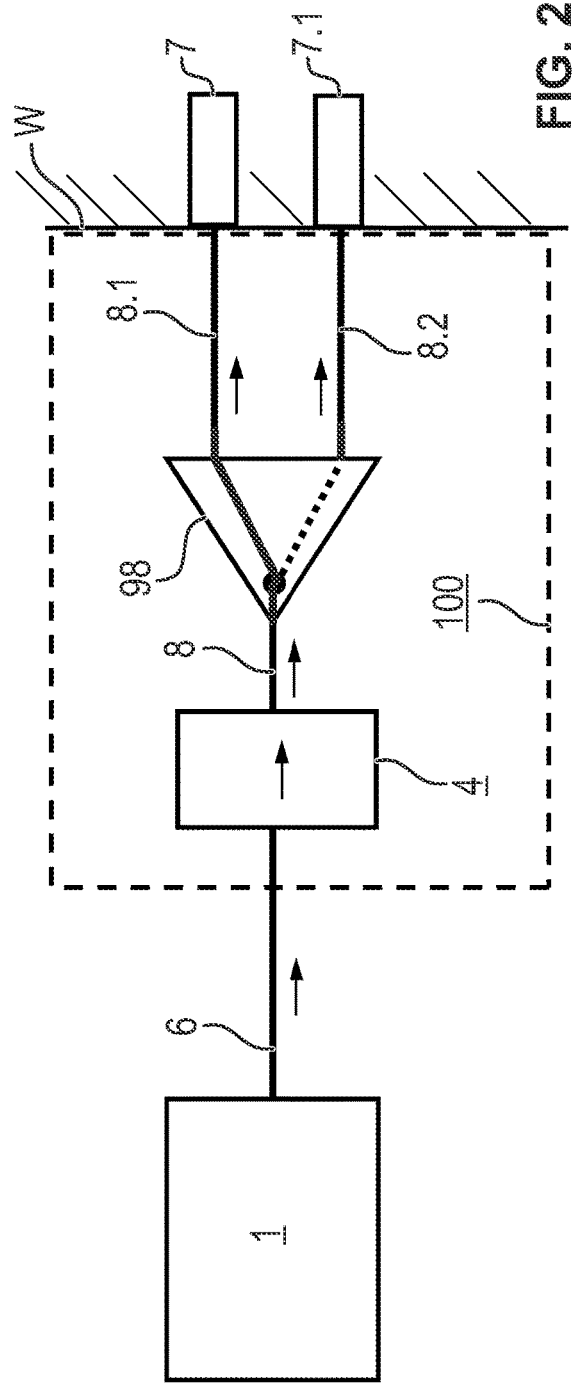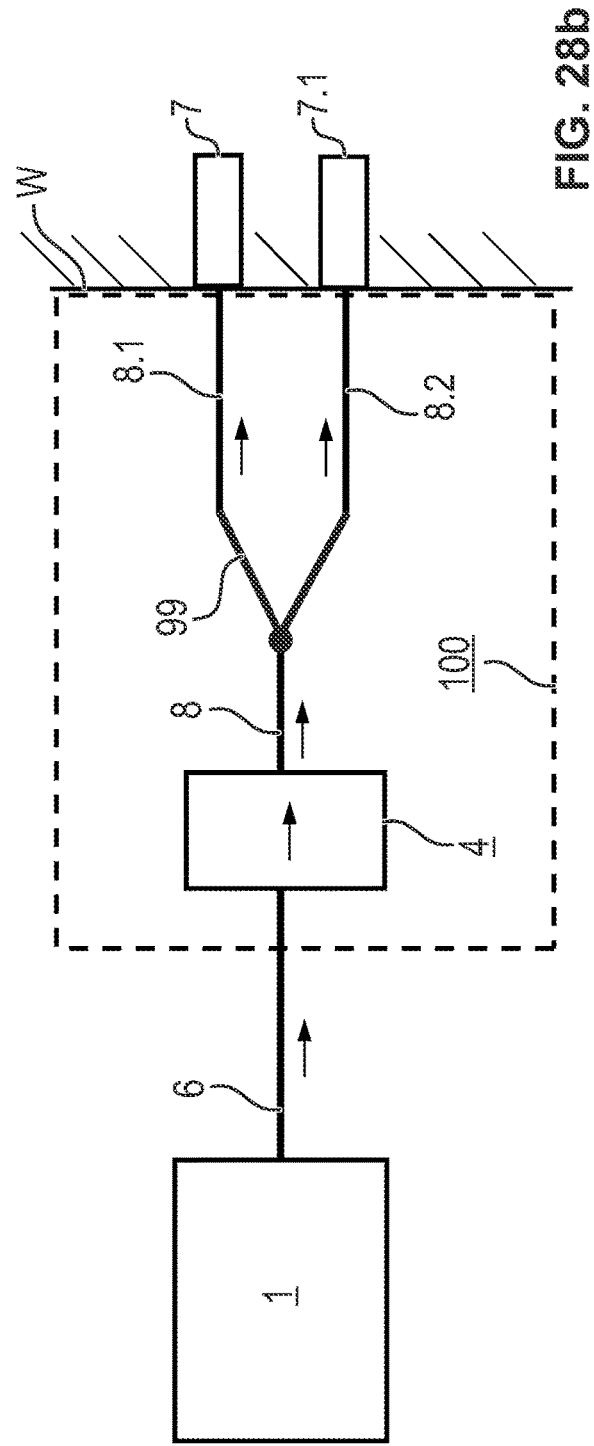

TAKING UP SYSTEM AND PROCESS WITH A FILTER UNIT FOR THE RECEIVING OF GAS FROM A MEDICAL APPARATUS

CROSS REFERENCE TO RELATED APPLICATIONS

This application claims the benefit of priority under 35 U.S.C. § 119 of German Application 10 2020 115 602.2, filed Jun. 12, 2020, and Luxembourg Application LU102192, filed Nov. 12, 2020 the entire contents of which are incorporated herein by reference.

TECHNICAL FIELD

The invention pertains to an taking up/receiving system, which is capable of taking up/receiving, especially sorbing, gas from a medical apparatus, especially from an anesthesia apparatus. The present invention further pertains to a process for taking up/receiving gas from a medical apparatus by means of such a taking up/receiving system.

TECHNICAL BACKGROUND

In an application of the taking up/receiving system and of the process, the medical apparatus is an anesthesia apparatus which is connected to a patient and which ventilates and anesthetizes the patient by means of a ventilation circuit. The anesthesia apparatus is supplied with the required gases and, in turn, supplies the patient with a gas mixture, wherein the gas mixture contains oxygen and is enriched with at least one anesthetic, so that the patient is fully or at least partly anesthetized. The anesthesia apparatus typically performs ventilation strokes, and a defined quantity of gas is fed to the patient with each ventilation stroke. The air exhaled by the patient reaches the medical apparatus again in one embodiment, and the medical apparatus filters carbon dioxide out of the exhaled air.

An anesthetic filter (anesthetic gas filter 2) with a housing (enclosure 4), an inlet (6) and an outlet (8) is described in US 2001/0 025 640 A1. A partition (18) with a hole 20 divides the housing 4 into a first chamber (first absorption volume 10) for a first filter (first absorbent 12) and a second chamber (second absorption volume 14) for a second filter (second absorbent 16). In case the first filter 12 is removed from the first chamber 10, then a first line (first shunt line 24) connects the inlet 6 to the hole 20 and thus to the second chamber 18. In case the second filter 16 is removed from the second chamber 14, then a second line (second shunt line 26) connects the hole 20 and thus the second chamber 14 to the outlet 18. Two anesthetic indicators 22 and 22B indicate when the first filter 12 and the second filter 16 have to be replaced.

Frequently, more gas is fed to the ventilation circuit than is removed again during a mechanical ventilation. In this case, excess gas accumulates in the ventilation circuit. This excess gas has to be removed from the ventilation circuit. It frequently contains an anesthetic. Of course, the patient should not be put at risk. In particular, the mechanical ventilation and the anesthetization have to be maintained.

SUMMARY

A basic object of the present invention is to provide an taking up/receiving system and a process for the taking up/receiving of gas from a medical apparatus, which perform their function better than the prior-art absorption systems and processes.

The object is accomplished by a taking up/receiving system with the features of the invention as well as by a process with the inventive features. Advantageous embodiments are described. Advantageous embodiments of the taking up/receiving system according to the present invention are, if meaningful, also advantages of the process according to the present invention and vice versa.

The taking up/receiving system according to the present invention comprises a feed line and a discharge line. The feed line can be connected, preferably can be connected detachably, to the medical apparatus, from which gas to be taken up/received is being released and is configured, after establishing the connection, to establish at least one fluid connection between the medical apparatus and the taking up/receiving system. The discharge line can be connected, preferably can be connected detachably, to a fluid taking up/receiving unit and is configured, after establishing the connection, to establish at least one fluid connection between the fluid taking up/receiving unit and the taking up/receiving system. The fluid taking up/receiving unit may be a stationary or a mobile fluid taking up/receiving unit and functions as a sink for fluid. The fluid taking up/receiving unit may also be a suctioning unit arranged at a distance in space within or outside of a building. As an alternative, the discharge line leads into the surrounding area.

The taking up/receiving system according to the present invention comprises, furthermore, a filter unit. The filter unit comprises at least one filter.

The filter or each filter of the filter unit is configured to filter at least one respective predefined gas component out of a gas that is passed through the filter. The construction and/or the nature of the filter and/or filter materials determine which gas component or which gas components the filter filters out. The filter is preferably capable of filtering at least one anesthetic out of the gas, i.e., the gas component or at least one gas component is an anesthetic.

The taking up/receiving system is configured to perform the following function: Gas, which is discharged or suctioned from the medical apparatus, or is released from the apparatus in a different way, is guided through the feed line to the filter unit and through the filter unit, wherein the filter unit comprises a filter. At least some of this gas, preferably all the gas, is passed through the filter, and the filter filters the gas component or at least one gas component out of the gas, especially at least partially, preferably completely—unless the filter is spent or defective. The gas, which has flowed through the filter unit and from which at least one gas component has been filtered out, is guided through the discharge line to the fluid taking up/receiving unit or into the surrounding area.

The process according to the present invention is carried out using such an taking up/receiving system and comprises the following steps:

At least one fluid connection is established between the medical apparatus and the feed line.

At least one additional fluid connection is established between the discharge line and the fluid taking up/receiving unit. As an alternative, the discharge line is or will be guided into the surrounding area.

Gas is released from the medical apparatus. In particular, the medical apparatus discharges this gas, and/or this gas is suctioned from the medical apparatus.

The taking up/receiving system passes the released gas through the feed line, the filter unit and the discharge line to the fluid taking up/receiving unit.

While this gas is being passed through the filter unit, at least some of this gas flows preferably continuously through the filter of the filter unit, or all the gas flows through the filter of the filter unit at least from time to time.

The filter filters the gas component or at least one predefined gas component, especially at least one anesthetic, out of the gas, which flows through the filter. Hence, gas, from which the gas component or at least one gas component is fully or at least partially filtered out, reaches the discharge line.

The taking up/receiving system according to the present invention comprises, furthermore, at least one buffer storage device, wherein the buffer storage device or each buffer storage device is in a respective fluid connection with the feed line at least from time to time, is in a respective fluid connection with the discharge line at least from time to time or is in a respective fluid connection both with the feed line and with the discharge line at least from time to time. Hence, gas, which is released from the medical apparatus, can reach the buffer storage device or a buffer storage device and again be released from this buffer storage device and then reach the discharge line. The process according to the present invention is carried out by using at least one such buffer storage device.

The taking up/receiving system according to the present invention and the process according to the present invention reduce, on the one hand, the risk that gas having an undesirable gas component is released into the surrounding area of the medical apparatus. In particular, the taking up/receiving system according to the present invention and the process according to the present invention reduce the risk that an anesthetic is released into the ambient air and the released anesthetic puts the health of people who are located in the vicinity of the medical apparatus and/or in the vicinity of the patient who is being mechanically ventilated, especially people who work in a hospital, at risk. This effect is especially achieved by the taking up/receiving system according to the present invention and the process according to the present invention sending the gas being released or gas released from the medical apparatus into the fluid taking up/receiving unit. As a result, discharged gas is prevented entirely or at least up to a certain extent from being released and reaching the surrounding area of the medical apparatus.

On the other hand, the present invention reduces the risk that gas being released or released gas reaches a supply system or the surrounding area, for example, an outside area outside the hospital.

In one application of the present invention, the fluid taking up/receiving unit is a stationary fluid taking up/receiving unit and belongs especially to a stationary infrastructure of a building. In this application, in many cases the taking up/receiving system according to the present invention and the process according to the present invention reduce the risk that a gas with an undesirable gas component reaches via the fluid taking up/receiving unit a stationary infrastructure system, to which the stationary fluid taking up/receiving unit is connected, and especially an infrastructure system in a hospital. This infrastructure system could discharge the gas with the undesirable gas component again to a medical apparatus, which is often undesirable, or could discharge this gas into the surrounding area, which could lead to pollution of the environment. This undesirable consequence is especially prevented by the filter unit with the filter. Such a filter, which is capable of filtering the gas component or at least one predefined gas component out of a gas, can be used as a component of the filter unit, while the gas is being passed through the filter.

It is also possible that the fluid taking up/receiving unit sends taken up/received gas into the vicinity of an exhaust air system via the discharge line and the exhaust air system suctions and takes up/receives the gas from a closed space or also from a partially or fully open space. In this application, the discharge line is not necessarily connected to a stationary fluid taking up/receiving unit. In this application as well, the present invention prevents the undesirable gas components of a gas from reaching the surrounding area.

According to the present invention, the taking up/receiving system additionally comprises at least one buffer storage device. This buffer storage device is directly or indirectly in at least one fluid connection with the feed line in one alternative, is directly or indirectly in at least one fluid connection with the discharge line in another alternative and is directly or indirectly both in a fluid connection with the feed line and in a fluid connection with the discharge line in a third alternative. "Indirectly" means that the fluid connection is being passed through another component of the system according to the present invention.

This buffer storage device is especially capable of temporarily taking up/receiving and temporarily storing gas that has been discharged or has been released in a different manner from the medical apparatus when the stationary fluid taking up/receiving unit is currently not capable or not entirely capable of taking up/receiving this gas. The buffer storage device reduces the risk that in this case a backup of the discharged gas occurs. This backup may react upon the medical apparatus and bring about a danger to a patient connected to the apparatus and/or damage to the medical apparatus. A larger backup could, in addition, let a fluid connection of the taking up/receiving system become leaky, for example, because of an excess pressure. It is not necessary in many cases, thanks to the buffer storage device, to reduce this excess pressure by the gas being released into the surrounding area. By releasing into the surrounding area, anesthetic could exist in the surrounding area, which is undesirable, as explained above. In addition, no action of a person is necessary in many cases thanks to the buffer storage device.

When more gas is released from the medical apparatus and reaches the feed line than the discharge line can receive, then gas is sent into the buffer storage device or into at least one buffer storage device, and especially preferably from the feed line. When less gas is released than the discharge line is able to receive, then gas again flows out of the buffer storage device and is preferably sent into the discharge line and from there into the fluid taking up/receiving unit.

It is required in many cases to replace the filter from time to time, especially if the filter has become clogged after a longer use. A mechanical ventilation of a patient must or should often be continued, while the filter or the entire filter unit is being replaced. A large quantity of excess gas should also in this case be prevented from reaching the surrounding area. A large quantity of anesthetic should especially also be prevented from reaching the surrounding area during a replacement of the filter. In this case, the buffer storage device or at least one buffer storage device according to the present invention of the taking up/receiving system also receives at least some of the excess gas, ideally all the excess gas, and releases it again later.

Because according to the present invention at least one buffer storage device is in a fluid connection with the feed line and/or with the discharge line, it is not necessary to connect in series two filter mounts, to provide a respective bypass line (bypass) for each fluid taking up/receiving unit and to ensure that at any time a filter is inserted into at least one filter mount. Such a series connection of two filter mounts requires in many cases more space than a single filter mount and a buffer storage device. The buffer storage device according to the present invention may be arranged at a distance in space from the filter mount. In addition, thanks to the present invention no bypass line (bypass) about a filter mount is necessary in many cases.

In the sense of the claims, a "filter" is defined as a component, which is capable of filtering at least one gas component out of a gas mixture, while this gas mixture flows through the filter. The filter may bind itself to the gas component, for example, with activated carbon and/or because the filter contains zeolite. The filter may also break up the gas component chemically or thermally. The filter may also act mechanically and, for example, comprise a molecular sieve. A plurality of actions may be combined.

A "line" in the sense of the claims is a fluid guide unit, which connects two points in a fluid-tight manner and thus also in a gas-tight manner and is capable of carrying fluid from the one point to the other point. The line may be flexible, may especially be a pleated hose or a smooth hose, or may be rigid, especially a pipe or a tube. A line in the sense of the claims may also be a fluid-tight coupling point, which detachably connects the filter unit to another apparatus.

A "buffer storage device" for gas is defined as a chamber for receiving gas, which is enclosed by a wall. This gas contains in one application at least one anesthetic. The chamber is arranged such that it is capable of taking up/receiving more of this gas than releasing in a first time period, and is capable of again releasing the gas taken up/received in the first time period or an equal quantity of this gas in a subsequent second time period. In the first time period, the volume flow of this gas into the buffer storage device is thus greater than the volume flow of this gas from the buffer storage device and the volume flow of this gas is smaller in the second time period. According to the present invention, gas flows from the feed line and/or from the discharge line into the buffer storage device or into a buffer storage device in the first time period, and gas flows from the buffer storage device again into the feed line and/or into the discharge line in the second time period.

In one embodiment, the buffer storage device or a buffer storage device is connected only at one point to the feed line and not at all to the discharge line or only at one point to the discharge line and not at all to the feed line. In this embodiment, gas flows at this point into the buffer storage device and again from the buffer storage device at the same point.

In another embodiment, the buffer storage device or a buffer storage device is connected to the feed line and/or the discharge line at two different points, which are arranged at a distance from one another. In this other embodiment, the cross-sectional area of the buffer storage device is larger than the cross-sectional area of the feed line and larger than the cross-sectional area of the discharge line. Thanks to this larger cross-sectional area, the buffer storage device is capable of temporarily storing gas in this other embodiment.

The volume of the chamber and/or the pressure prevailing in the chamber increases over the course of the first time period in one embodiment. The volume or the pressure preferably doubles in this first time period. The volume or the pressure are again reduced in the course of the second time period. After the end of the second time period, the volume and the pressure are preferably again as low as at the beginning of the first time period. The wall of the buffer storage device may be rigid or elastic, so that the volume of the buffer storage device is constant or else variable as a function of the difference between the pressure in the buffer storage device and the pressure from outside on the buffer storage device.

In one embodiment, the wall separates the chamber of the buffer storage device from the surrounding area in a fluid-tight manner. It is also possible that the buffer storage device is in a fluid connection with the surrounding area and the gas in the first time period displaces air from the buffer storage device, so that air flows into the surrounding area, and the gas is fed from the buffer storage device and air again flows into the buffer storage device in the second time period. In this embodiment, the volume and the pressure in the chamber may remain constant. Also in this embodiment, the buffer storage device reduces the risk that a large quantity of anesthetic is released into the surrounding area.

By contrast, a line for gas always has the same volume during a trouble-free operation, is not in a fluid connection with the surrounding area during a trouble-free operation and has the object of carrying gas from one feed point to a discharge point. As a rule, the volume flow in the line is at any time equal to the volume flow out of the line.

According to the present invention, the filter unit comprises a filter. Preferably, the filter unit additionally comprises a filter mount. The filter is inserted into the filter mount or can be inserted into the filter mount and preferably be removed again from the filter mount. The filter mount is in a respective fluid connection with the feed line and with the discharge line. In one embodiment, the inserted filter can again be removed from the filter mount, for example, in order to be replaced with a new filter or with a different filter (filter with different filter properties). According to a preferred embodiment, the filter can be inserted into the filter mount and can later be removed again from the filter mount. As a result, it is made possible to replace a filter, when this filter has taken up/received such a quantity from the gas component or from a gas component of the gas released from the medical apparatus that the filter cannot fulfil its desired filter action at all or no longer to a sufficient extent, and/or when the filter has become clogged.

Thanks to the filter mount, it is not necessary to separate and later again establish a fluid connection between the feed line and the discharge line or with the medical apparatus from time to time in order to replace a filter. As a result, a spent filter can be rapidly replaced with a new filter. The risk of an error during the first establishing or during a re-establishing of the fluid connection is reduced. In addition, it is possible to use the same taking up/receiving system with different filters one after the other in the filter mount and as a result to filter different gas components out of the gas and/or to use the taking up/receiving system under different ambient conditions. This feature makes it easier, in addition, to provide a plurality of taking up/receiving systems according to the present invention for different intended purposes, especially for filtering out different gas components. These taking up/receiving systems according to the present invention need to be distinguished only by the filters having different configurations. The remaining components of the taking up/receiving system may correspond or may be distinguished only by dimensions.

In the embodiment with the filter mount, the process according to the present invention comprises the following additional steps:

In case it has not already happened, a filter is inserted into the filter mount.

The taking up/receiving system sends the gas, which has been released from the medical apparatus, through the feed line, the filter mount and the discharge line to the fluid taking up/receiving unit or into the surrounding area.

The taking up/receiving system sends the gas through the filter mount such that at least some of the gas, preferably all the gas, flows through the filter, wherein the filter is inserted into the filter mount.

In an alternative, the filter forms a fixed component of the filter unit, and the entire filter unit is a single component. The feed line and the discharge line can preferably be connected and especially preferably be connected detachably to the filter unit. In case the filter is spent and is not capable of taking up/receiving an additional quantity of the gas component or in case the filter is clogged, the filter unit together with the filter is separated from the feed line and from the discharge line and a new filter unit is connected to the feed line and to the discharge line.

An embodiment, in which the filter unit comprises a filter mount and at least one filter, was already described further above. The filter or a filter can be inserted into the filter mount and can again be removed from the filter mount, for example, in order to replace the filter with a new filter. The filter unit comprises, furthermore, a filter sensor in a preferred variant. This filter sensor is capable of automatically determining whether or not a filter has been inserted into the filter mount. The filter sensor preferably generates a message in case no filter has been inserted into the filter mount. In one embodiment, the filter sensor generates this message only if no filter has been inserted into the filter mount for a time period, which is longer than a predefined time period. In one variant, the filter sensor generates a message only if no filter has been inserted for a period longer than the time period and additionally gas is flowing through the feed line. The embodiment with the filter sensor reduces the risk that no filter has unintentionally been inserted into the filter mount and therefore no gas component can be filtered out and a larger quantity of the gas component reaches the fluid taking up/receiving unit. On the other hand, in many cases a useless alarm is avoided when a filter is being replaced.

The buffer storage device or at least one buffer storage device is preferably not only in a fluid connection with the feed line and/or with the discharge line, respectively, but additionally in a fluid connection with the surrounding area, especially over the long term or at least in case of a great pressure difference between the interior of the buffer storage device and the surrounding area. The buffer storage device is thus located between the feed line and/or the discharge line and the surrounding area. As a result, the risk is further reduced that in case of a large quantity of gas that is being released from the medical apparatus, a backup occurs when neither the stationary fluid taking up/receiving unit nor the buffer storage device can entirely take up/receive this quantity. In fact, it is undesirable that gas is released into the surrounding area. However, the release of gas into the surrounding area is usually less harmful than a backup of this gas. The embodiment that the buffer storage device is in a fluid connection with the surrounding area is especially advantageous if the buffer storage device is rigid, i.e., its volume is not variable. A buffer storage device with constant volume is frequently more mechanically stable than a buffer storage device with variable volume because its housing may be rigid. In addition, the fluid connection with the surrounding area leads to no excess pressure arising in the buffer storage device, which is undesirable in some cases.

In one embodiment, the filter unit comprises a plurality of filters that are connected in parallel. The taking up/receiving system is configured such that gas flows through the feed line, through at least one of these filters and through the discharge line. One filter is thus located in the flow path from the feed line to the discharge line. In one embodiment, the gas flows through one filter, and at least one additional filter is located in a reserve position. In another embodiment, the gas is split into at least two parallel flows, and each flow flows through a respective filter.

In one embodiment, the filter unit comprises a receiving unit, especially a turret holder, for at least two filters. This receiving unit is movable in relation to the feed line and in relation to the discharge line. The current position of the receiving unit in relation to the feed line determines which filter is currently being used and which filter is located in a reserve position. In another embodiment, the filter unit comprises a switch, which selectively sends the gas flowing out of the feed line to the first filter or to the second filter, or a Y-piece, which splits the gas into two parallel flows and thus into two filters.

In one application of the embodiment with a plurality of filters, all the filters of the filter unit have a similar configuration and are especially capable of filtering out the same gas component. When a filter is spent or clogged, the receiving unit is moved in relation to the feed line and in relation to the discharge line, so that the gas flows through a new filter. For example, the filter unit comprises a drive for the receiving unit.

A first filter in the receiving unit is capable of filtering out a first gas component, a second filter is capable of filtering out a second gas component and optionally a third filter is capable of filtering out the first gas component, the second gas component and a third gas component in another embodiment. The three gas components differ from one another chemically and/or mechanically. Depending on the desired or necessary application, the first filter or the second filter or the optional third filter are moved into the flow path from the feed line into the discharge line. The filter unit preferably comprises a selection unit, by means of which a user can select a gas component to be filtered out. It is also possible that upstream of the filters is arranged a sensor, which detects which gas component being filtered out is located in the gas that is flowing to the filters. As a function of a signal of this sensor, the correct filter is moved into the flow path of the gas. Or a corresponding message is outputted to a user.

Various embodiments of the buffer storage device are possible, and at least some of these embodiments can be combined with one another. It is thus possible that the taking up/receiving system according to the present invention comprises precisely one buffer storage device or else at least two similar buffer storage devices or even at least two different buffer storage devices.

In an already mentioned embodiment, the filter unit comprises a filter mount, into which a filter can be inserted or is inserted. In a variant of this embodiment, the space, which is enclosed by the filter mount, is greater in at least one direction than the filter—more precisely. An intermediate space is located between at least one inner wall of the filter mount and the opposing outer wall of the filter. It is possible that this intermediate space adjoins two outer walls of the filter, e.g., the lateral surface and an end face, or also only an outer wall, e.g., only the lateral surface. This intermediate space is in a respective fluid connection with the feed line and with the discharge line and forms the buffer storage device or a buffer storage device or belongs to the buffer storage device or belongs to a buffer storage device. This intermediate space preferably occupies at least 10%, especially preferably even at least 20%, especially at least 30% of the space enclosed by the filter mount. Preferably, the intermediate space is delimited in a fluid-tight manner against the surrounding area, so that no gas can escape from the intermediate space into the surrounding area.

The embodiment with the intermediate space occupies especially less space compared with other possible embodiments of the buffer storage device and is mechanically robust. The intermediate space in some embodiments makes it easier, in addition, for a person to grasp the filter in the intermediate space and to remove it from the filter mount.

In a time period, in which no filter has been inserted into the filter mount, the entire interior of the filter mount is frequently available as a buffer storage device. In case of the embodiment just described, this interior is larger than when the filter mount encloses the filter without intermediate space, and hence is capable of taking up/receiving more gas. Hence, only relatively little gas, which has been released from the medical apparatus, reaches the surrounding area, even though no filter has been inserted and the filter mount is hence open to the surrounding area. This desired situation occurs especially if the filter mount is open upwards and the gas, which is being released from the medical apparatus, is heavier than air. Most anesthetics are heavier than air.

In the embodiment with the filter mount, which encloses a cavity, the cavity of the buffer storage device is preferably separated in space from the cavity for receiving the filter and is preferably separated, especially separated in a fluid-tight manner, for example, by means of a stationary or movable plate.

In another configuration, the buffer storage device comprises a housing, which encloses a cavity and is a rigid housing in one embodiment and an elastic housing in another embodiment and a housing with at least one rigid area and with at least one elastic area in a third embodiment. This housing is in at least one respective fluid connection with the feed line and with the discharge line. The embodiment with the buffer storage device, which comprises a housing, can also be combined with an embodiment, in which the filter unit forms a single component. In one embodiment, this housing of the buffer storage device is additionally in at least one fluid connection with the filter unit, and the fluid connection exists between the housing and the feeding line and/or leads through the filter unit.

A plurality of plates or other suitable guide elements, which provide a preferably meandering path through the housing, are installed in the interior, which the housing of the buffer storage device encloses. This configuration makes it possible for the housing to be in a fluid connection with the surrounding area and nevertheless only a relatively small quantity of gas is released from the housing into the surrounding area. The meandering path leads to gas flowing only slowly through the interior of the housing. The buffer storage device may have a rigid housing.

In one embodiment, this housing is in a fluid connection with the surrounding area, so that excess gas can be released into the surrounding area. In case a meandering path is formed in the housing, then only relatively little gas is frequently released into the surrounding area in spite of the fluid connection.

The buffer storage device is preferably configured in both configurations such that it functions according to the "last-in-first-out" principle.

In one embodiment, the housing of the buffer storage device is arranged at right angles to or obliquely below the filter unit and is preferably in a fluid connection with the filter unit. This configuration is especially advantageous when a gas with the gas component to be filtered out is heavier than air and therefore sinks downwards in the filter unit. Most anesthetics are heavier than air.

In one embodiment, the housing of the buffer storage device is arranged downstream of the filter unit. In an alternative embodiment, the filter unit is arranged downstream of the buffer storage device housing. The term "downstream" refers to a direction of flow of fluid from the feed line to the discharge line. These two configurations lead to a lesser vertical expansion of the taking up/receiving system according to the present invention compared with other possible embodiments.

It is possible that both an intermediate space is formed between the inserted filter and the filter mount and a separate housing of the buffer storage device is arranged below or downstream or upstream of the filter unit. This embodiment makes it possible to provide an especially large buffer storage device. The risk that gas will be released into the surrounding area is further reduced.

As was already mentioned, the filter unit in one embodiment comprises a filter mount, into which a filter can be inserted or is inserted. In another variant of this embodiment, a plate is inserted into the filter mount. This plate divides the interior of the filter mount into a filter cavity, which is configured for receiving the filter, and a buffer storage device cavity, which belongs to the buffer storage device or to a buffer storage device, or forms a buffer storage device. At least when no filter has been inserted into the filter mount, this buffer storage device cavity is, on the one hand, in a fluid connection with the feed line and, on the other hand, in a fluid connection with the discharge line.

The plate reduces the risk that gas reaches the surrounding area from the fluid taking up/receiving unit, and especially even if no filter has been inserted into the filter mount. This embodiment with the plate in the filter mount likewise saves space compared with other possible embodiments of the buffer storage device. The need to provide a separate housing for the buffer storage device is spared.

In one embodiment, the buffer storage device cavity is located below the filter cavity. The plate is preferably arranged horizontally. This embodiment is especially advantageous when a gas with the gas component to be filtered out is heavier than air and hence sinks downwards in the filter mount. Most anesthetics are heavier than air.

The plate may be fastened in a stationary manner in the filter mount. In one embodiment, the plate may, by contrast, be moved back and forth between a park position and a buffer storage device position in relation to the filter mount. When a filter has been inserted into the filter mount, the plate is located in the park position, otherwise in the buffer storage device position. The feed line comprises at least one outlet opening, which is preferably arranged in the interior of the filter mount. The discharge line comprises at least one inlet opening, which is preferably arranged in the interior of the filter mount.

When the plate is in the buffer storage device position, the following situation is established according to this embodiment:

The outlet opening or an outlet opening connects the feed line to the buffer storage device cavity.

The inlet opening or an inlet opening connects the buffer storage device cavity to the discharge line.

As a result, the buffer storage device cavity is in a respective fluid connection both with the feed line and with the discharge line.

In one embodiment, the plate seals the buffer storage device cavity in a largely fluid-tight manner against the surrounding area and against the filter cavity. The filter mount seals both cavities against the surrounding area.

When the plate is in the park position, then the following situation is established according to this embodiment:

The outlet opening or an outlet opening connects the feed line to the filter cavity.

The inlet opening or an inlet opening connects the discharge line to the filter cavity.

As a result, the filter cavity and also a correctly inserted filter are in a fluid connection both with the feed line and with the discharge line.

In one embodiment, the plate in the park position separates the two openings, which use the feed line and the discharge line with the filter cavity, in a fluid-tight manner from the buffer storage device cavity.

In another embodiment, even if the plate is in the park position, the feed line and/or the discharge line is/are in a fluid connection with the buffer storage device cavity.

The buffer storage device cavity provides a buffer storage device in the interior of the filter mount when the plate is in the buffer storage device position. This buffer storage device is hence capable of taking up/receiving gas from the medical apparatus when no filter is currently inserted. This situation occurs especially when the filter in the filter mount is being replaced. The plate in the buffer storage device position separates the buffer storage device cavity against the surrounding area and reduces the quantity of gas that is released into the surrounding area.

Thanks to the movable plate, no additional mechanism needs to be provided in order to achieve a desired filtering, on the one hand, and to prevent gas from being released into the surrounding area, on the other hand. The plate makes possible a relatively simple mechanical construction.

In one embodiment, the filter unit is configured such that when a filter has been inserted into the filter mount, the plate is moved from the buffer storage device position into the park position. When the filter is again removed from the filter mount, the plate is moved from the park position again into the buffer storage device position. For example, a mechanical or pneumatic spring aims to move the plate into the buffer storage device position and to hold it in this position. This spring is preferably supported at a housing of the filter mount.

In one embodiment, the filter unit is configured such that a movement of the plate from the park position into the buffer storage device position pushes the filter out of the filter mount.

In one embodiment, the plate is connected to an actuating element, which is preferably accessible from outside of the filter mount and can preferably be actuated manually to move the plate back and forth between the two positions. For example, a filter is inserted into the filter mount, and then the actuating element is actuated to move the plate into the park position. As a result, the filter is also inserted entirely into the filter mount. In order to remove the filter, the actuating element is actuated again and moves the plate into the buffer storage device position. As a result, the filter is pushed out of the filter mount.

In another embodiment, a drive is capable of moving the plate back and forth between the two positions. The drive can preferably be actuated and/or activated from outside.

The plate preferably snaps into place in at least one end position, especially preferably in both end positions.

The park cavity is preferably smaller than the buffer storage device cavity. Therefore, this embodiment saves space compared with other possible embodiments of the buffer storage device.

In one embodiment, an actuating element to be actuated manually and/or a drive are connected to the plate. The plate can be moved from the one position into the other position by means of the actuating element. The drive is capable of moving the plate from the one position into the other position.

In a preferred embodiment, by contrast, the insertion as well as the removal of the filter cause the plate to be moved from the one position into the other position and as a result the flow of gas is sent through the filter cavity or through the buffer storage device cavity. This embodiment spares a separate actuating element or a separate drive. It is possible that a latching unit holds the plate in a position.

The plate is preferably spring-mounted in the filter mount. At least one spring element aims to move the plate into the buffer storage device position, especially to move it upwards. The spring element is preferably supported at the filter mount. An inserted filter moves the plate against the force of the spring into the park position, preferably because of its own weight and/or because of a force effect during the insertion of the filter. This embodiment spares the need to provide an actuating element and/or an action and/or a drive to move the plate from the one position into the other position. The plate is, rather, automatically moved from the one position into the other position during insertion and during removal. It is also possible that a snap-in connection or a locking holds the plate in the park position.

According to the just described embodiment, a plate in the interior of the filter mount separates a filter cavity from a buffer storage device cavity, especially in a fluid-tight manner in one embodiment.

In a variant of this fluid-tight embodiment, a slide, which is preferably connected mechanically to the plate, is additionally located in the interior of the filter mount. The slide can also be moved back and forth between a park position and a buffer storage device position, preferably together with the plate.

The feed line comprises according to this embodiment two outlet openings, which are arranged at a distance in space from one another, specifically a filter outlet opening and a buffer storage device outlet opening. The discharge line also comprises two inlet openings, which are arranged at a distance in space from one another, specifically a filter inlet opening and a buffer storage device inlet opening.

When the plate and the slide are in the park position, then the feed line is connected to the filter cavity via the filter outlet opening. The discharge line is connected to the filter cavity via the filter inlet opening. The slide blocks the buffer storage device outlet opening and the buffer storage device inlet opening. Gas that is released from the feed line is carried through the filer cavity and thus through the filter into the discharge line. The slide in the park position prevents gas from bypassing the filter in the filter mount and flows from the feed line through the buffer storage device cavity directly into the discharge line.

When the plate and the slide are in the buffer storage device position, then the feed line is connected to the buffer storage device cavity via the buffer storage device outlet opening. The discharge line is connected to the buffer storage device cavity via the buffer storage device inlet opening. The slide blocks the filter outlet opening and the filter inlet opening. Gas, which is released from the feed line, is carried through the buffer storage device cavity into the discharge line. The slide in the buffer storage device position prevents gas from being released from the feed line or from the discharge line and reaches the filter cavity and from there the surrounding area. In this embodiment as well, the plate in the buffer storage device position separates the buffer storage device cavity from the filter cavity, especially preferably in a fluid-tight manner.

The just described embodiment with the plate and the slide leads to an especially simple mechanical embodiment. It is possible that an actuating element to be actuated manually and/or a drive are capable of moving the slide. The insertion of a filter preferably causes the plate and the slide to be moved into the park position and to be held in this position. The removal of the filter causes the plate and the slide to be moved into the buffer storage device position and to be held in this position. In one embodiment, at least one mechanical or pneumatic spring aims to move the plate and the slide into the buffer storage device position and hold them in this position. The spring is preferably supported at the filter mount. Instead of a spring, a different elastic element can also be used, which exerts a force onto the slide.

In one embodiment, the volume of the buffer storage device or of at least one buffer storage device can be changed, preferably changed reversibly. In particular, the buffer storage device comprises a wall, which is entirely elastic or at least in one area. As a result, the buffer storage device can expand and contract again. The feed of gas expands the buffer storage device and as a results increases the volume thereof. The expanded buffer storage device is capable of again releasing stored gas, wherein the buffer storage device contracts and its volume is reduced. This embodiment leads in many cases to a buffer storage device having an especially simple configuration. A lower overpressure is formed in the interior of the buffer storage device compared with a buffer storage device, which has a rigid housing.

This expandable buffer storage device is preferably in a fluid connection with the feed line, and is thus arranged upstream of the filter unit. This embodiment causes the quantity of gas, which the filter unit reaches per time unit, to vary less widely over time. When the taking up/receiving system is connected to a medical apparatus, this embodiment reduces the risk that an undesirable high pressure has an effect on the medical apparatus and thus on a patient, who is connected to the medical apparatus. The expandable buffer storage device may also be in a fluid connection with the discharge line and may be arranged downstream of the filter unit.

In one embodiment, the taking up/receiving system comprises an expandable buffer storage device and a buffer storage device with a rigid housing and/or a buffer storage device in the interior of the filter mount. The elastic buffer storage device is preferably arranged upstream of the buffer storage device with the rigid housing. As a result, the quantity of gas, which reaches the rigid buffer storage device per time unit, varies less widely over time. It is also possible that the expandable buffer storage device is in a fluid connection with the other buffer storage device.

The taking up/receiving system according to the present invention is connected to a medical apparatus, and especially to an anesthesia apparatus, in one application. A bag for the manual ventilation of a patient is used as the buffer storage device or as a buffer storage device. This bag is connected to the feed line or to the discharge line. Such a manual ventilation bag is often already approved for medical use and possesses standardized dimensions. A connection piece of the taking up/receiving system according to the present invention can be adapted to these dimensions.

In one embodiment, the taking up/receiving system additionally comprises at least one pressure relief valve (overpressure valve) in or at the feed line. This pressure relief valve opens when a differential pressure in contact with the pressure relief valve is above a predefined overpressure threshold (pressure relief threshold). The open pressure relief valve releases gas into the surrounding area. The pressure relief valve is positioned such that it opens automatically, when the difference between the pressure in the feed line and the ambient pressure around the feed line is above the overpressure threshold. The pressure relief valve releases, as a result, an overpressure in the feed line and especially reduces the risk that a backup will occur in the feed line. This backup may have an undesirable effect on an apparatus, which discharges gas into the feed line.

This overpressure threshold is in one embodiment predefined by the structure of the pressure relief valve. In another embodiment, a pressure sensor measures the pressure difference present at the pressure relief valve. In one embodiment, a control device or a comparator receives measured values from this pressure sensor and actuates the pressure relief valve, specifically so that the pressure relief valve opens if the pressure difference is above the overpressure threshold. In another embodiment, the measured values are outputted from the pressure sensor in a form perceptible by a person. For example, an alarm is outputted if a pressure difference above the overpressure threshold is detected. The two embodiments, that the control device/the comparator actuates the pressure relief valve and that the measured values and/or an alarm are outputted, can be combined with one another.

In one embodiment, the pressure relief valve or an pressure relief valve is arranged in series with the filter unit and upstream of the filter unit, especially in or at the feed line. In another embodiment, the pressure relief valve or an pressure relief valve is arranged parallel to the filter unit. In this other arrangement, some of a gas flows through the feed line and around the filter unit when the pressure relief valve is open. In both embodiments, the feed line carries all the gas to the filter unit when the pressure relief valve is closed.

In one embodiment, the open pressure relief valve releases gas into the surrounding area. In another embodiment, a fluid guide unit, especially a hose or another line, connects the pressure relief valve to the discharge line. When the pressure relief valve is open, a fluid connection is established from the feed line through this fluid guide unit to the discharge line. In a third embodiment, the pressure relief valve is arranged in the interior of the filter unit. Also when the pressure relief valve is open, gas flows through the feed line and through the filter unit into the discharge line, without being released into the surrounding area. However, at least some of this gas does not flow through the filter of the filter unit, but around the filter. These two preferred embodiments reduce the risk that gas will be released into the surrounding area when the pressure relief valve is open. Rather, gas flows around the filter into the discharge line in case of an overpressure.

Another possible arrangement of the pressure relief valve can be combined with the embodiment that the filter unit comprises a filter mount, wherein a filter can be inserted into the filter mount and wherein the filter mount is in a respective fluid connection with the feed line and with the discharge line. In case of this embodiment, when the pressure relief valve is closed, the gas is carried from the feed line through the filter to the discharge line. Also when the pressure relief valve is open, the gas flows from the feed line through the interior of the filter mount into the discharge line. However, at least some of the gas then flows past the filter. This embodiment reduces the risk that gas can escape into the surrounding area when the pressure relief valve is open.

The pressure relief valve or an pressure relief valve may also be arranged at the filter mount or at or in the discharge line and release gas into the surrounding area in case of an overpressure.

In a variant of the embodiment with the pressure relief valve, at least one opening is formed in a wall of the filter unit. The pressure relief valve closes this opening. When the pressure relief valve opens because of an overpressure, then the filter unit is in a fluid connection with the surrounding area through the opening. It is also possible that an opening is arranged parallel to the pressure relief valve. The pressure relief valve is preferably closed again automatically when the overpressure is released.

In another embodiment, the taking up/receiving system comprises at least one vacuum valve. This vacuum valve opens when the difference between the pressure in the feed line or in the interior of the filter unit, on the one hand, and the surrounding pressure, on the other hand, is below a predefined vacuum threshold. Such a higher vacuum is frequently undesirable because this vacuum could suction gas out of an apparatus, which is connected to the feed line. In case the apparatus is a medical apparatus and is connected to a patient, then the patient could be put at risk due to a vacuum. Such a vacuum can arise, for example, when gas is actively being suctioned from the discharge line and the filter unit and/or the feed line are clogged or the feed line does not correctly connect an apparatus to the filter unit (misconnection).

Analogous to the pressure relief valve, in one embodiment the vacuum threshold is predefined by the structure of the vacuum valve. In another embodiment, a control device or a comparator causes the vacuum valve to open when the vacuum has dropped below the vacuum threshold. In a third embodiment, in case of a vacuum below the vacuum threshold, a message is outputted in a form perceptible by a person. The embodiments, that a control device automatically opens the vacuum valve and that a message is outputted, can be combined with one another.

In one embodiment, at least one opening is formed in a wall of the filter unit, preferably a plurality of openings. A fluid connection can be established through these openings between the interior of the filter unit and the surrounding area, so that gas can flow from the surrounding area through the vacuum valve and the opening or openings into the interior of the filter unit. The closed vacuum valve or a closed vacuum valve closes this opening or openings in the case of a vacuum lower than the vacuum threshold and interrupts the fluid connection between the interior of the filter unit and the surrounding area. The openings limit the flow of gas into the filter unit.

In a variant of this embodiment, a vacuum valve is formed in a wall of the buffer storage device or in a wall of the feed line. In case of a vacuum in the buffer storage device, which is below the vacuum threshold, gas flows from the surrounding area into the buffer storage device. This embodiment reduces the risk that a too high vacuum in the buffer storage device suctions gas out of the feed line or that the buffer storage device is damaged because of a too high vacuum.

In a preferred embodiment of the embodiment that the filter unit comprises a filter mount, the filter mount comprises a pot or is configured as a pot. A filter can be inserted from above into this pot and can again be removed from the pot. This pot can preferably be closed in a fluid-tight manner with a cover, and the cover can again be removed, for example, in order to replace the filter. When the gas to be filtered is heavier than air, it sinks downwards in this pot, and no relevant quantity can escape directly into the surrounding area. Even if no filter is currently inserted into the pot-shaped filter mount, for example, while the filter is being replaced, only relatively little released gas reaches the surrounding area, even if the pot is not closed, but rather is open to the surrounding area, especially while the filter is being replaced. This embodiment saves time during the replacement of the filter.

According to the present invention, the filter unit is in at least one fluid connection with the feed line. In one embodiment, a section of this feed line is passed through the interior of the filter unit. This section is preferably located between a wall of the filter unit and the filter inserted into the filter mount. In case the filter unit comprises a filter mount, a section of the feed line is preferably passed through the interior of the filter mount and is located between the filter and the wall of the filter mount when the filter has been inserted. An outlet opening in this section of the feed line determines at what point gas is released from the feed line and enters the filter mount and thus the filter. This outlet opening may be located close to a bottom of the filter unit, especially close to the filter mount. This embodiment is especially advantageous when the gas, out of which the gas component or at least one gas component shall be filtered, is heavier than air, which is especially the case in a gas mixture with anesthetic. The outlet opening may also be positioned in the vicinity of the upper closure of the filter unit. It is also possible that a first outlet opening leads to the filter and a second outlet opening leads to a buffer storage device in the filter mount. Depending on whether or not a filter has been inserted, the one outlet opening is open and the another outlet opening is closed or vice versa.

The discharge line may also comprise a section that is arranged in the interior of the filter unit and is located between a wall of the filter unit and an inserted filter. In case the filter unit comprises a filter mount, this section of the discharge line is preferably located between the filter and a wall of the filter unit. This section may have an inlet opening, optionally at least two inlet openings.

This embodiment can be combined with the embodiment described above, in which a cavity occurs between the filter mount and the filter and belongs to the buffer storage device. The section of the feed line and the section of the discharge line in the filter mount are preferably separated from the buffer storage device in the filter mount in a fluid-tight manner.

It is possible that a gas reaches the taking up/receiving system according to the present invention exclusively due to the fact that it is fed into the feed line, for example, is discharged from an apparatus, which is connected to the feed line. In another embodiment, in addition to or instead of this, gas is suctioned out of the discharge line. According to one embodiment of this other embodiment, the taking up/receiving system comprises, furthermore, a vacuum generator, especially a suction pump, which is preferably arranged at the discharge line or downstream of the discharge line. The vacuum generator is in a fluid connection with the discharge line and generates a vacuum in the discharge line. This vacuum in the discharge line suctions a gas. The suctioned gas is suctioned out of an apparatus connected to the feed line, and especially from a medical apparatus, through the feed line, the filter unit and the discharge line. At least one fluid connection preferably connects the buffer storage device or a buffer storage device to the discharge line. The vacuum, which the vacuum generator generates, empties the buffer storage device through this fluid connection, even if currently no gas or only a little gas is being released from the medical apparatus.

In an already described embodiment, the filter unit comprises a filter mount and a filter. The filter mount is in a respective fluid connection with the feed line and with the discharge line. The filter can be inserted into the fluid taking up/receiving unit and again be removed from the filter mount, for example, in order to replace it with a new filter. The just described embodiment with the vacuum generator gains an additional advantage when it is embodied in combination with a filter mount and with a filter. During the replacement of the filter, the filter mount is in many embodiments at least partially in a fluid connection with the surrounding area. The vacuum generator suctions gas out of the filter mount even if no filter has been inserted. As a result, the vacuum generator reduces the quantity of gas, which is released from the filter mount into the surrounding area.

The vacuum generator is also advantageous when the buffer storage device or at least one buffer storage device is continuously or at least from time to time in a fluid connection with the surrounding area, for example, in order to release an overpressure. The vacuum generator releases an overpressure and reduces the risk that a large quantity of gas will be released into the surrounding area.

In one variant, the vacuum generator is in a fluid connection with the feed line of the taking up/receiving system. The filter unit and/or at least one buffer storage device are arranged downstream of the vacuum generator. This embodiment makes it easy to overcome a pneumatic resistance of the filter of the filter unit.

It is possible that gas suctioned by the vacuum generator is suctioned through the feed line into the fluid taking up/receiving unit described above and from there further into the discharge line. The discharge line and the fluid taking up/receiving unit prevent a large quantity of the gas component from being released into the surrounding area even if no filter has been inserted into the filter mount. Therefore, this effect is, above all, generated because the vacuum, which the vacuum generator brings about, suctions gas from the buffer storage device and as a result prevents this gas from being released into the surrounding area.

An additional effect of the vacuum generator is as follows: The generated vacuum overcomes a pneumatic resistance of the filter of the taking up/receiving system and reduces the risk that a backup occurs upstream of the filter.

In one variant of this embodiment, a control device of the taking up/receiving system actuates an adjusting element of the vacuum generator and causes the vacuum generator to achieve a desired volume flow in the discharge line. A sensor measures the actual volume flow, and the control device receives measured values from this sensor for the actual volume flow and actuates the adjusting element such that the difference between the desired volume flow and the actual volume flow is reduced, regulated or controlled, i.e., the volume flow in the discharge line.

The vacuum generator preferably comprises a suction pump. Instead of a suction pump, another vacuum generator may also be in a fluid connection with the discharge line, for example, an ejector system.

The gas is preferably sent forcibly on a predefined path through the filter unit, i.e., the gas is forced, on its path from the feed line to the discharge line. This force causes all the gas to flow through the filter and no gas flows past the filter. As a result, the risk that undesirable gas reaches the fluid taking up/receiving unit is reduced.

In addition, the gas is preferably forced through the filter. In one embodiment, a wall divides the filter into at least two areas. This wall preferably extends parallel to or obliquely to a direction, in which gas flows through the filter. The first area of the filter is in a fluid connection with the feed line, and the second area of the filter is in a fluid connection with the discharge line. The filter is configured such that the gas flows through the feed line, then through the first area, then through the second area and then into the discharge line. In this embodiment, the gas is filtered twice, namely once in the first area and once in the second area. Even if one area has become clogged and a lesser filtering action or even no filtering action is achieved, the other area is stilled filtered in many cases. Therefore, this embodiment increases the reliability.

The taking up/receiving system preferably comprises at least one nonreturn valve. This nonreturn valve is arranged, for example, in the discharge line or in the feed line. It makes possible a flow in the direction from the feed line through the discharge line and prevents a flow in the opposite direction. When the discharge line is connected to a fluid taking up/receiving unit, this nonreturn valve prevents fluid from reaching an apparatus that is connected to the feed line, from the fluid taking up/receiving unit through the discharge line and through the feed line. Such a backflow may damage the apparatus or—in case of a medical apparatus or in case of a patient connected to the apparatus—may put the patient at risk. The taking up/receiving system may also comprise a plurality of nonreturn valves, for example, one in the feed line and one in the discharge line.

The filter of the filter unit is capable of taking up/receiving only a maximum quantity of the gas component or each gas component to be filtered out, as a rule, and is then spent. After the taking up/receiving of this maximum quantity, the filter unit must be replaced. This maximum quantity is predefined, for example, by a manufacturer of the filter unit, or can be calculated beforehand. It is possible, in addition, in some embodiments of the filter that the filter swells up because of liquid and for this reason is no longer capable of taking up/receiving additional quantity of a gas component and therefore has to be replaced.

In one embodiment, the taking up/receiving system comprises a component sensor for the gas component or at least one gas component to be filtered out, especially an anesthetic sensor. This sensor measures at one measurement position downstream of the filter an indicator of the quantity or concentration of the gas component in the gas flowing past. If this indicator exceeds a predefined component threshold, then the component sensor triggers the output of an alarm. A quantity or concentration above the anesthetic threshold indicates that the filter is no longer sufficiently capable of filtering the gas component out of the gas stream that is flowing through. In one embodiment, this alarm is outputted in a form perceptible by a person at a location that is arranged at a distance in space, for example, in a center. It is possible that the taking up/receiving system has different component sensors for different gas components.

In a preferred embodiment, this sensor comprises a sensor or another transducer, which is arranged in the interior of the filter mount of the filter unit. In case the gas component to be filtered out is heavier than air and therefore sinks downwards, the transducer is preferably located below the filter in the filter mount. In another embodiment, this sensor is arranged downstream of the filter unit. This transducer is positioned downstream of the filter in both embodiments and measures the concentration of at least one gas component to be filtered out in the gas flowing past. In case the filter is no longer capable of filtering a sufficient quantity of the gas component out of the gas stream flowing through, the sensor therefore records an increased concentration of the gas component which is to be filtered out, but which is actually not being filtered out.

A possible embodiment of the filter unit with the filter mount was already described further above, namely that an pressure relief valve in the interior of the filter mount opens, when the pressure in the interior of the filter mount exceeds a predefined overpressure threshold. When the pressure relief valve is open, in one embodiment, at least some of the gas, which reaches the filter mount, is passed around the filter in the filter mount. In this situation, the sensor with the transducer in the interior of the filter mount measures an increased concentration of the gas component to be filtered out. The sensor detects this increased concentration both when an overpressure has occurred and when the pressure relief valve has opened and hence the gas flows around the filter in the filter mount and when the pressure relief valve has closed and even though the gas flows through the filter, the filter is no longer sufficiently capable of filtering out the gas component.

In one embodiment, an alarm is outputted if at least one of the following situations has occurred:
  The just described sensor measures an increased concentration of the gas component in the interior of the filter mount.
  An pressure relief valve has opened or was opened at the feed line, at the filter unit, at the discharge line or at the buffer storage device or at a buffer storage device.
  A vacuum valve has opened or was opened at the feed line, at the filter unit, at the discharge line or at the buffer storage device or at a buffer storage device.

This embodiment ensures that an alarm is outputted both when the filter is spent, because it has taken up/received a high quantity of the gas component, and when the filter has become clogged for another reason, for example, is plugged or inserted incorrectly, or a packaging was not removed. In many cases, an alarm is outputted even if a plugging has occurred upstream of the filter.

In another embodiment, the taking up/receiving system comprises a component quantity determination device. This component quantity determination device determines approximately an indicator of the quantity of the predefined gas component, especially anesthetic that the filter has taken up/received so far. "So far" preferably means: Since the time, at which the use of the currently used filter in the filter unit has been begun. The component quantity determination device may be arranged in the interior of an apparatus, which is connected to the feed line, or be implemented on a computer, for example, on a smartphone. In order to determine this quantity approximately, the component quantity determination device in one embodiment receives and uses
  on the one hand, a signal for the time-variable volume flow of gas through the feed line towards the filter unit and,
  on the other hand, a signal for the time-variable concentration of the gas component or of at least one gas component in the feed line.

In another embodiment, the component quantity determination device receives a signal for the feeding of the gas component into the feed line. For example, an indicator of the quantity of anesthetic that is added to a carrier gas is measured.

The component quantity determination device receives these signals in a wired manner or via radio waves. The component quantity determination device approximately calculates the quantity that has been taken up/received so far by the filter from these two signals. The product of the gas volume flow and the concentration yields the volume flow of the gas component. In the case of a time-variable concentration, numerical integration is performed via this product.

This embodiment spares the need to provide a sensor downstream of the filter unit. An apparatus, which can be connected to the feed line, frequently already comprises a sensor for the volume flow. The concentration of the gas component can in some cases be measured by an additional sensor of this apparatus or is set at the apparatus. The component quantity determination device is at least from time to time in a wired or wireless (via radio waves) data connection with these two sensors.

In one embodiment, the information about what quantity of the gas component the filter of the filter unit has taken up/received so far is stored in a memory. If it is possible that the filter takes up/receives different gas components, then in a variant of this embodiment a respective identifier of this gas component as well as information about what quantity of this gas component the filter has taken up/received so far will be written on the data storage medium for each possible gas component that the filter can take up/receive.

The data storage medium may be a component of the filter unit and be fastened, for example, to the filter unit. A memory, which belongs to the filter unit, is preferably configured as an RFID chip, it may also be configured as a barcode. The memory may be arranged separated in space from the filter unit. The quantity taken up/received so far may be measured by a sensor of the filter unit or may have been determined approximately by the just described component quantity determination device. This information about the stored quantity can preferably be determined and read out from the remote location and compared with a predefined determination, wherein the determination predefines what maximum quantity the filter is capable of taking up/receiving. This embodiment makes it possible to provide a new filter or a new filter unit with a filter in a timely manner. In addition, the embodiment with the memory for the taken up/received quantities makes it easy to process the spent filter and/or to obtain materials from the filter. Information which is stored in the memory can be used to adapt the treatment to the gas components and/or gas quantities taken up/received by the filter.

It is possible that the same filter is capable of taking up/receiving different gas components over the course of a use. Respective information about the maximum possible quantity is preferably stored in the memory for each gas component. The quantity, which the filter has taken up/received so far, is compared with the maximum possible quantity, which is stored in the memory, for each gas component.

The gas component or a gas component, which the filter is capable of filtering out of a gas flowing through, is an anesthetic in one embodiment. In another embodiment, the component is a gas that is flammable and/or is harmful to a person. The gas component may also be a quantity of particles which are contained or may be contained in the gas, for example, dust or microbes or viruses or other pathogens that may be in the air. It is possible that the filter is capable of filtering a plurality of gas components, for example, a plurality of different anesthetics and/or at least one anesthetic as well as particles, out of a gas flowing through.

The present invention pertains, furthermore, to a medical device that comprises at least one medical apparatus as well as an taking up/receiving system according to the present invention. A medical apparatus or the medical apparatus is especially an anesthesia apparatus. The feed line of the taking up/receiving system is in a fluid connection with the medical apparatus or with a medical apparatus at least from time to time. This fluid connection can preferably be established and later be severed again. As a result, the same taking up/receiving system can be connected to different medical apparatuses one after the other, and the same medical apparatus can be connected to different taking up/receiving systems one after the other.

In one embodiment, the taking up/receiving system according to the present invention is separated in space from the medical apparatus. The feed line of the taking up/receiving system is in a fluid connection with the medical apparatus. The taking up/receiving system can preferably be connected to different medical apparatuses one after the other. The taking up/receiving system according to the present invention is in another embodiment a component of the medical apparatus and is arranged in the interior of the medical apparatus. The discharge line preferably provides a coupling point for fluid, which the medical apparatus has discharged and/or which is suctioned.

In one embodiment, the medical device comprises a first medical apparatus and a second medical apparatus. A fluid connection can be selectively or simultaneously established between the feed line and the first medical apparatus and/or between the feed line and the second medical apparatus. This embodiment spares the need to provide a respective separate taking up/receiving system with a filter unit for both medical apparatuses.

In case the two medical apparatuses are simultaneously connected to the taking up/receiving system, then the volume flow and/or pressure in the feed line varies in some cases less widely than if the taking up/receiving system were only connected to a single medical apparatus.

It is also possible that the taking up/receiving system according to the present invention is selectively or even simultaneously in a respective fluid connection with three or even more medical apparatuses.

According to the present invention, the discharge line can be connected to a fluid taking up/receiving unit, which is a stationary fluid taking up/receiving unit in one embodiment. This stationary fluid taking up/receiving unit preferably belongs to a medical infrastructure system, and in particular to a stationary infrastructure system in a hospital. This medical infrastructure system is also capable of providing the required gases and other fluids for the medical apparatus. Optionally, a vacuum generator, for example, a suction pump, of the fluid taking up/receiving unit is at least from time to time in a fluid connection with the discharge line and is capable of suctioning gas.

The present invention pertains, furthermore, to a medical system, the medical system comprising a medical device with at least one medical apparatus and with an taking up/receiving system according to the present invention as well as a fluid taking up/receiving unit. The discharge line of the taking up/receiving system is in a fluid connection with the fluid taking up/receiving unit at least from time to time.

The medical system comprises at least one additional fluid taking up/receiving unit in one variant of this embodiment. The two fluid taking up/receiving units of the medical system are especially preferably stationary fluid taking up/receiving units. Fluid connection can be selectively or simultaneously established between the fluid taking up/receiving unit and the discharge line or between the additional fluid taking up/receiving unit and the discharge line. It is also possible that the medical system comprises three or even more fluid taking up/receiving units, wherein the discharge line is selectively or simultaneously in a respective fluid connection with the at least three fluid taking up/receiving units.

The embodiment with at least two fluid taking up/receiving units makes it possible to take up/receive an especially large quantity of gas from the medical apparatus. It is also possible to divert a gas, which the medical apparatus discharges or which is suctioned, selectively into the one fluid taking up/receiving unit or into the other fluid taking up/receiving unit, which is sometimes especially advantageous when the medical apparatus discharges different gases one after the other, for example, gases containing different anesthetics.

In another application, the taking up/receiving system is used to purify the air in an area, for example, in a closed space in a building or in a vehicle, from microbes, other pathogens or particles. The taking up/receiving system preferably comprises a conveyor unit or is in a fluid connection with a conveyor unit. This conveyor unit conveys the air to be purified from the space through the feed line, the filter unit and the discharge line back into the space.

The present invention will be described below on the basis of an exemplary embodiment. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIGS. 8a, 8b, 8c, 8d, 8e, 8f, and 8g are schematic views showing different possible embodiments of the pressure relief valve from FIG. 5 through FIG. 7;

FIGS. 12a, 12b, 12c, 12d, 12e, 12f, and 12g are schematic views showing different possible embodiments of the vacuum valve from FIG. 11;

FIGS. 13a, 13b, and 13c are schematic views showing different possible embodiments of an elastic buffer storage device in the feed line;

FIGS. 27a and 27b are schematic views showing an embodiment, in which two medical apparatuses are connected to the same taking up/receiving system according to the present invention; and FIGS. 28a and 28b are schematic views showing an embodiment, in which two stationary gas taking up/receiving units are connected to the same taking up/receiving system according to the present invention.

DESCRIPTION OF PREFERRED EMBODIMENTS

In the exemplary embodiments, the present invention is used to mechanically ventilate a patient and to feed to the patient at least one anesthetic in this case. The patient is located in an enclosed space, while the patient is being mechanically ventilated, for example, in a room of a hospital or onboard a vehicle.

Figure 1:
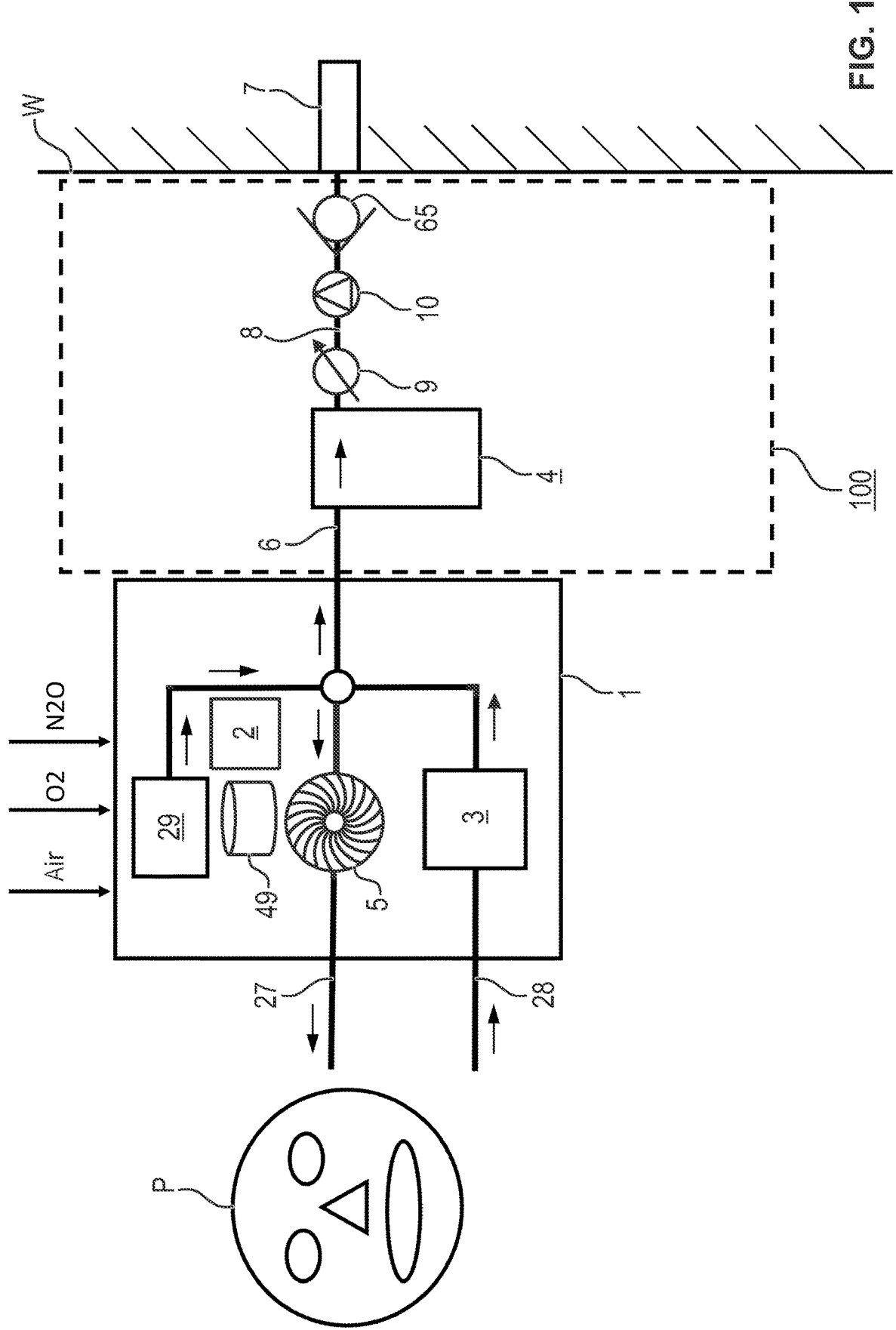
FIG. 1 is a schematic view showing a medical device with an anesthesia apparatus and with an taking up/receiving system according to the present invention.
Figure 2:
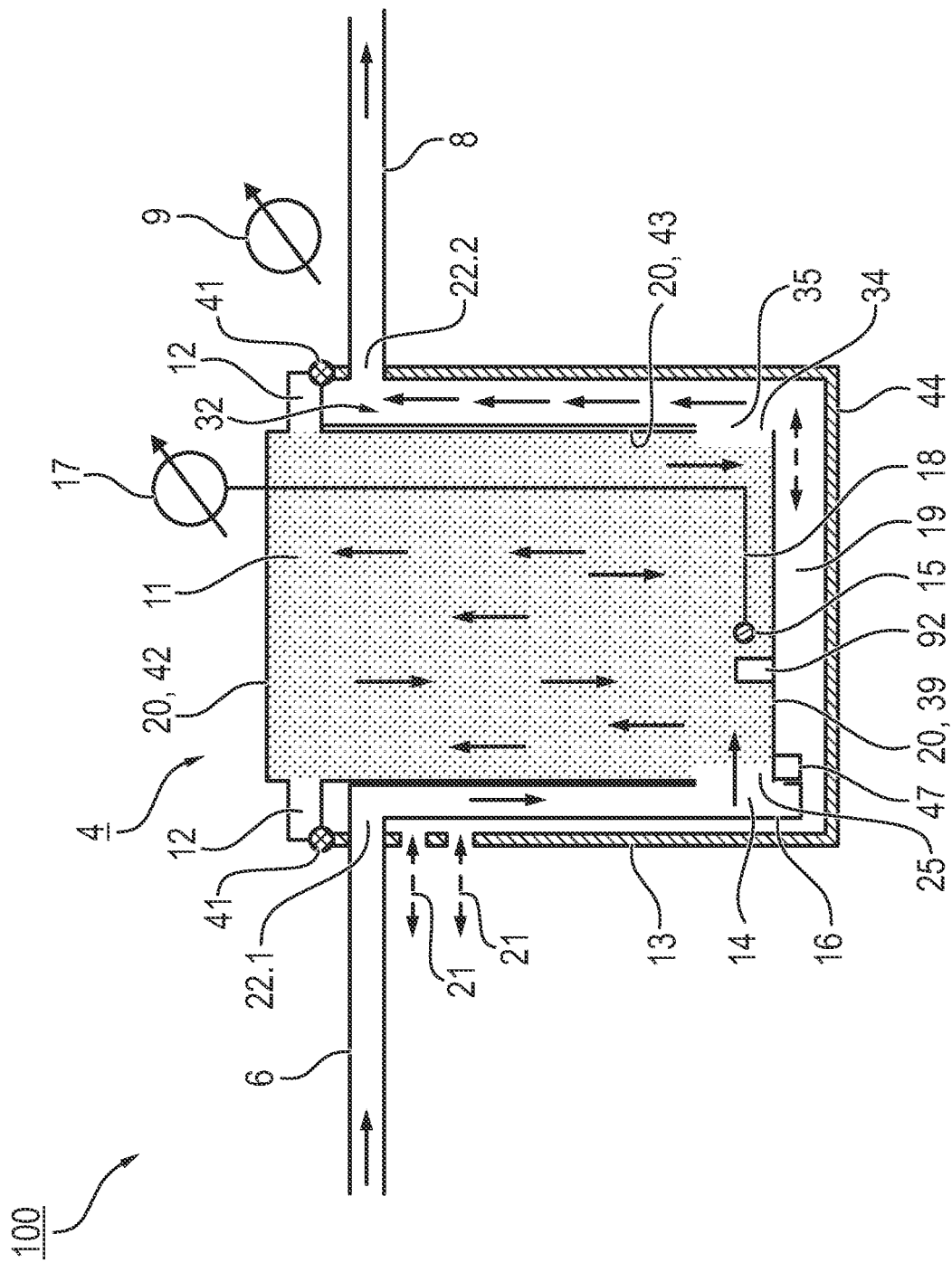
FIG. 2 is a schematic view showing an embodiment with a pneumatically acting buffer storage device in the interior of the filter mount and around the filter, wherein a cartridge with a filter is inserted.

Referring to the drawings, FIG. 1 shows a medical device for anesthetizing this patient P and for mechanically ventilating the patient. The patient P is supplied with breathing air via an inhalation gas line 27. This breathing air is mixed with at least one anesthetic in order to keep the patient P anesthetized. The breathing air exhaled by the patient P contains carbon dioxide ($CO_2$) and is suctioned off via an exhalation gas line 28. Both gas lines 27, 28 are connected to a medical apparatus in the form of an anesthesia apparatus 1, which maintains a ventilation circuit, in order to supply the patient P with breathing air and anesthetic and to suction off and take up/receive exhaled air.

The anesthesia apparatus 1 is supplied with pressurized breathing air, pure oxygen ($O_2$) and nitrous oxide ($N_2O$) from a hospital infrastructure. The anesthesia apparatus 1 comprises the following components in the exemplary embodiment:

a mixer 29 which generates a mixture consisting of two of the three gases being fed (air, $O_2$ and $N_2O$), which is used as a carrier gas for anesthetic, wherein the mixer 29 may be configured as described in DE 10 2008 057 180 B3 (corresponding to U.S. Pat. No. 8,356,596 (B2), the entire contents of which are incorporated herein by reference), a ventilator unit 5 which moves gas in the ventilation circuit and maintains the ventilation circuit as a result, an anesthetic vaporizer 2, which comprises a tank 49 for liquid anesthetic, and an internal filter unit 3 with a lime filter, which filters $CO_2$ out of the breathing air exhaled by the patient P and diverted via the exhalation gas line 28.

The anesthetic vaporizer 2 adds anesthetic from the tank 49 to the carrier gas. For example, the anesthetic vaporizer 2 vaporizes the anesthetic in the tank 49 and/or injects it into the carrier gas.

The anesthesia apparatus 1 feeds gas to the ventilation circuit. The filter unit 3 extracts gas, and especially $CO_2$, from the ventilation circuit. In balance, more gas is fed to the ventilation circuit than is removed as a result. Therefore, it is necessary to discharge excess gas from the ventilation circuit. This excess gas, called "excess gas" below, is removed from the anesthesia apparatus 1 by means of two gas lines 6 and 8, namely by means of a feed line 6 and a discharge line 8. On the one hand, the ventilator unit 5 discharges gas and feeds the discharged excess gas into the feed line 6, wherein the volume flow of the discharged excess gas varies over time and the time curve of the volume flow has, for example, the shape of a half sine curve. On the other hand, the discharged excess gas is sent through the discharge line 8 and is suctioned in one embodiment.

In the exemplary embodiment, the discharge line 8 leads into a stationary fluid taking up/receiving unit 7, which is formed in a wall W. The fluid taking up/receiving unit 7 is preferably a component of a stationary infrastructure of a hospital, which takes up/receives and forwards gas that is discharged by different medical apparatuses.

A nonreturn valve 65, which lets gas pass from the discharge line 8 in the direction of the fluid taking up/receiving unit 7, but prevents gas from flowing from the fluid taking up/receiving unit 7 backwards through the discharge line 8, is preferably formed in the discharge line 8. In an alternative embodiment, the nonreturn valve 64 is integrated into the fluid taking up/receiving unit 7. It is also possible that the nonreturn valve 65 or a nonreturn valve 65 is positioned in the feed line 6 or in the connection between the feed line 6 and the anesthesia apparatus 1. In all possible positions, the nonreturn valve 65 makes it possible for the anesthesia apparatus 1 to discharge gas, but prevents a backflow from acting on the anesthesia apparatus 1 and thus on the patient P.

The medical device comprises, furthermore, an taking up/receiving system 100 according to the present invention with a filter unit 4 as well as with the lines 6 and 8. The filter unit 4 comprises a filter 11, 20 as well as a pot 13, which functions as a filter mount. These components are described in detail below.

In the embodiment, which is shown in FIG. 1, the feed line 6 is located partially outside of the anesthesia apparatus 1. It is also possible that the feed line 6 is located entirely within the anesthesia apparatus 1 and the filter unit 4 is coupled detachably with the anesthesia apparatus 1. It is also possible that the taking up/receiving system 100 according to the present invention is located entirely within the anesthesia apparatus 1.

In one embodiment, the anesthesia apparatus 1 causes excess gas to be discharged through the lines 6 and 8 exclusively.

In another embodiment, a suction pump 10, which is in a fluid connection with the discharge line 8, suctions excess gas from the taking up/receiving system 100. This suction pump 10 can preferably be switched on and switched off and generates a volume flow away from the filter unit 4 and through the discharge line 8. In the embodiment shown, the suction pump 10 is positioned in front of the wall W and is in a fluid connection with the discharge line 8. In another embodiment, the suction pump 10 is located in or behind the wall W and is in a fluid connection with the fluid taking up/receiving unit 7 and is also indirectly in a fluid connection with the discharge line 8 via the fluid taking up/receiving unit 7.

In one embodiment of this suctioning, the volume flow, i.e., the volume, which flows through the discharge line 8 per time unit, is constant over time and follows a different predefined time curve. An optional volume flow sensor 9 measures the volume flow, i.e., the volume per time unit, in the discharge line 8. In one embodiment, the suction pump 10 is actuated as a function of measured values of the volume flow sensor 9, for example, by a control device of the taking up/receiving system 100, so that the actual volume flow through the discharge line 8 is equal to a desired predefined volume flow. Thus, the actual volume flow in the discharge line 8 is automatically regulated.

In another embodiment, a pressure sensor, not shown, measures the pressure at a measurement point in the discharge line or upstream of the discharge line 8, preferably also upstream of the filter unit 4 described below. As soon as the measured pressure exceeds a predefined pressure threshold, the suction pump 10 is activated and suctions excess gas into the discharge line 8. The suction pump 10 remains activated until the measured pressure again drops below the pressure threshold.

The excess gas which is discharged and suctioned from the anesthesia apparatus 1 may contain O2, N2O and/or anesthetic. Hence, this excess gas is sent to an taking up/receiving system 100 according to the present invention. This taking up/receiving system 100 is via the feed line 6 in a fluid-tight fluid connection with the anesthesia apparatus 1 and via the discharge line 8 in a fluid-tight fluid connection with a stationary fluid taking up/receiving unit in the form of a gas taking up/receiving unit 7. The gas taking up/receiving unit 7 is arranged at a wall W and partly behind this wall W and belongs to the hospital infrastructure. Both the connection between the anesthesia apparatus 1 and the feed line 6 and the connection between the discharge line 8 and the gas taking up/receiving unit can preferably be severed and later be established again.

The excess gas is sent through a filter unit 4. The feed line 6 leads from the anesthesia apparatus 1 to this filter unit 4. The discharge line 8 leads from the filter unit 4 to the gas taking up/receiving unit 7. The gas taking up/receiving unit 7 takes up/receives the filtered gas, which flows through the discharge line 8. The filter 11, 20 of the filter unit 4 filters undesirable components out of the excess gas, especially the anesthetic or each anesthetic. The taking up/receiving system 100 is preferably configured such that the excess gas is forced through the filter unit 4 and cannot bypass this filter unit 4.

Because the gas taking up/receiving unit 7 takes up/receives the filtered excess gas, after undesirable components have been filtered out of the excess gas, a relevant quantity of undesirable gas components, for example, of O2, N2O and/or anesthetics is in many cases prevented from entering into the hospital infrastructure or into a room of the hospital or into the surrounding area of the hospital. The first event (anesthetic in the hospital infrastructure or in a space) is undesirable, because released gas, especially an anesthetic, could put the health of people in the space at risk and O2 could additionally damage apparatuses. The second event is undesirable, because the environmental emissions should be kept low.

The feed line 6 connects the filter unit 4 to the medical apparatus 1 in the embodiments shown below. It is also possible that the filter unit 4 can be coupled directly detachably with the medical apparatus 1, for example, by means of two corresponding coupling elements. This embodiment spares a feed line 6 outside of the medical apparatus 1.

In the embodiments described below, the filter unit 4 comprises a filter mount in the form of a pot 13 which is rotationally symmetrical to a central axis, wherein this central axis is arranged vertically during the use. An approximately cylindrical filter can be inserted in this pot 13 from above and again be removed from the pot 13. Optionally, a cover 42 can be placed onto the pot 13 from above and again removed. Furthermore, the filter 11, 20 belongs to the filter unit 4.

In one embodiment, the pot 13 comprises a filter sensor 47, which determines whether or not a filter 11, 20 has been inserted into the pot 13. For example, a contact switch of the filter sensor 47 closes an electrical circuit, when a filter 11, 20 has been inserted, or interrupts such a circuit when a filter 11, 20 has been inserted. Or the inserted filter 11, 20 interrupts a light barrier. This embodiment makes it possible to generate an alarm and to output same in a form perceptible by a person, when no filter 11, 20 has been inserted into the pot 13 for a period which is longer than a predefined time period threshold. In a variant of this embodiment, this warning is outputted only if it is additionally determined that a gas mixture flows through the feed line 6 and/or into the filter unit 4.

Figure 9:
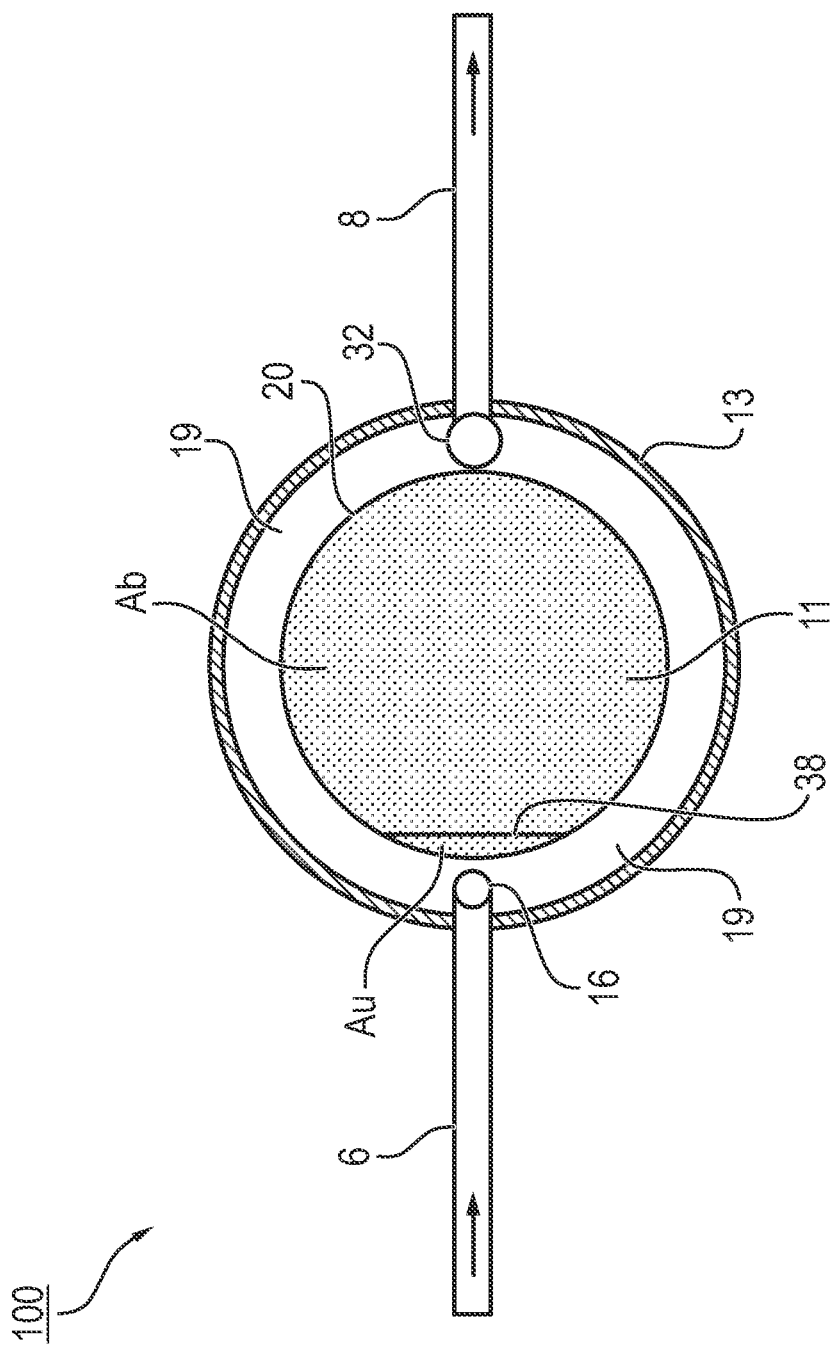
FIG. 9 is a schematic view showing a cross-sectional view of the embodiment from FIG. 4 through FIG. 7 in the plane A-A from FIG. 4 through FIG. 7.
Figure 10:
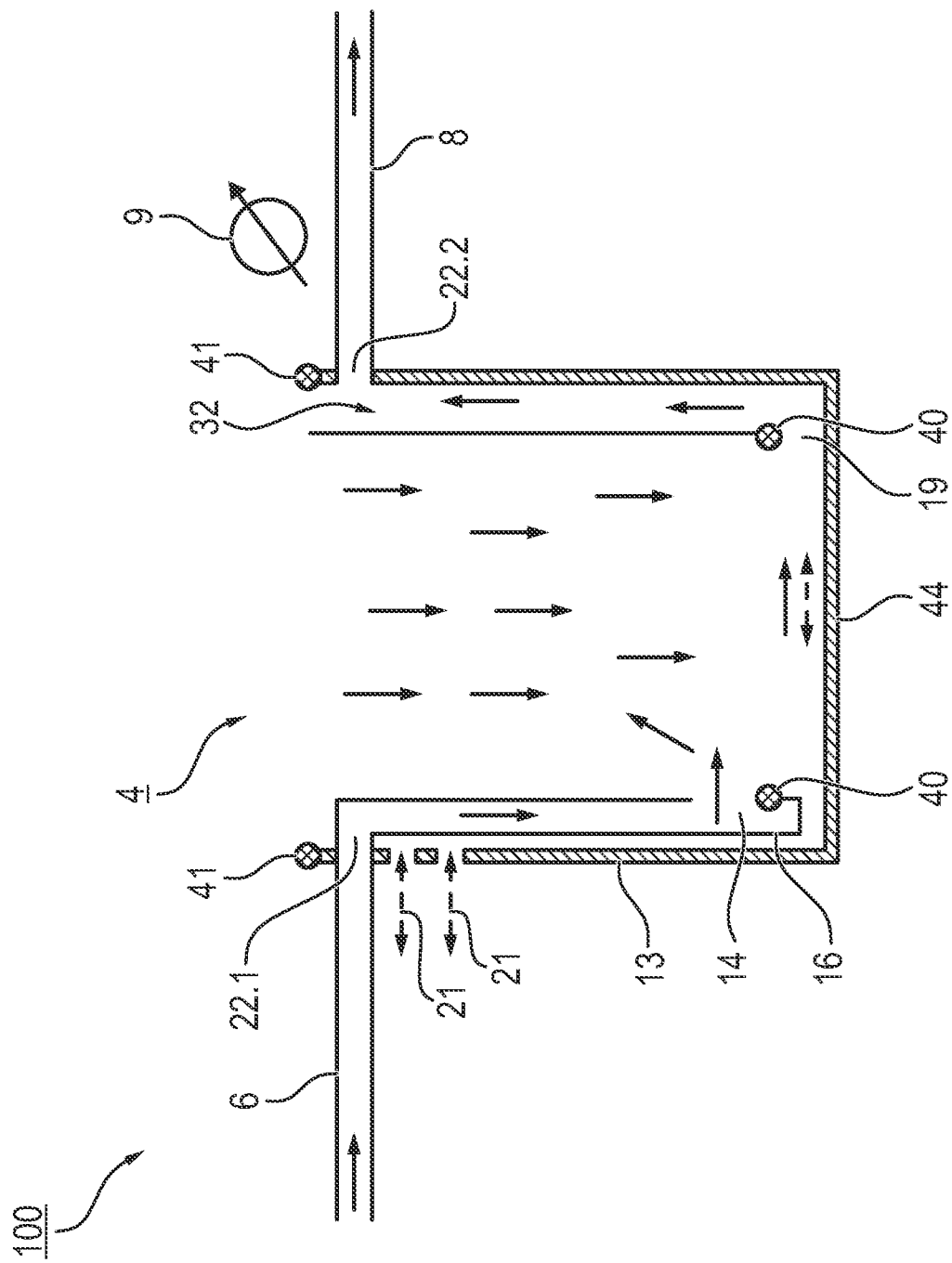
FIG. 10 is a schematic view showing the embodiment from FIG. 4, wherein the cartridge has been removed.

FIG. 2 through FIG. 17 show a plurality of possible embodiments of the taking up/receiving system 100, wherein a buffer storage device, which is described below, is arranged between a cartridge in the filter unit 4 and the pot 13. Identical reference numbers have the same meaning FIG. 2 through FIG. 7, FIG. 10, FIG. 11 and FIG. 14 through FIG. 17 show the filter unit 4 in a side view, wherein the central axis of the filter unit 4 lies in the drawing plane. FIG. 9 shows the filter unit 4 in a cross-sectional view in the plane A-A of FIG. 4 through FIG. 7, wherein the central axis of the cylindrical filter unit 4 is at right angles to the drawing plane of FIG. 9. FIG. 20 through FIG. 24 show different embodiments, wherein the buffer storage device is arranged outside of the pot 13 and wherein the filter unit 4 is likewise shown in a side view. It is also possible that the taking up/receiving system 100 has a buffer storage device in the pot 13 and a buffer storage device outside of the pot 13.

In the embodiments shown, the filter unit 4 comprises the actual filter 11 for anesthetic, which is called "filter element" or else "anesthetic filter" below,
- a cylindrical cartridge 20, which encloses the anesthetic filter 11, preferably entirely and in a gastight manner— except for openings described below,
- a circumferential projection 12 at the top of the cartridge 20,
- a cylindrical pot 13, which receives the cartridge 20 with the anesthetic filter 11 and has a bottom 44 as well as a lateral surface,
- a pot feed line 16, which is connected in a fluid-tight manner with the feed line 6, sends excess gas being fed from an opening 22.1 towards the bottom 44 of the pot 13 and ends in an outlet opening 14,
- a pot discharge line 32, which is connected in a fluid-tight manner to the discharge line 8, sends excess gas being released from the anesthetic filter 11 towards the discharge line 8, begins in an inlet opening 35 or at the bottom 39 of the cartridge 20 and leads to an opening 22.2,
- a sensor 15, which measures an indicator of the quantity of anesthetic below or in a lower area of the anesthetic filter 11,
- a consumption indicator 17, which especially indicates when the cartridge 20 with the anesthetic filter 11 has to be replaced, and
- a measurement line 18, which leads from the sensor 15 to the consumption indicator 17.

The component, which comprises the filter element 11 and the cartridge 20, is designated below in an abbreviated manner as "filter 11, 20" or else as "anesthetic filter 11, 20." In one embodiment, the filter element 11 and the cartridge 20 form a single component, which may only be replaced as a whole. It is also possible that the filter element 11 can be inserted into the cartridge 20 and can be removed again from the cartridge 20, so that the same cartridge 20 can be used for different filter elements 11 one after the other.

A filter element 11 for anesthetic preferably has the shape of a cylinder and is preferably configured as a rigid body, which especially preferably consists of activated carbon or contains activated carbon. The filter element 11 may also contain zeolite. The central axis of this cylinder is arranged vertically when the filter 11, 20 is inserted into the pot 13, and lies in the drawing planes of FIG. 2 through FIG. 7, FIG. 10, FIG. 11, FIG. 14 through FIG. 24 and FIG. 26 and is at right angles to the drawing plane of FIG. 9. The filter element is especially preferably configured as a monolith consisting of activated carbon with a plurality of parallel channels. A filter element 11 configured in this manner exerts a lower pneumatic resistance than other filters with comparable filter capacity and is lightweight. However, such a filter element 11 is sensitive to mechanical effects and may break especially relatively easily. Such a filter element made of activated carbon and channels may be provided as described, for example, in DE 10 2015 012 410 A1.

The cartridge 20 protects the filter element 11 against mechanical damage up to a certain extent. The cartridge 20 preferably likewise has the shape of a cylinder, the central axis of which preferably coincides with the central axis of the filter element 11, and has a cover 42, a bottom 39 and a lateral surface 43, which extends between the cover 42 and the bottom 39. The cover 42 and the lateral surface 43 are impermeable to fluids—except for optional openings, which will be described further below. The bottom 39 is likewise impermeable to fluid in one embodiment and permeable to fluid in another embodiment. The cartridge 20 is preferably made of a hard plastic or made of metal. At least one guide element (not shown), which corresponds with a corresponds with a corresponding guide element on the inside at the wall of the pot 13, is preferably arranged on the outside at the cartridge 20. These two corresponding guide elements ensure that a filter 11, 20 is inserted into the pot 13 correctly (in a correct rotary position).

In one embodiment, the filter 11, 20 comprises a memory 92, which is preferably fastened to the cartridge 20 on the outside and is configured, for example, as an RFID chip or as a barcode. Information about the filter 11, 20 is stored on this memory 92. A reader, not shown, of the taking up/receiving system 100 is capable of reading out this information. In a preferred embodiment, this reader is a reader and writer, i.e., it is capable of also writing information into the memory 92.

A unique identifier of the filter 11, 20 is preferably stored in the memory 92. This identifier distinguishes this filter 11, 20 from all other filters that are used in the hospital. In one embodiment, the reader inputs this unique identifier, and which filter 11, 20 is currently in a fluid connection with which anesthesia apparatus or with another medical apparatus of the hospital is stored in a central memory (not shown). This information is updated as needed.

As a rule, the filter 11, 20 should or may be used only in a single taking up/receiving system 100 until it is spent, and may not be used again after that, or only after a treatment. An undesirable re-use can be prevented, for example, by means of an analysis of the just described memory 92. By contrast, in a preferred embodiment, the memory 92 contains the information, for example, in the form of a flag, whether or not this memory 92 and thus the filter 11, 20, to which this memory 92 is fastened, was inserted into an taking up/receiving system 100. The memory 92 of a new filter 11, 20 contains the information that the filter 11, 20 was still not inserted. The reader and writer reads out this information after insertion of a filter 11, 20. In case the filter 11, 20 was already inserted earlier into an taking up/receiving system 100, then the reader and writer generates a corresponding message. Otherwise, it stores the information that the filter 11, 20 was henceforth inserted into an taking up/receiving system 100 in the memory 92. The reader and writer preferably generates an error message, in case it does not find memory 92 or cannot read out the memory 92 after insertion of a filter 11, 20. In case of a barcode, the reader inputs, for example, the unique identifier of the filter 11, 20 and subsequently makes the barcode 92 illegible, for example, by spraying on a liquid or by painting over it or pasting over it.

In one embodiment, the information can be stored in the memory 92 and can be read out again, when a filter 11, 20 with this memory 92 was inserted into a pot 13 of an taking up/receiving system 100 for the first time. In case of a new filter 11, 20, no date of the insertion is stored. The reader and writer stores the date, and optionally the time, at which a filter 11, 20 was inserted into a pot 13. This information can be read out again later to determine how long der filter was already used in the pot 13. In some cases, a maximum duration of use of a filter 11, is predefined. In another embodiment, the barcode 92 contains the information when the filter 11, 20 was manufactured. The reader inputs this date of manufacture and then makes the barcode illegible.

The just described embodiment with the date of the insertion can also be used for preventing the same filter 11, 20 from being used several times in succession. In case the reader and writer detects an earlier date of the insertion in case of a just inserted filter already in the memory 92, then this filter 11, 20 was already used earlier, and the reader and writer generates a corresponding message. In case the barcode 92 is not legible, an error message is likewise outputted.

In one embodiment, the information, for which anesthetic the filter element 11 may be used, and/or the information, for which it may not be used, is stored in the memory 92. The reader reads out this information from the memory 92. The reader is preferably in a data connection with the anesthesia apparatus 1 and sends the information about the approved and/or prohibited anesthetic of the currently used filter element 11 to the anesthesia apparatus 1. For example, information, which anesthetics are currently being used, is stored in an internal memory of the anesthesia apparatus 1 because of a user input. The anesthesia apparatus 1 automatically checks whether or not the filter element 11 is approved for the currently used anesthetic or for each currently used anesthetic. In case of a prohibited filter element 11, the anesthesia apparatus 1 generates a corresponding error message in a form perceptible by a person.

The pot 13 is connected in a fluid-tight manner to the feed line 6 and to the discharge line 8. The material, from which the walls of the pot 13 are manufactured, is impermeable to fluid and is not attacked chemically by an anesthetic. The walls of the pot 13 are preferably made of a hard plastic or made of metal.

When the cartridge 20 is inserted correctly and especially in the correct rotary position into the pot 13, then the outlet opening 14 of the pot feed line 16 overlaps an inlet opening 25 in the cartridge 20 in one embodiment. The inlet opening 35 overlaps an outlet opening 34 in the cartridge 20. The two openings 14, 35 are located close to the bottom 44 of the pot 13, the two openings 25, 34 are located in the lateral surface 43 and close to the bottom 39 of the cartridge 20. Excess gas can flow into the filter element 11 through the inlet opening 25 in the cartridge 20 and can again flow out of the filter element 11 through the outlet opening 34 in the cartridge 20. The anesthetic filter 11, 20 brings about a forced guiding of gas, which flows through the anesthetic filter 11, 20, so that the excess gas flows through the anesthetic filter 11, via a relatively long path from the inlet opening 25 to the outlet opening 34.

Figure 5:
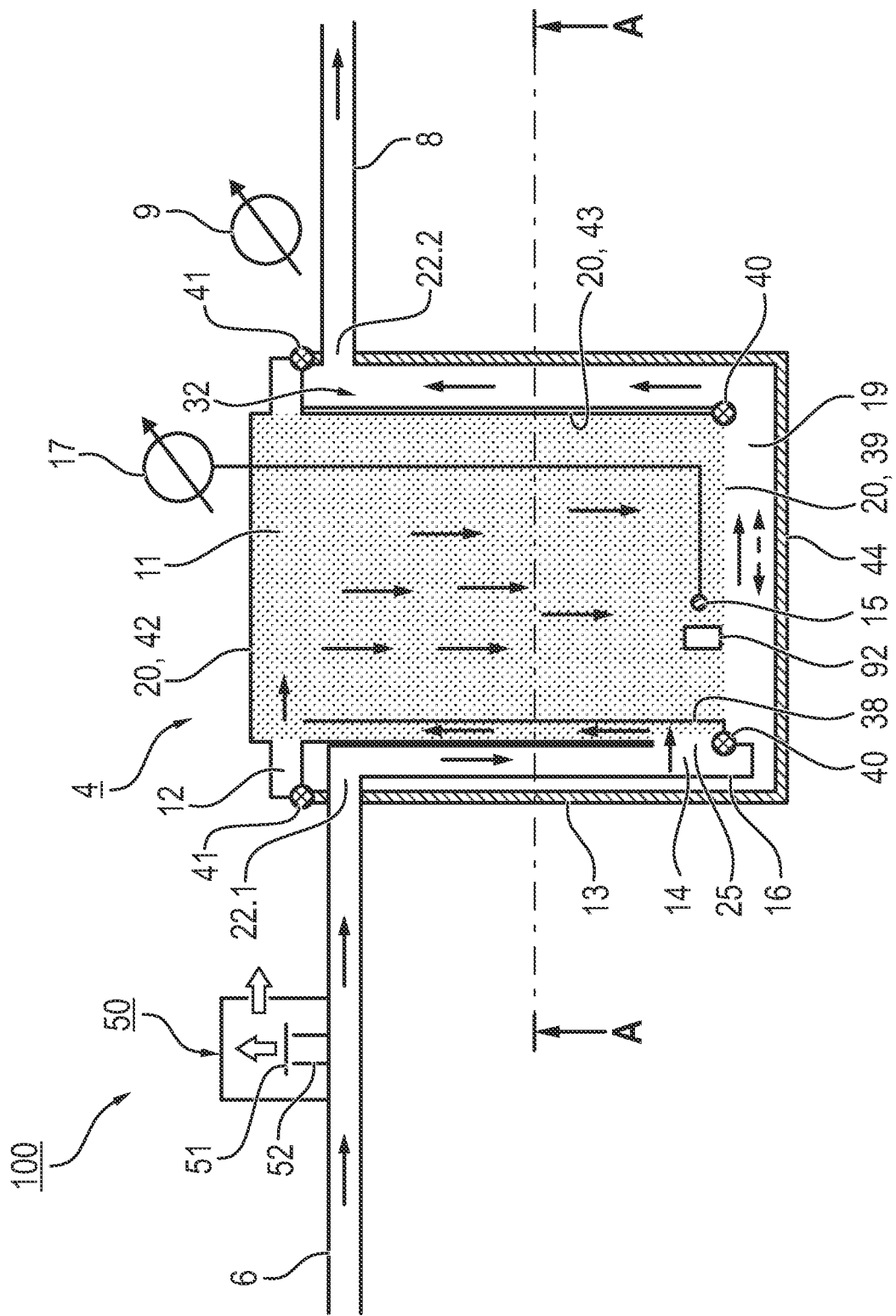
FIG. 5 is a schematic view showing a variant of the embodiment from FIG. 4, wherein an pressure relief valve, which releases gas into the surrounding area in case of overpressure, is arranged in the feed line.

In one embodiment which is shown in FIG. 5, an pressure relief valve 50 is arranged at the feed line 6, and the pressure relief valve 50 being in a fluid connection with the feed line 6. The pressure relief valve 50 is thus located upstream of the filter unit 4. The pressure relief valve 50 is closed or opened as a function of the difference between the pressure in the feed line 6 and the pressure in the area surrounding the feed line 6. This pressure relief valve 50 is closed as long as the pressure difference is below a predefined overpressure threshold. As soon as the pressure difference reaches or exceeds the predefined overpressure threshold, the pressure relief valve 50 opens automatically or is opened and establishes a fluid connection between the feed line 6 and the surrounding area. Excess gas may escape into the surrounding area. The pressure relief valve 50 preferably closes automatically again or is closed as soon as the pressure difference is again below the overpressure threshold.

In a simple mechanical embodiment, the pressure relief valve 50 comprises a valve plate 51, which is located on a valve crater 52, which is open upwards. The ratio between the weight of the valve plate 51 and the area of the upper opening of the valve crater 52 determines the overpressure threshold achieved. A gas pressure above the overpressure threshold raises the valve plate 51 from the valve crater 52, so that the gas can escape. Gravity lowers the valve plate 51 again.

Figure 6:
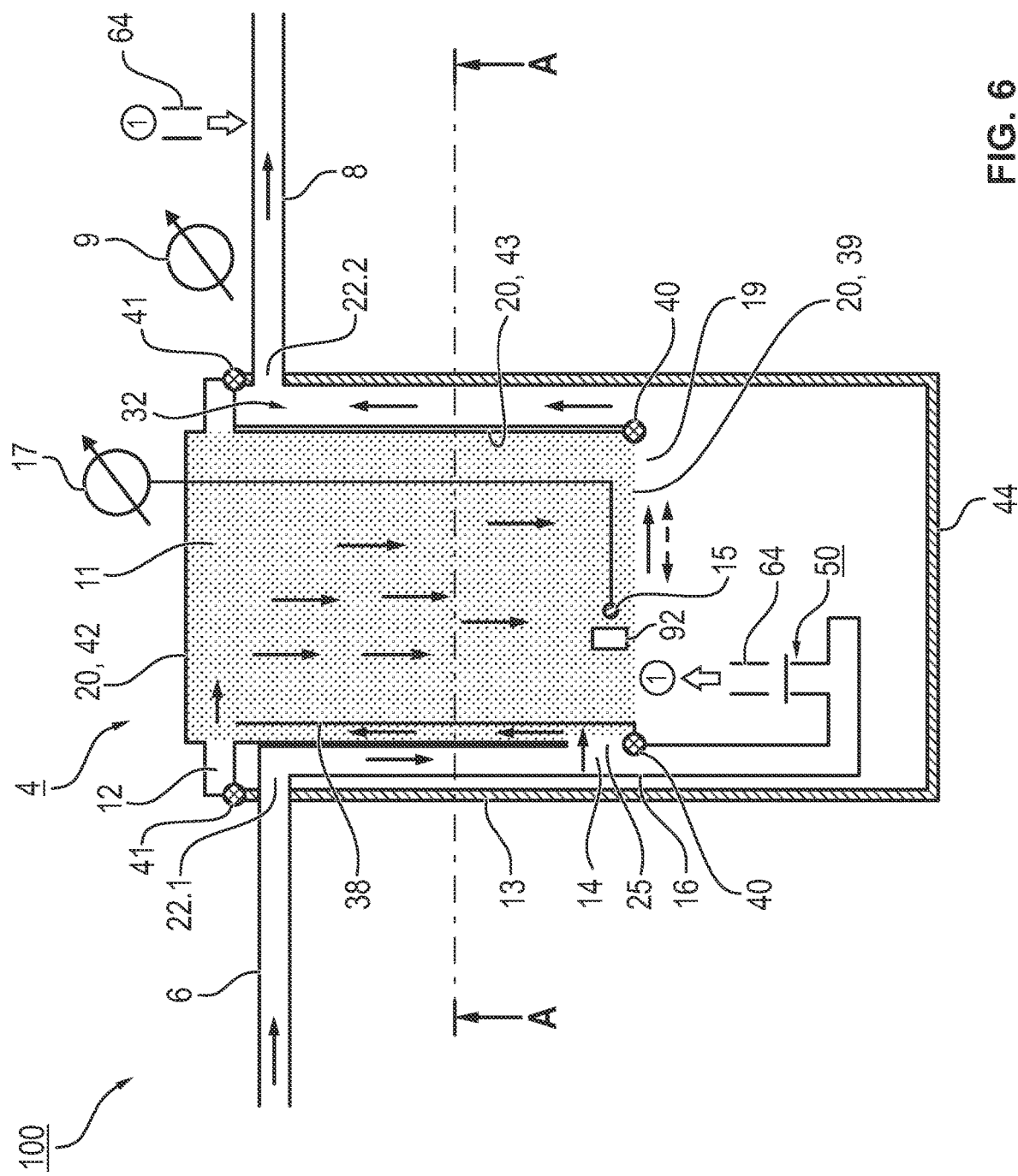
FIG. 6 is a schematic view showing a variant of the embodiment from FIG. 5, wherein the open pressure relief valve does not release gas into the surrounding area, but rather into the discharge line.

FIG. 6 shows a variant, in which an pressure relief valve 50 is likewise used, but this pressure relief valve 50 does not release the excess gas into the surrounding area. Rather, the pressure relief valve 50 is connected parallel to the filter unit 4. The pressure relief valve 50 is located in the interior of the pot 13 and there at the end or close to the end of the pot feed line 16. Gas is released by means of the pressure relief valve 50 from the pot feed line 16 into the pot 13, when the pressure difference in the pot feed line 16 is above the overpressure threshold. A hose 64, which is only suggested schematically, carries the excess gas, which is released from the pressure relief valve 50 in case of an overpressure, past the filter unit 4 to the discharge line 8. This hose 64 may be arranged at least partially in the interior of the pot 13.

The sensor 15 in one embodiment measures an indicator of the quantity of anesthetic, which is not taken up/received by the filter element 11 and hence leaves the filter 11, 20. The sensor 15 is preferably located downstream of the filter unit 4 and measures the concentration of the anesthetic or of at least one anesthetic in the gas stream around the sensor 15. The anesthetic filter 11, 20 ideally filters all the anesthetic out of the gas flowing through and takes up/receives it. When the quantity of anesthetic, which is not suctioned out or otherwise taken up/received by the filter element 11, is above a predefined threshold, then this is an indication that the filter element 11 is filled or has become clogged with anesthetic, cannot take up/receive any more anesthetic and hence must be replaced. In the exemplary embodiment, the sensor, the measurement line 18 and the consumption indicator 17 belong to the cartridge 20. The same cartridge 20 may be used for a plurality of filter elements 11 one after the other. It is possible also that the sensor 15, the measurement line 18 and the consumption indicator 17 are positioned separately from the cartridge 20.

In one embodiment, the cartridge 20 is suspended in the pot 13, wherein the circumferential edge 12 is located at the top on the upper edge of the pot 13. Two upper sealing elements 41 or a single circular sealing element 41 close the area located between the upper edge of the pot 13 and the circumferential edge 12. The sealing ring or another suitable sealing element 41 is preferably guided entirely around the upper edge of the pot 13, so that the inserted cartridge 20 is suspended in the pot 13 in a gas-tight manner. Because the cartridge 20 is suspended in the pot 13 and is not as high as the pot 13 in the exemplary embodiment, an intermediate space is formed between the bottom 39 of the cartridge 20 and the bottom 44 of the pot 13, which belongs to a buffer storage device described below. It is also possible that the cartridge 20 has no circumferential edge 12 and is not suspended in the pot 13, but stands on the bottom 44 of the pot 13.

In all of the embodiments, the filter unit 4 comprises a buffer storage device 19 (embodiment according to FIG. 2 through FIG. 11 and FIG. 14 through FIG. 19) in the interior of the rigid pot 13 or an expandable buffer storage device 70 (FIG. 13) or a rigid buffer storage device 23 (embodiment according to FIG. 20 through FIG. 23) at the feed line 6 or at the discharge line 8, wherein the buffer storage device 19, 23, 70 is in a fluid connection both with the gas lines 6 and 8 and with the surrounding area and is capable of taking up/receiving and releasing fluid. This buffer storage device 19, 23, 70 takes up/receives gas, which has been released from the anesthesia apparatus 1, as long as the rate of the fluid inflow in the feed line 6 is greater than the rate of the fluid outflow in the discharge line 8. The buffer storage device 19, 23, 70 again releases the taken up/received gas, when, conversely, the volume flow in the discharge line 8 is greater than the volume flow in the feed line 6. Especially when the patient P exhales, i.e., in the phase of exhalation, more fluid flows, as a result, from the anesthesia apparatus 1 into the feed line 6 than flows out of the feed line 6. When the patient P inhales, i.e., in the phase of inhalation, less fluid flows into the feed line 6 than flows out.

The described embodiments of a buffer storage device 19, 23, 70 can be combined. It is thus possible that an taking up/receiving system 100 according to the present invention has one, two or three of the different buffer storage devices 19, 23, 70 just described and/or two similar buffer storage devices.

In one embodiment, a rigid buffer storage device 23 is located below the pot 13. The gas to be taken up/received is, as a rule, heavier than air and sinks through an opening 26 in the bottom 44 of the pot 13 into the buffer storage device 23, which is located below the pot 13.

Figure 7:
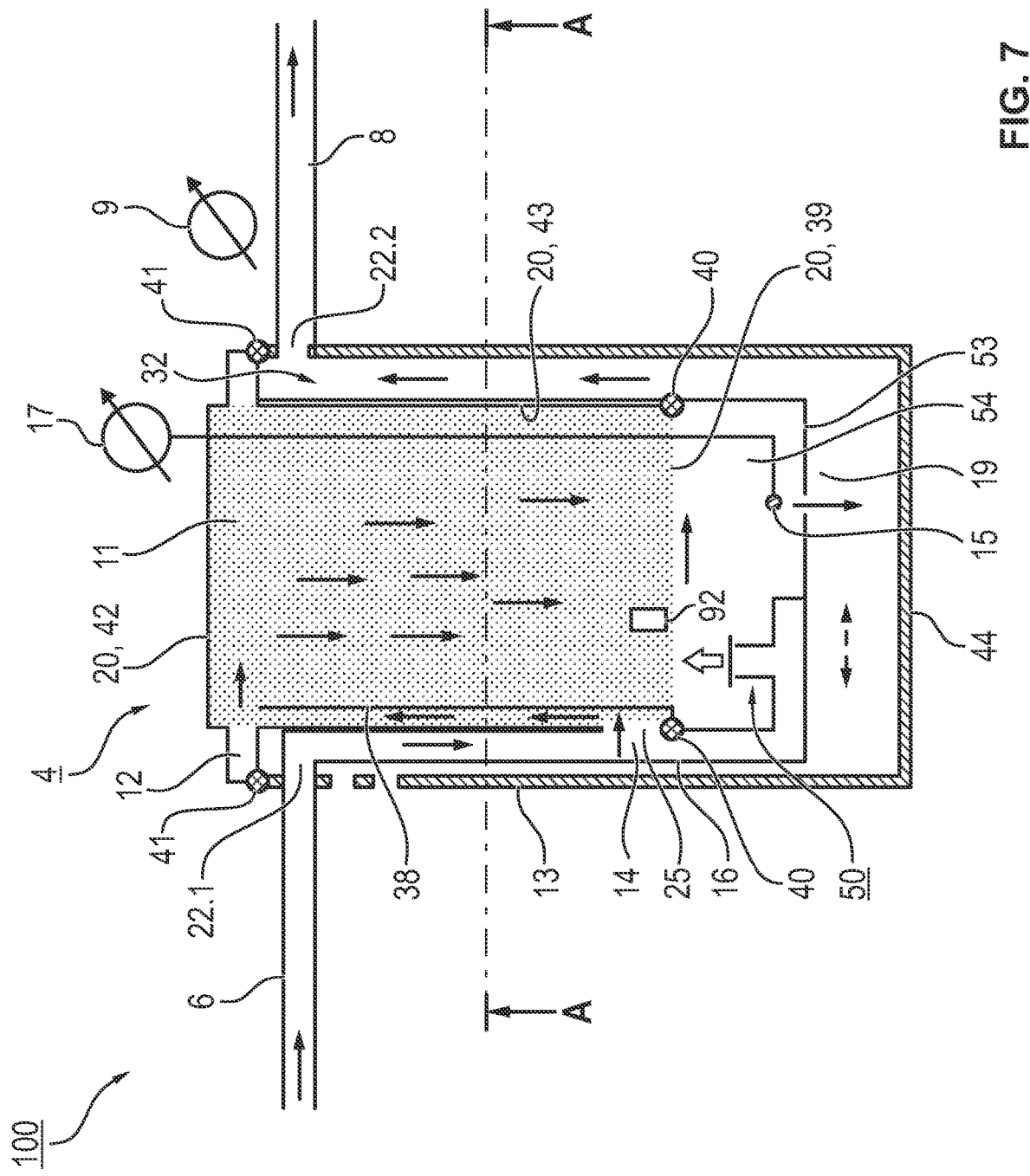
FIG. 7 is a schematic view showing a variant of the embodiment from FIG. 6, wherein the sensor of the filter unit also measures a property of the gas released by the pressure relief valve.

In the example from FIG. 7, a preferably horizontal partition 53 separates the buffer storage device 19 from the filter unit 4. Both the gas, which flows through the filter unit 4 and is filtered in this filter unit 4, and the excess gas, which is released from the pressure relief valve 50, reaches a space 54 between the filter unit 4 and the partition 53. The gas from this space 54 reaches the buffer storage device 19 through an opening in the partition 53 and then flows out of the buffer storage device 19 through the pot discharge line 32 into the discharge line 8.

The sensor 15 is located in the embodiment from FIG. 7 in the space 54, i.e., downstream of the filter 11, 20, and measures the concentration of anesthetic in the space 54. A concentration above the predefined threshold has at least one of the following two causes:

The filter unit 4 has become clogged or is spent for a different reason and is no longer capable of sufficiently filtering anesthetic out of the gas stream flowing through for this reason or for a different reason.

The pressure in the pot feed line 16 is above the overpressure threshold, and the pressure relief valve 50 has opened and is releasing gas into the space 54 in the pot 13.

Both events require replacing the filter unit 4. The display unit 17 sends a signal to a user that the filter unit 4 must be replaced.

FIG. 8 shows seven different possible embodiments of the pressure relief valve 50. The pressure relief valve 50 in the embodiments according to FIG. 4, FIG. 6 or FIG. 7 can be implemented with each of these embodiments.

FIG. 8a shows the already described embodiment 50.1, in which a valve plate 51 is located on a valve crater 52. In case of a sufficiently high pressure, the valve plate 51 is raised, so that gas can be released from an intermediate space between the raised valve plate 51 and the valve crater 52. The ratio between the weight of the valve plate 51 and the area of the opening of the valve crater 52 determines the overpressure threshold.

The pressure relief valve 50.2 according to FIG. 8b additionally comprises a compression spring 55 which is supported at a housing of the pressure relief valve 50 and aims to press the valve plate 51 upwards against gravity. The valve plate 51 is preferably configured as being heavier than in case of the embodiment according to FIG. 8a. The overpressure threshold is additionally determined by the spring constant of the compression spring 55. The pressure relief valve 50.2 according to FIG. 8b opens only if a pressure is above the overpressure threshold for a sufficiently long time. Brief pressure peaks are thus taken up/received. The risk is reduced that a leak occurs in the pressure relief valve 50. Such an pressure relief valve may be provided as described, for example, in U.S. Pat. No. 8,997,741 B2 (the entire contents of which are incorporated herein by reference).

In case of the pressure relief valve 50.3 according to FIG. 8c, the valve plate 51 is replaced with a valve ball 56, which is located on the valve crater 52. The overpressure threshold is determined, in turn, by the ratio between the weight of the valve ball 56 and the area of the valve crater 52.

The pressure relief valve 50.4 according to FIG. 8d comprises a valve flap 57, which is fastened to the valve crater 52 and can be rotated in relation to the valve crater 52 about a horizontal axis of rotation, which is at right angles to the drawing plane of FIG. 8. An overpressure rotates this valve flap 57 against gravity away from the valve crater 52, so that an opening is formed at the free end of the valve crater 52. Gravity as well as optionally a tension spring, not shown, aim to hold the valve flap 57 in the closed position. As an alternative, the optional tension spring aims to pull the valve flap 57 against gravity into the open position and to hold it in this open position. Especially a relatively heavy valve flap 57 in connection with the optional tension spring also causes the pressure relief valve 50.4 to open only if an overpressure is present for a sufficiently long time. Brief pressure fluctuations are taken up/received.

The pressure relief valve 50.5 according to FIG. 8e comprises a U-shaped tube 58, in which a liquid 59 is located in a lower part. This liquid 59 evaporates only at a temperature above the temperatures, at which the pressure relief valve 50 is inserted and mounted. In case the pressure reaches or exceeds the overpressure threshold, then the gas is released from the tube 58 in the form of bubbles. This configuration especially readily reduces the risk that gas is unintentionally released due to a leak.

The pressure relief valve 50.6 according to FIG. 8f comprises an actuatable on-off valve 61 and a pressure sensor 60 in the feed line 52 to the actuatable on-off valve 61. The signals from the pressure sensor 60 are forwarded to an electric comparator or to a processor. In case the comparator or processor or even the pressure sensor 60 itself detects the event that the pressure in the feed line 52 is above the overpressure threshold, then it actuates the on-off switch 61 and opens it as a result. In case the pressure again drops below the overpressure threshold, then it again closes the on-off valve 61. Optionally, a signal for the measured pressure and/or a message that the overpressure threshold was exceeded are forwarded to an output unit, not shown, preferably in conjunction with an identification of the position of the pressure relief valve 50.6 in the hospital. The output unit outputs the measured pressure or the message in a form perceptible by a person. This output unit may be arranged at a distance in space from the taking up/receiving system 100, for example, in a center.

In case of the pressure relief valve 50.7 according to FIG. 8g, a type of duck-bill-shaped area 62 is placed onto the valve crater 52. In case of a pressure above the overpressure threshold, the duck-bill-shaped area opens and closes again at a lower pressure.

The following two undesirable events, which could both lead to a harm of the patient P, have to be prevented:

A backup occurs in the feed line 6, for example, because the filter element 11 has taken up/received a lot of anesthetic and has become partially clogged as a result or because of liquid or because the anesthesia apparatus 1 has currently discharged relatively much gas into the feed line 6. This backup could travel into the anesthesia apparatus 1 and has an effect on the ventilation circuit.

Excess gas is suctioned from the anesthesia apparatus 1 through the feed line 6 and through the discharge line 8, for example, because the anesthesia apparatus 1 has currently discharged relatively little gas into the feed line 6.

The pressure relief valve 50 described with reference to FIG. 4 through FIG. 8 prevents an overpressure, which may occur, for example, because of a backup. In order to prevent both undesirable events, in one embodiment the buffer storage device 19 is in a fluid connection with the surrounding area via at least one opening 21, preferably a plurality of openings 21, in the wall of the pot 13. When a plurality of openings 21 are present, the fluid connection is retained even if one opening 21 has become clogged, for example, because an object was suctioned. The embodiment that at least one opening 21 is formed in the wall of the buffer storage device 19 is especially meaningful in combination with a suctioning, i.e., with a suction pump 10, which suctions gas into the discharge line 8, cf. FIG. 1. In case excess gas exclusively reaches the buffer storage device 19 by the anesthesia apparatus 1 discharging the excess gas, i.e., in case no suctioning is being carried out, the buffer storage device 19 preferably has no lasting fluid connection with the surrounding area.

It is possible to provide both the pressure relief valve 50 and the openings 21 in the wall of the pot 13 or else only the pressure relief valve 50 or only the openings 21. For example, the openings 21 are shown in FIG. 2 through FIG. 4, FIG. 10, FIG. 11 and FIG. 14 through 17, and the pressure relief valve 50 is shown in FIG. 5 through FIG. 7.

As already mentioned, in one embodiment the buffer storage device 19 in the rigid pot 13 is in a fluid connection with the surrounding area via at least one opening 21. The rigid buffer storage device 23 below the pot 13 or downstream of the pot 13 is in one embodiment in a fluid connection with the surrounding area via at least one opening 24. Through this opening 21 or 24, excess gas can flow back and forth between the buffer storage device 19, 23 and the surrounding area. This is suggested by broken arrows in FIG. 2 through FIG. 24.

In one variant, an pressure relief valve 50, which opens or is opened when the difference between the pressure in the buffer storage device 23 and the ambient pressure is above a predefined overpressure threshold, is arranged in front of the opening 24 or at the location of the opening 24 in a wall of the buffer storage device 23. This pressure relief valve 50 may be configured as described with reference to FIG. 8.

FIG. 20 to FIG. 24 show an embodiment with a rigid buffer storage device 23, which is in a fluid connection with the surrounding area via an opening 24 or an pressure relief valve 50—of course, only in case of an open valve in case of the pressure relief valve 50. It is also possible that the rigid buffer storage device 50 is in a fluid connection with an elastic buffer storage device 70 via the opening 24, i.e., a buffer storage device with variable volume. This elastic buffer storage device 70 may be configured as this is described with reference to FIG. 13.

Figure 11:
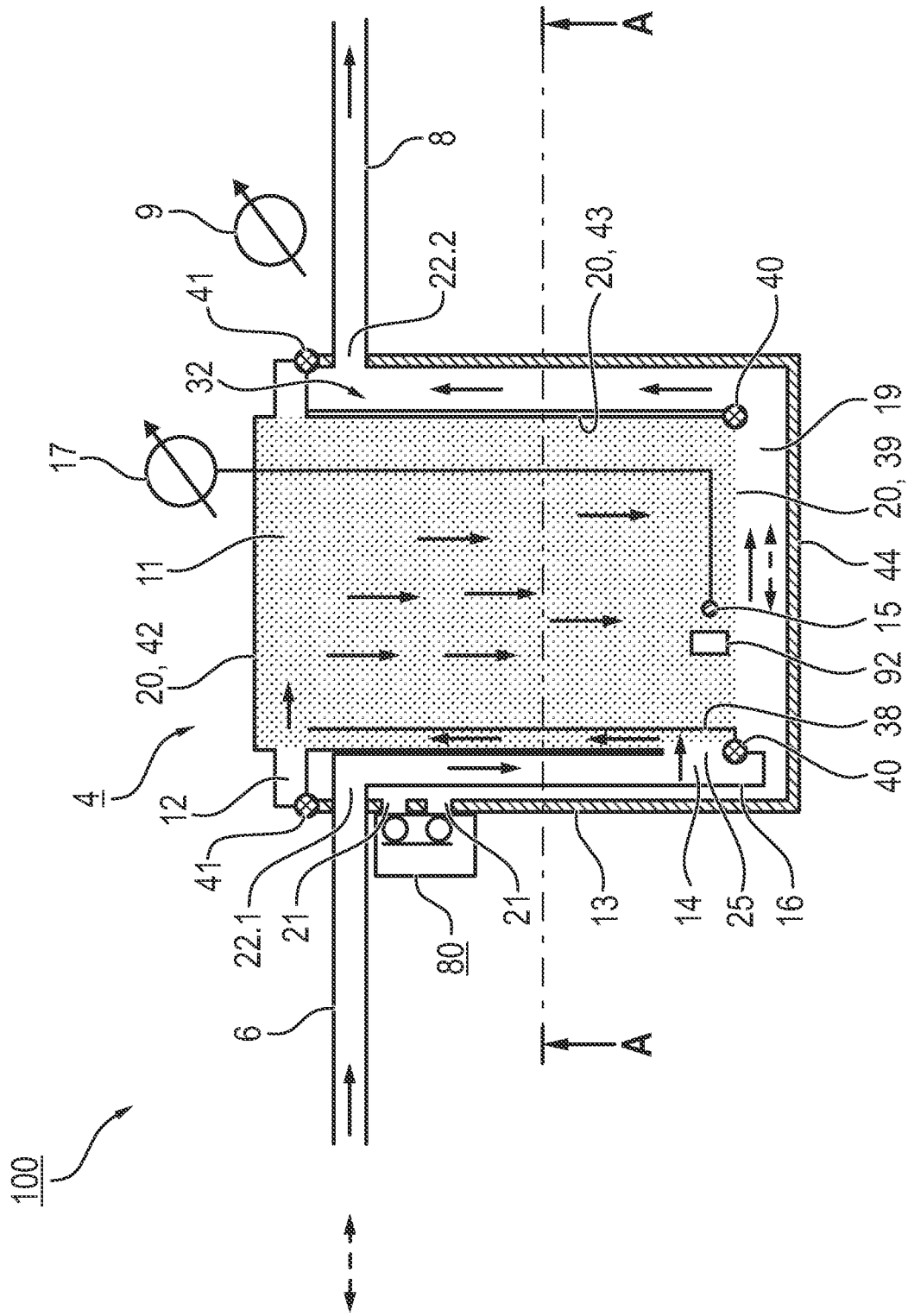
FIG. 11 is a schematic view showing an embodiment with a vacuum valve at the pot.
Figure 14:
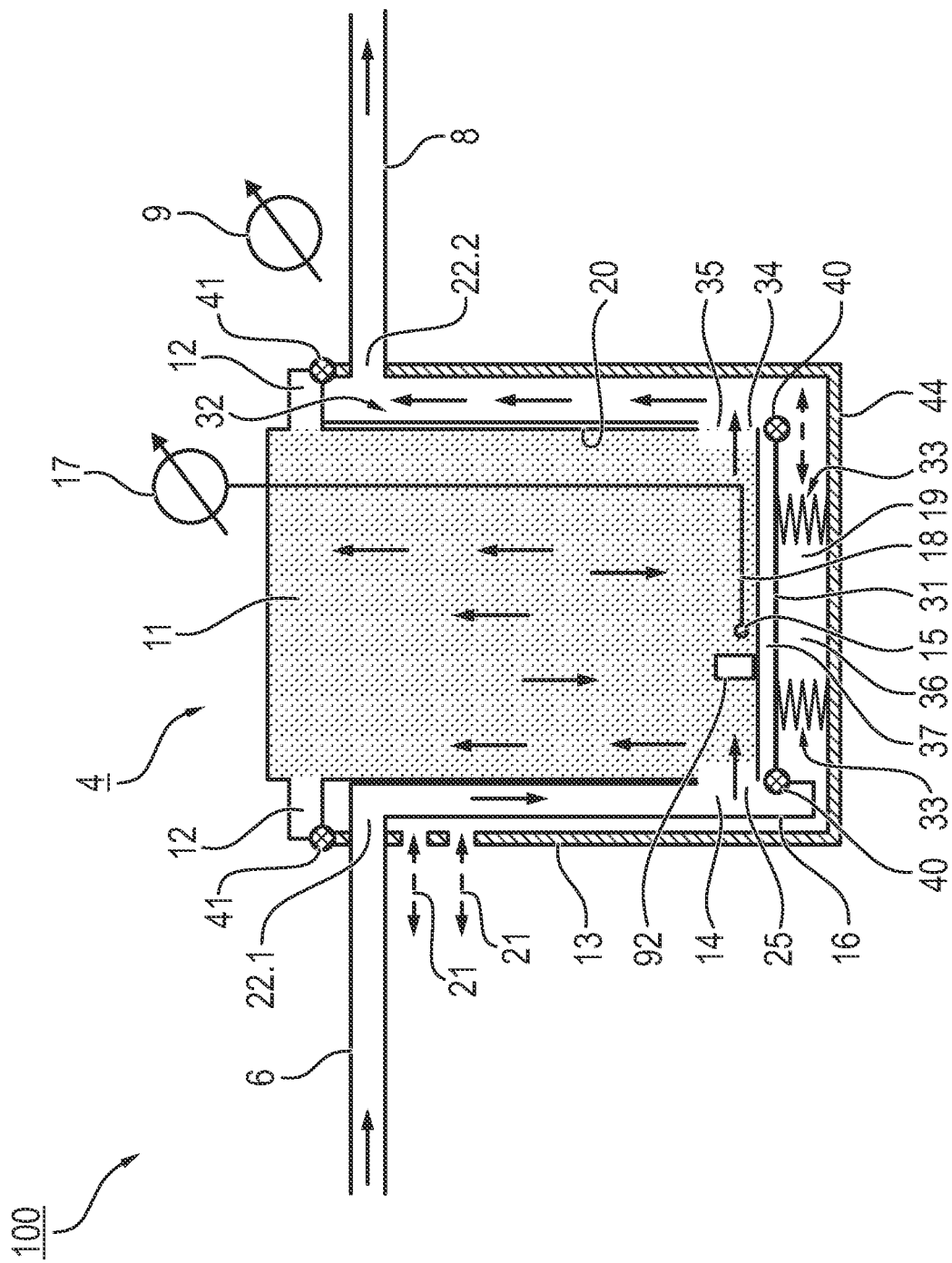
FIG. 14 is a schematic view showing an embodiment with a mechanically acting buffer storage device in the interior of the filter mount and additionally below the filter, wherein the cartridge is inserted.

FIG. 11 shows an alternative to or else addition to the embodiment that the interior of the pot 13 is always in a fluid connection with the surrounding area via the openings 21. This alternative reduces the quantity of anesthetic, which is released from the pot 13. In addition, the alternative described below causes the pressure in the pot 13 to be below the pressure in the surrounding area around the pot 13 by no more than a predefined vacuum threshold. A vacuum that is too high is often undesirable because it can suction gas out of the anesthesia apparatus 1. The embodiment described below for avoiding a too high vacuum in the pot 13 is especially meaningful in conjunction with a suctioning, i.e., with a suction pump 10, which suctions gas into the discharge line 8. In case the pot 13 has at least one opening 21, then an undesirable vacuum can especially occur when the opening 21 or each opening 21 is plugged. A spent or clogged filter 11, 20 may likewise lead to a too high vacuum in case of suctioning.

A vacuum valve 80 overlaps the openings 21 in the lateral wall of the pot 13. This vacuum valve 80 opens when a vacuum greater than the vacuum threshold prevails in the pot 13, i.e., when the pressure in the pot 13 is below the ambient pressure by more than the vacuum threshold. Otherwise, the vacuum valve 80 is closed. The openings 21 limit the maximum volume flow into the pot 13. They may belong to the vacuum valve 80.

In one embodiment, an alarm is indicated on an alarm generation unit located at a distance in space or outputted in a different manner, as soon as the vacuum valve 80 has opened. For example, this alarm is outputted in a center. A user may check the pot 13 as a response to this alarm.

FIG. 12 shows seven different possible embodiments of the vacuum valve 80 from FIG. 11. For example, a part of the lateral wall of the pot 13 as well as an overlapped opening 21 are shown in FIG. 12. Each embodiment shown of the vacuum valve 80 corresponds to a respective embodiment of the pressure relief valve 50, which is shown in FIG. 8. Identical reference numbers in FIG. 12 have the same meaning as in FIG. 8.

In the embodiment according to FIG. 2 through FIG. 17, the feed line 6 opens into the pot feed line 16, which is guided vertically or obliquely along the inner wall of the pot 13 and which has an outlet opening 14 close to the bottom 39 of the cartridge 20. An inlet opening 25 is present in the lateral surface 43 and close to the bottom 39 of the cartridge 20. Excess gas, which is released from the anesthesia apparatus 1, flows through the feed line 6 and the opening 22.1 in the pot 13 into the pot feed line 16. This gas is, as a rule, heavier than air. Therefore, the discharged excess gas flows downwards in the pot feed line 16, which is arranged vertically or obliquely. The discharged excess gas flows through the gas lines 6 and 16 up to the outlet opening 14 and reaches the anesthetic filter 11, 20 through the inlet opening 25. The excess gas is discharged by the medical apparatus 1 and/or is suctioned by the suction pump 10 and passes through the filter element 11, wherein the excess gas is forced on a preferably serpentine path, as a result of which anesthetic is filtered out of the gas. The filtered excess gas is released from an outlet opening 34 from the cartridge 20, flows through the inlet opening 35 into the pot discharge line 32 and reaches the discharge line 8 and from there the gas taking up/receiving unit 7 through an opening 22.2 in the pot 13.

In case of the embodiment according to FIG. 2 through FIG. 17 the buffer storage device 19 is formed by an intermediate space between the inner wall of the pot 13 and the outer wall of the cartridge 20. This intermediate space 19 adjoins both the lateral surface and the bottom 44 of the pot 13.

FIG. 13 shows three possible embodiments of a buffer storage device 70, which is in fluid connection with the feed line 6 and is arranged in series and upstream of the filter unit 4. This buffer storage device 70 is made of an elastic material in all embodiments. The ambient pressure acts from the outside on the buffer storage device 70. When a sufficient quantity of gas flows into the feed line 6 and, as a result, a sufficiently high pressure is present in the buffer storage device 70, then the elastic buffer storage device 70 is expanded, and especially is expanded more widely, the greater the difference between the pressure in the feed line 6 and the ambient pressure is. When the pressure decreases, then the elastic buffer storage device 70 contracts again and as a result releases taken up/received gas again into the feed line 6.

It is also possible that the elastic buffer storage device 70 is in a fluid connection with the discharge line 8. It is also possible that a first elastic buffer storage device 70 is in fluid connection with the feed line 6 and a second elastic buffer storage device 70 is in fluid connection with the discharge line 8.

According to the embodiment according to FIG. 13a, the feed line 6 has a connecting piece 71, which is preferably arranged below the feed line 6 or even below the discharge line 8 and points downwards (anesthetic is heavier than air). A buffer storage device 70 is suspended at this connecting piece 71 in the form of an elastic bag 70.1. In case of a high pressure, gas flows from the feed line 6/discharge line 8 into the bag 70.1 due to the connecting piece 71 and expands this bag 70.1. In case of decreasing pressure, the bag 70.1 contracts again and again releases taken up/received gas to the feed line 6/discharge line 8. A bag, which was originally intended or configured for manual ventilation, can preferably be used as the bag 70.1, because such manual ventilation bags are already standardized and approved for medical use.

In the embodiment according to FIG. 13b, a section of the feed line 6 or else of the discharge line 8 is entirely or at least partially enclosed by a buffer storage device 70 in the form of an elastic bag 70.2. This section of the feed line 6 or of the discharge line 8 has holes or other openings, so that the bag 70.2 is in a fluid connection with the feed line 6 or with the discharge line 8. The elastic bag 70.2 completely overlaps the openings in the feed line 6 or in the discharge line 8. In turn, the elastic bag 70.2 is expanded in case of a high pressure and contracts in case of a vacuum.

In case of the embodiment according to FIG. 13c, the elastic buffer storage device 70 has the form of a bellows 70.3, which is in a fluid connection with the feed line 6 or with the discharge line 8 via a connecting piece 72. The bellows 70.3 is expanded in case of a high pressure along a longitudinal axis and again contracts in case of a lower pressure. The bellows 70.3 may be located above or below or even on the side of the feed line 6 or the discharge line 8.

Figure 20:
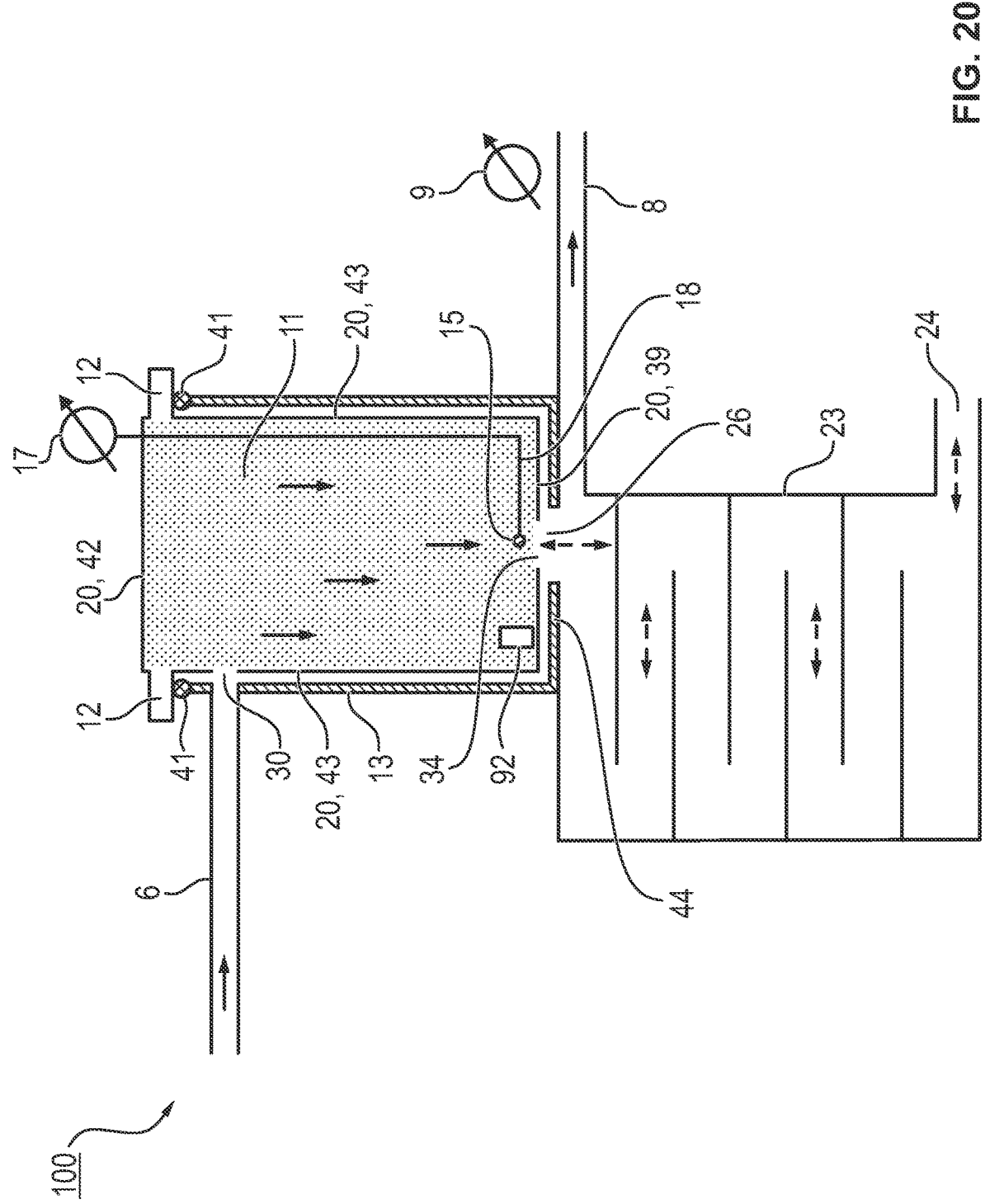
FIG. 20 is a schematic view showing an embodiment with a separate buffer storage device below the filter mount, wherein the cartridge is inserted.
Figure 21:
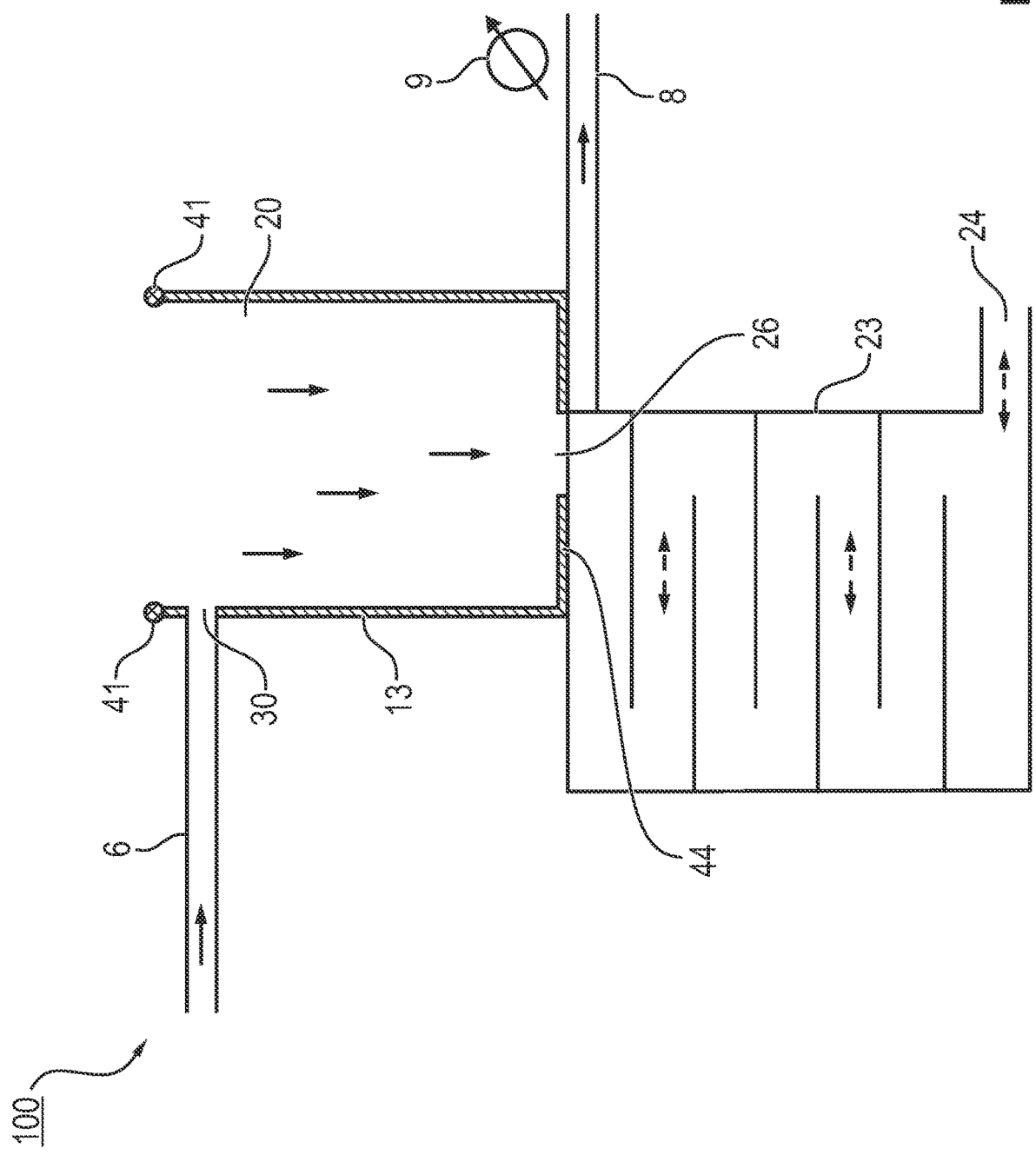
FIG. 21 is a schematic view showing the embodiment from FIG. 20, wherein the cartridge has been removed.

In case of the embodiment according to FIG. 20 and FIG. 21, the buffer storage device 23 is formed by a separate buffer storage device, which preferably comprises a meandering tube. An inlet opening 30 is arranged in the upper third of the cartridge 20, the outlet opening 34 is arranged in the bottom 39 of the cartridge 20. The buffer storage device 23 is in fluid connection with the pot 13 via an opening 26. This opening 26 overlaps the outlet opening 34. Thanks to the outlet opening 34 in the bottom 39 of the cartridge 20, the buffer storage device 23 is also in fluid connection with the anesthetic filter 11, 20. In addition, the buffer storage device 23 is in fluid connection with the discharge line 8 as well as in fluid connection with the surrounding area via the opening 24. The meandering tube leads from the opening 26 to the opening 24.

Discharged excess gas flows through the feed line 6 and from the side reaches the inlet opening 30 in the cartridge 20. The excess gas flows from the top downwards through the anesthetic filter 11, 20 and is released again from the anesthetic filter 11, 20 in the outlet opening 25. As soon as the suction pump 10 suctions gas, this gas is suctioned through the discharge line 8 from the buffer storage device 23 again. The buffer storage device 23 thus functions according to the last-in-first-out principle. The meandering shape of the buffer storage device 23 embodies a long tube having relatively small dimensions. The long tube reduces a mixing of the discharged excess gas with the ambient air.

Figure 3:
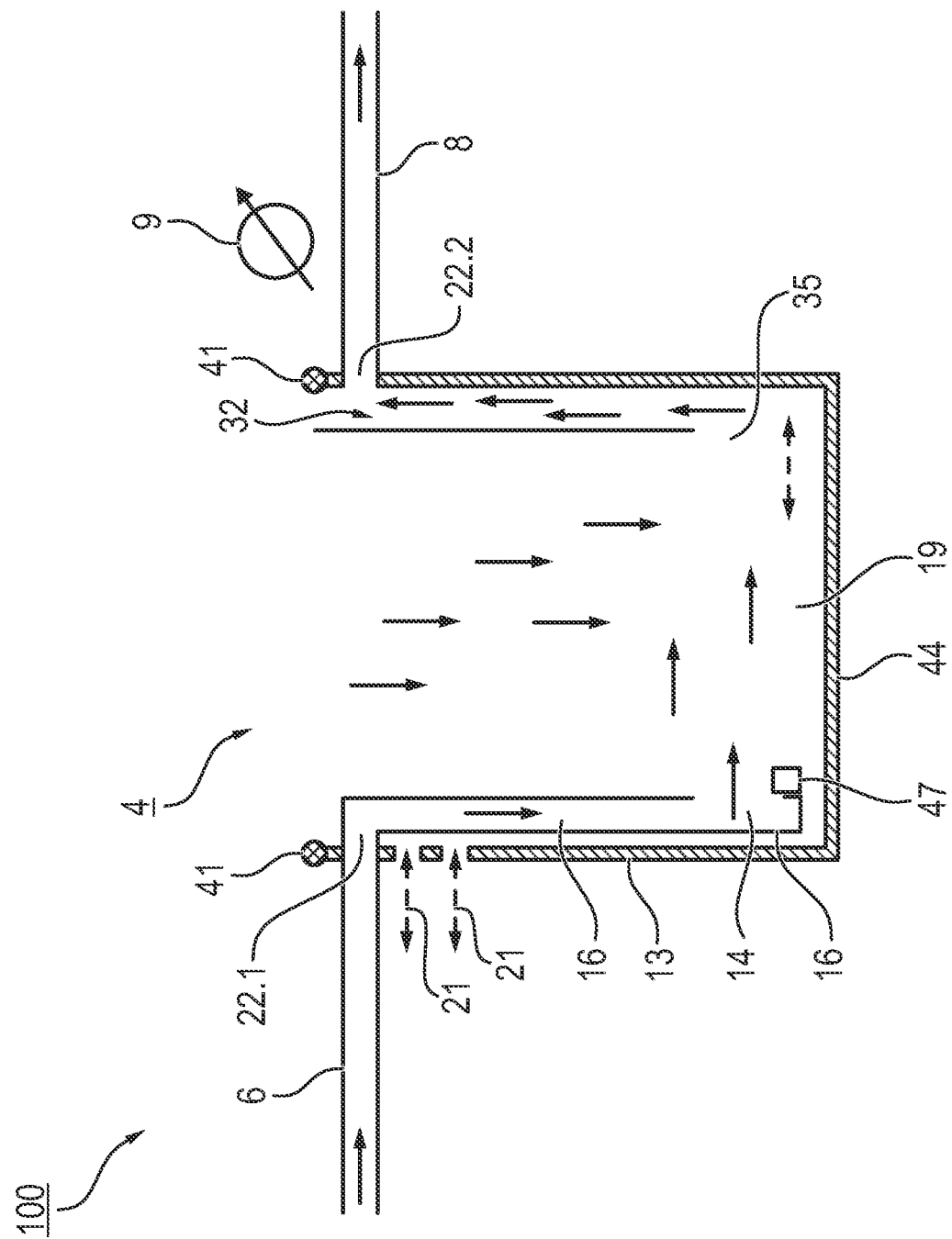
FIG. 3 is a schematic view showing the embodiment from FIG. 2, wherein the cartridge has been removed.
Figure 4:
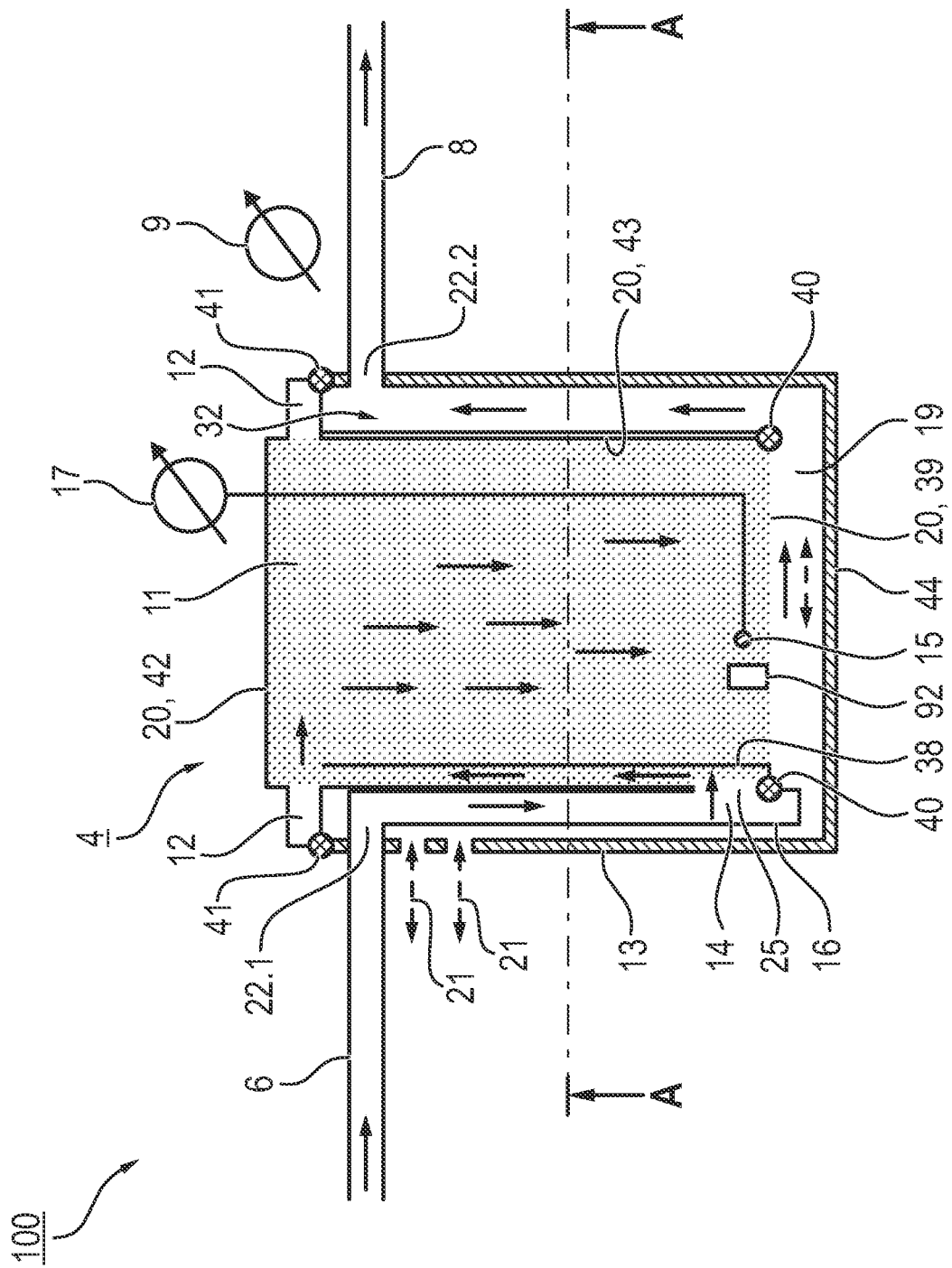
FIG. 4 is a schematic view showing a variant of the embodiment from FIG. 2, wherein the gas is forced through the cartridge and the cartridge is inserted.
Figure 15:
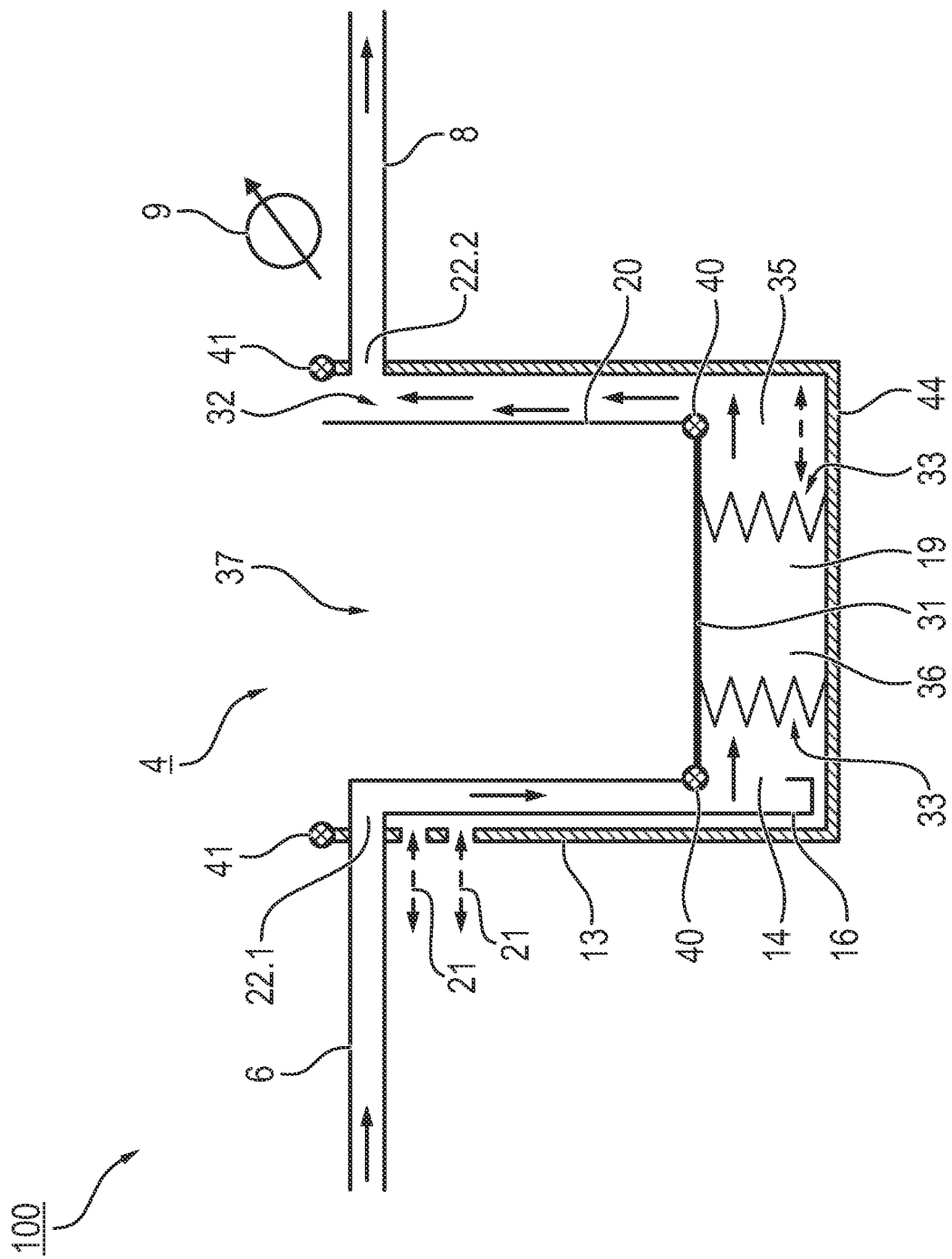
FIG. 15 is a schematic view showing the embodiment from FIG. 14, wherein the cartridge has been removed.
Figure 16:
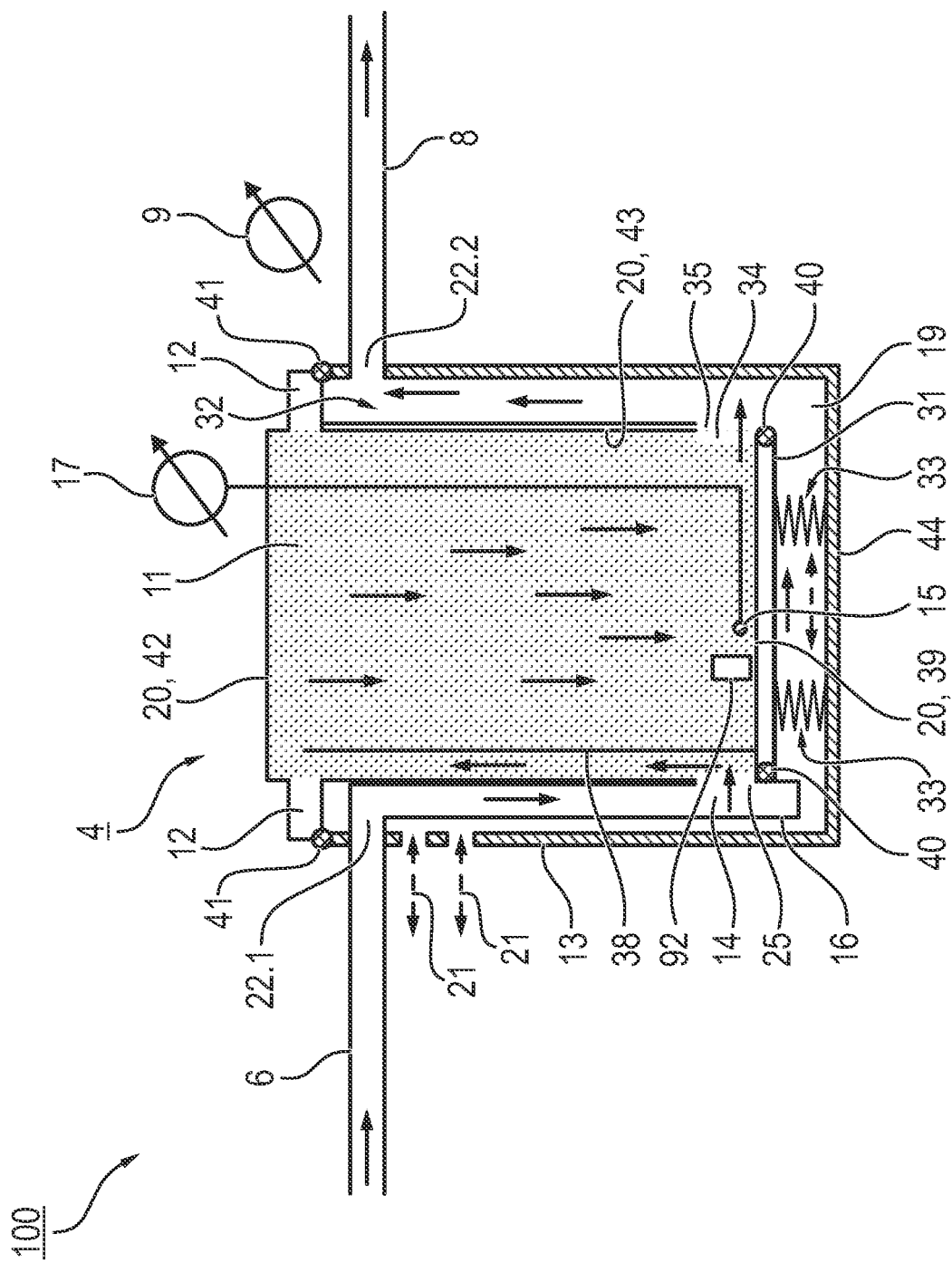
FIG. 16 is a schematic view showing a variant of the embodiment from FIG. 14 and FIG. 15, wherein the gas is forced through the cartridge and the cartridge is inserted.

The filter element 11 takes up/receives anesthetic and gradually becomes clogged and/or is saturated as a result. In case the filter element 11 has become largely clogged or is saturated and therefore can no longer take up/receive any more anesthetic or in case it has become swollen, then the filter element 11 or the entire anesthetic filter 11, 20 must be replaced. The optional consumption indicator 17 indicates this event in many cases. The cartridge 20 with the filter element 11 and the display unit 16, 17, 18 is removed from the pot 13. FIG. 3, FIG. and FIG. 15 show the situation after removal of the cartridge 20. The mechanical ventilation of the patient P may not be interrupted, while the cartridge 20 with the filter element 11 is being replaced. Therefore, the fluid connection is retained between the anesthesia apparatus 1 and the gas taking up/receiving unit 7. Even if no cartridge is inserted into the pot 13, a large quantity of discharged gas is prevented from being released into the surrounding area.

Figure 22:
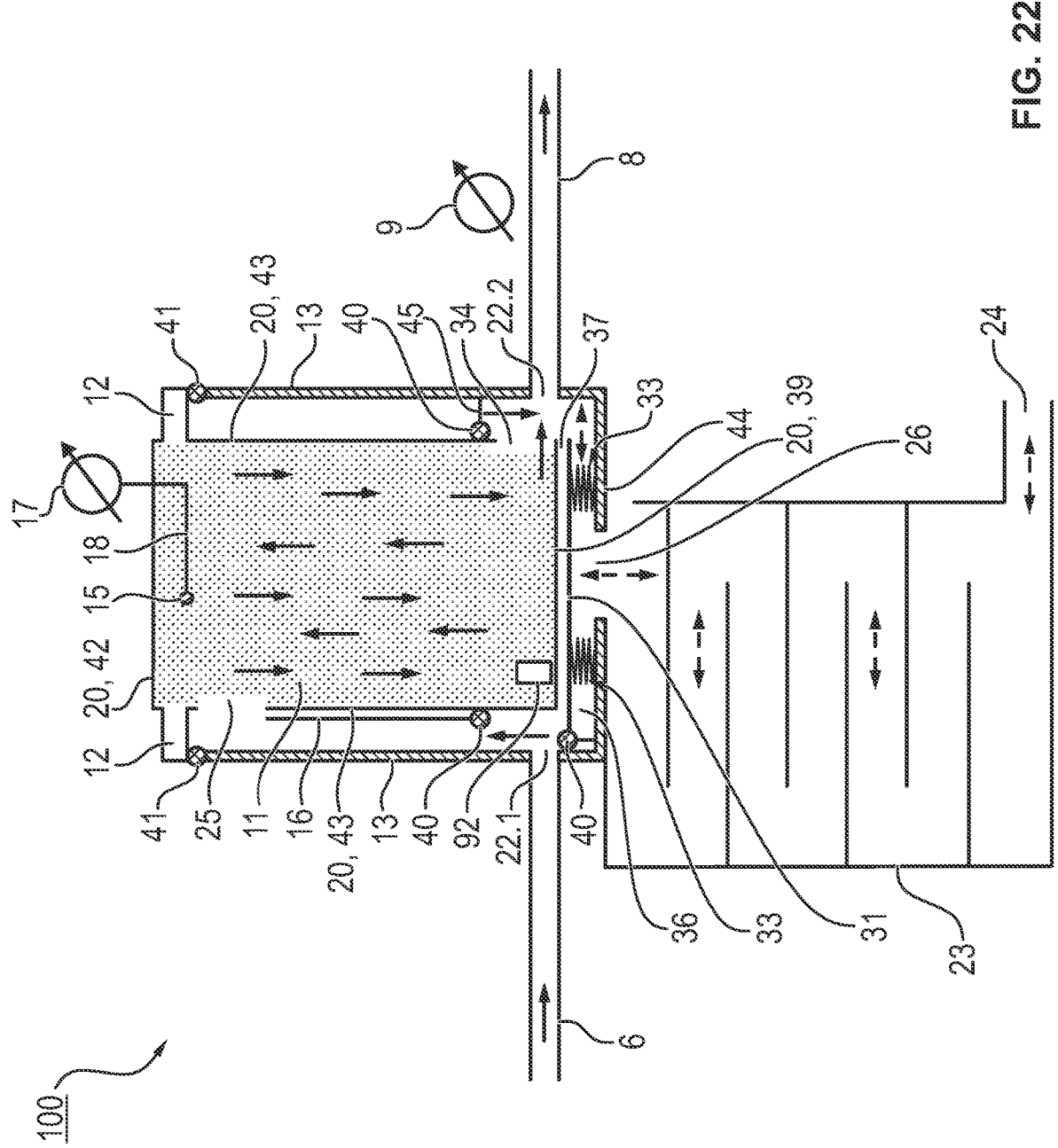
FIG. 22 is a schematic view showing a combination of a plurality of embodiments of the buffer storage device, wherein the cartridge is inserted.
Figure 23:
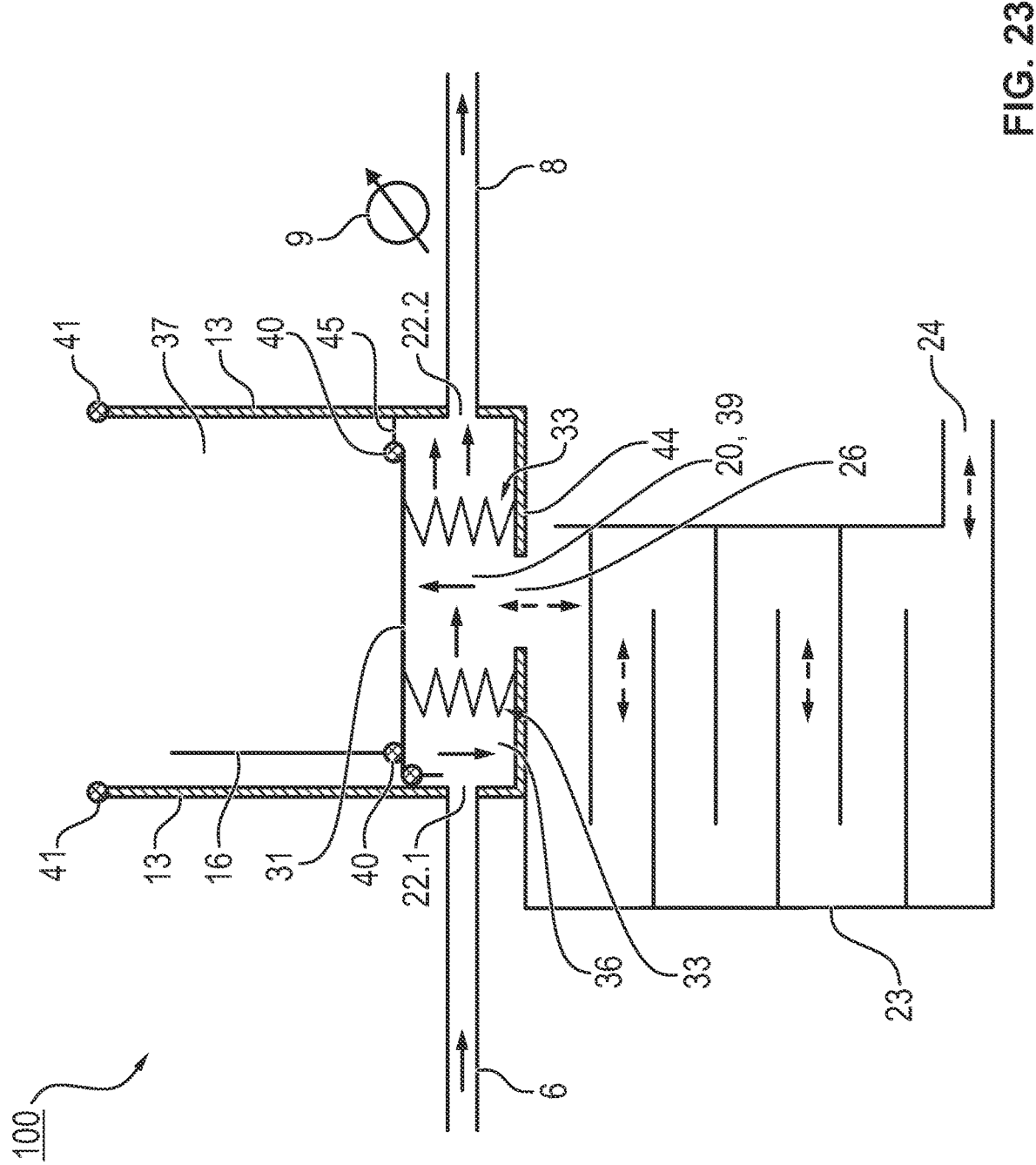
FIG. 23 is a schematic view showing the combination from FIG. 22, wherein the cartridge has been removed.
Figure 24:
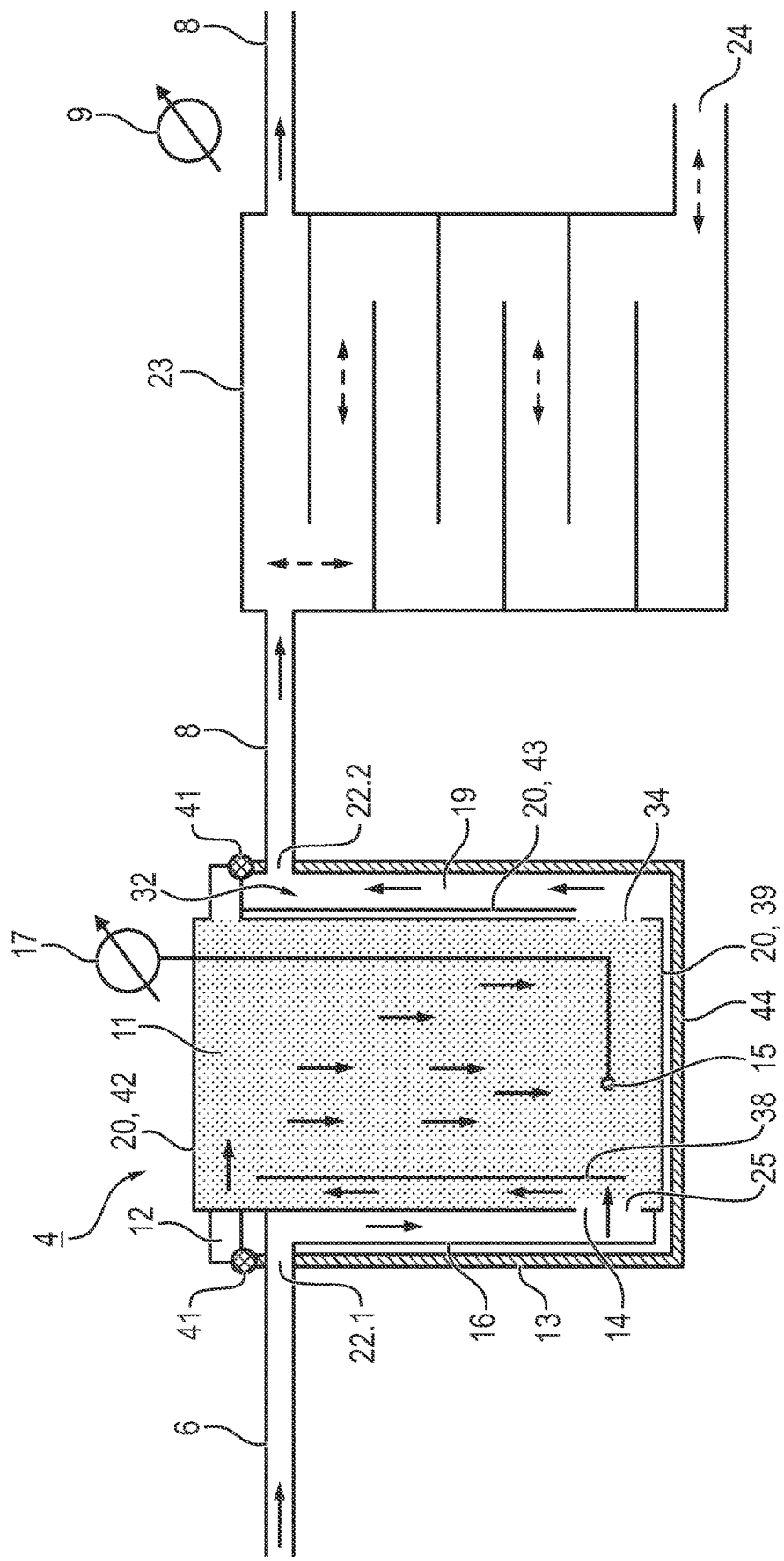
FIG. 24 is a schematic view showing an embodiment with a separate buffer storage device downstream of the filter mount.

In the embodiment according to FIG. 2 through FIG. 10, this is achieved pneumatically, namely by excess gas being suctioned; this is achieved mechanically, namely by a spring-mounted plate 31 in the embodiment according to FIG. 14 through 17; in the embodiment according to FIG. 20 and FIG. 21 as well as FIG. 24 this is achieved by the meandering shape of the buffer storage device 23 and in the embodiment according to FIG. 22 and FIG. 23, this is achieved by a combination of the spring-mounted plate 31 and the meandering shape of the buffer storage device 23. The elastic buffer storage device 70 from FIG. 13 also prevents up to a certain extent a large quantity of anesthetic from being released into the surrounding area during a replacement of the cartridge 20.

In case of the pneumatic solution according to FIG. 2 through FIG. 10, the excess gas collects in the intermediate space 19 between the pot 13 and the cartridge 20. In case a suction pump 10 is present, then this gas is suctioned from the bottom 44 of the pot 13 through the discharge line 8. The inlet opening 35 into the pot discharge line 32 preferably has a larger cross-sectional area than the entire cross-sectional area of the openings 21 in the pot 13. In particular, even if the volume flow through the feed line 6 fluctuates over time, it is therefore achieved that only a small portion of the excess gas is released from the pot 13 upwards or through the openings 21 into the surrounding area. The pot 13 itself thus functions as the buffer storage device or as a buffer storage device.

The gas is preferably carried through the filter unit 4 by means of forcing. This forcing is explained below with reference to FIG. 4 through FIG. 10 (pneumatic solution) as well as with reference to FIG. 14 through FIG. 19 (mechanical solution).

A wall 38, which is impermeable to fluid, is inserted into the interior of the filter 11, 20. This wall 38 preferably extends at a distance parallel to the central axis of the filter 11 and preferably has the shape of a flat surface or a surface bent along a vertical axis. The wall 38 divides the cartridge 20 and thus the filter element 11 in the cartridge 20 into an ascent area Au and a descent area Ab for the gas, cf. FIG. 9. Viewed in a n observation direction parallel to the central axis of the filter 11, 20, both the ascent area Au and the descent area Ab have each the shape of a circular segment. The ascent area Au is in fluid connection with the inlet opening 25. The bottom 39 of the cartridge 20 is permeable to gas in this embodiment at least in the descent area Ab, functions as the outlet opening and thus replaces the outlet opening 34 in the lateral surface 43. The descent area Ab opens into this permeable bottom 39.

The gas from the feed line 6 is forced through the filter unit 4 as follows: Precisely as in the other exemplary embodiment, gas is discharged from the medical apparatus 1 and/or suctioned into the discharge line 8. The gas flows through the pot feed line 16 and through the outlet opening 14 and the inlet opening 25 into the ascent area Au, which is located between the wall of the cartridge 20 and the vertical wall 38. An intermediate space is located between the wall 38 and the cover 42 of the cartridge 20. Due to this intermediate space the gas reaches the descent area Ab from the ascent area Au without leaving the pot 13. The gas flows through the descent area Ab to the permeable bottom 39 and then flows through the pot discharge line 32 to the discharge line 8. The gas is hereby preferably filtered both in the ascent area Au and in the descent area Ab, but at least in the descent area Ab.

Two lower sealing elements 40 or a circular sealing ring 40 prevent suctioned gas from the pot feed line 16 from flowing past the cartridge 20 due to the space between the bottom 39 of the cartridge 20 and the bottom 44 of the pot 13. This gas would flow past the filter 11, 20 and hence not be filtered, which is undesirable.

In case of the mechanical solution according to FIG. 14 through FIG. 19 and FIG. 22, a plate 31 is mounted close to the bottom 44 of the pot 13. This plate 31 switches over the path of the gas depending on whether the cartridge 20 is inserted or removed. In a preferred embodiment, the plate 31 occupies the entire cross-sectional area of the pot 13—except for the pot gas lines 16 and 32 and except for unavoidable gaps. The plate 31 divides the interior of the pot 13 into a filter cavity 37 and a buffer storage device cavity 36. The filter cavity 37 is located above the plate 31 and is capable of receiving and enclosing the filter 11, 20. The buffer storage device cavity 36 is located between the plate 31 and the bottom 44 and belongs to a buffer storage device, which is described below. A circular sealing ring 40 preferably encloses the circumferential surface of the plate 31.

Figure 17:
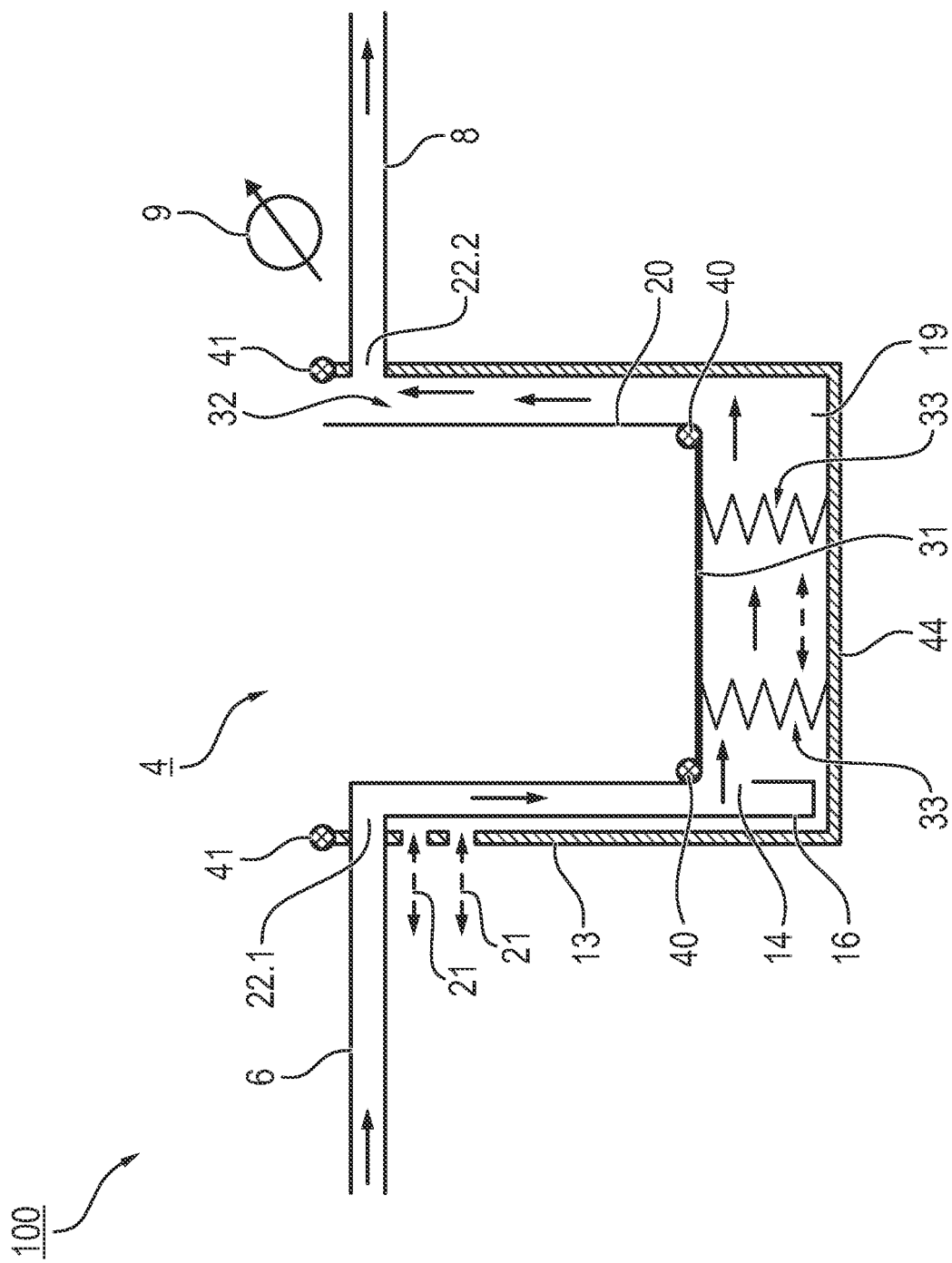
FIG. 17 is a schematic view showing the embodiment from FIG. 16, wherein the cartridge has been removed.

The feed line 6 is in fluid connection with the inserted cartridge 20 via the pot feed line 16 and via the opening 14. The discharge line 8 is in fluid connection with the inserted cartridge 20 via the opening 35 and the pot discharge line 32. The plate 31 can be moved back and forth between a park position (FIG. 14, FIG. 16, FIG. 18, FIG. 22) and a buffer storage device position (FIG. 15, FIG. 17, FIG. 19). When the cartridge 20 is inserted, then the plate 31 is located in the park position, and the cartridge 20 is in a respective fluid connection with the feed line 6 and with the discharge line 8 or only with the discharge line 8 (FIG. 22). The plate 31 and the sealing ring 40 prevent gas from the feed line 6 from flowing past the cartridge 20 into the discharge line 8. When the cartridge 20 is removed, then the plate 31 is in the buffer storage device position, and the buffer storage device cavity 36 is located in a respective fluid connection with the feed line 6 and with the discharge line 8. The sealing ring 40 prevents or at least reduces the risk that gas escapes upwards from the buffer storage device cavity 36 and reaches the surrounding area.

An embodiment of how the plate 31 is moved is described below. This embodiment leads to an especially simple mechanical embodiment. A plurality of spring elements 33 are supported at the bottom 44 of the pot 13 and aim to press the plate 31 against gravity upwards, i.e., away from the bottom 44 of the pot 13 and into the buffer storage device position and to hold same in this buffer storage device position. When the cartridge 20 is inserted into the pot 13, then the plate 31 is pressed against the spring action of the spring elements 33 downwards into the park position. This effect is brought about by the weight of the cartridge 20—or by a user pressing the cartridge 20 downwards in the pot 13. When the cartridge 20 is removed again, then the spring elements 33 press the plate 31 upwards into the buffer storage device position until the plate 31 reaches the lower closure of the pot gas lines 16 and 32. In conjunction with the optional sealing ring 40, the plate 31 largely prevents excess gas from being released from the pot 13 upwards into the surrounding area. It is possible that a latching unit, not shown, holds the plate 31 in a position.

Figure 18:
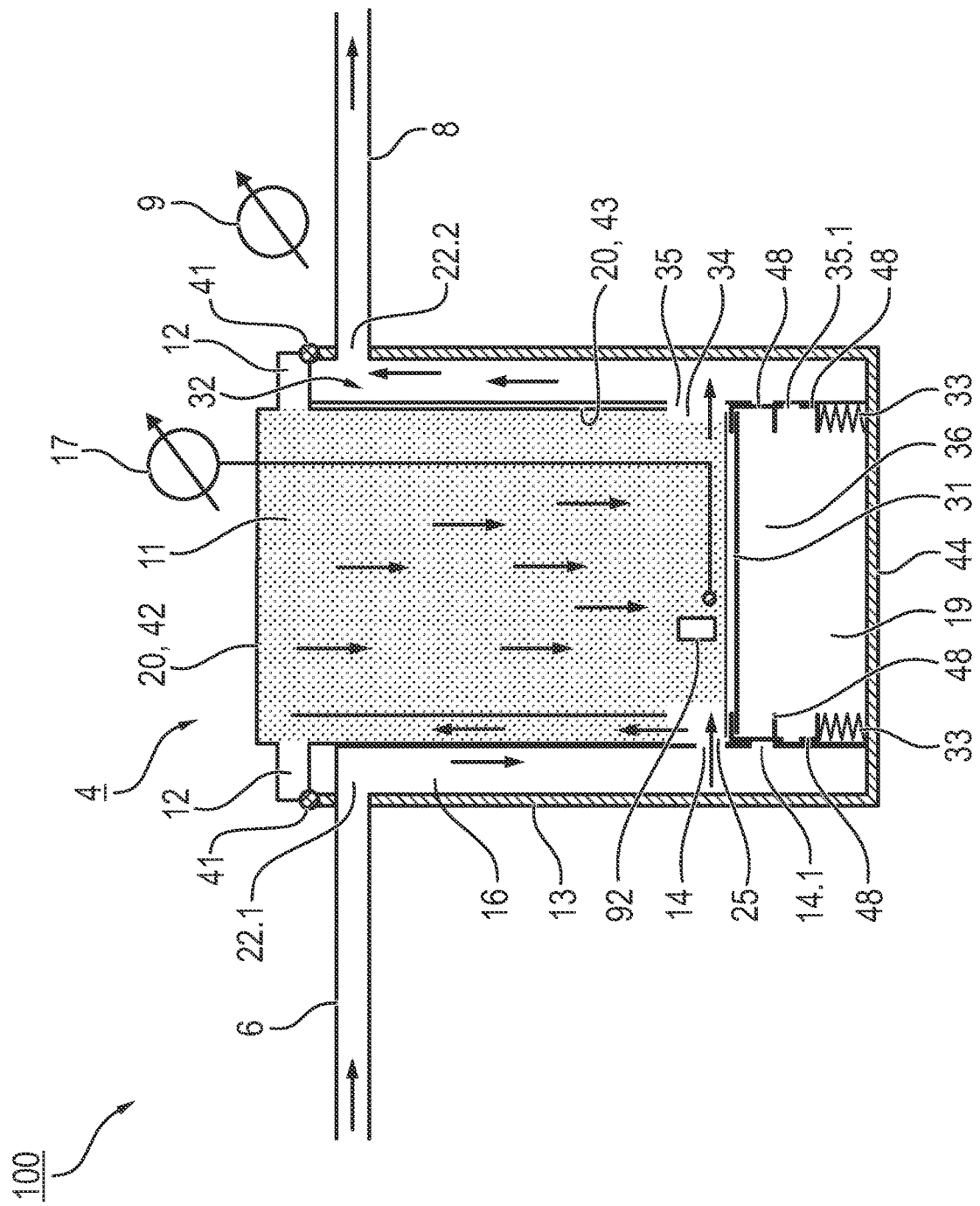
FIG. 18 is a schematic view showing another variant of the embodiment from FIG. 14 and FIG. 15, wherein an inserted filter holds a movable slide in a park position.
Figure 19:
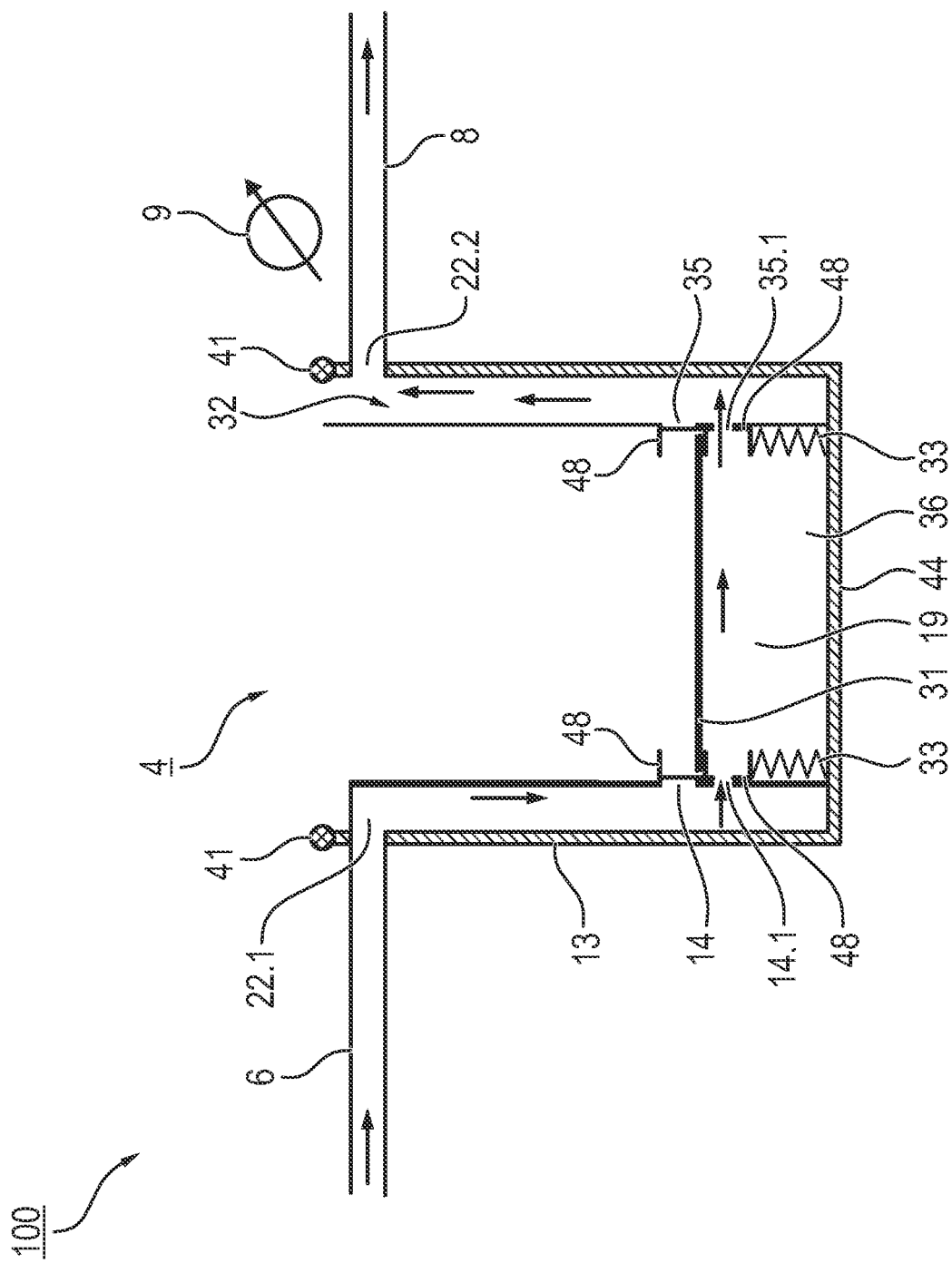
FIG. 19 is a schematic view showing the embodiment from FIG. 18, wherein the filter has been removed and the slide is in a buffer storage device position.

FIG. 18 and FIG. 19 show another embodiment of the mechanical solution of the buffer storage device 19. Identical reference numbers have the same meaning as in FIG. 14 through FIG. 17. In turn, a plate 31 divides the interior of the pot 13 into a filter cavity 37 and into a buffer storage device cavity 36. As a result, the plate 31 separates a buffer storage device 19 from an inserted filter 11, 20. This buffer storage device 19 is, in turn, located between the plate 31 and the bottom 44 of the pot 13. In the embodiment according to FIG. 18 and FIG. 19, no opening 21 is formed in the wall of the pot 13. This embodiment is preferably used in an application without a suction pump 10.

A slide 48 in the interior of the pot 13 is permanently connected to the plate 31 and together with the plate 31 can be moved up and down between a buffer storage device position (FIG. 19, no filter 11, 20 inserted) and a park position (FIG. 18, filter 11, 20 inserted to the filter cavity 37 in the pot 13). The spring elements 33 aim to move the plate together with the slide 48 upwards into the buffer storage device position. The weight of the inserted filter 11, and optionally a user inserting the filter 11, 20 press the plate 31 and thus the slide 48 against the spring action of the spring elements 33 downwards into the park position. The plate 31 optionally snaps into in the park position.

At the lower end of the pot feed line 16 are arranged two outlet openings 14 and 14.1, which are called filter outlet opening and buffer storage device outlet opening below. The filter outlet opening 14 is located above the buffer storage device outlet opening 14.1. In case a filter 11, 20 is inserted correctly (FIG. 18), then, as in the previous embodiments, the filter outlet opening 14 overlaps the inlet opening 25 of the cartridge 20. The filter outlet opening 14 of the pot feed line 16 thus leads into the inlet opening 25 of the filter 11, 20. The downwards pressed slide 48 releases the filter outlet opening 14 and blocks the buffer storage device outlet opening 14.1. In case no filter 11, 20 is inserted and the slide 48 is in the buffer storage device position (FIG. 19), then the pot feed line 16 is in a fluid connection with the buffer storage device 19 through the buffer storage device outlet opening 14.1. The buffer storage device outlet opening 14.1 thus leads into the buffer storage device 19. The upwards pressed slide 48 releases the buffer storage device outlet opening 14.1 and blocks the filter outlet opening 14.

The same applies to the pot discharge line 32. A buffer storage device inlet opening 35.1 is formed below the filter inlet opening 35 at the lower end of the pot discharge line 32. In case a filter 11, 20 is inserted and the slide 48 is in the park position, then the filter inlet opening 35 overlaps the outlet opening 34 of the cartridge 20. The outlet opening 34 of the filter 11, 20 thus leads into the filter inlet opening 35 of the pot discharge line 32. The downwards pressed slide 48 releases the filter inlet opening 35 and blocks the buffer storage device inlet opening 35.1. In case no filter 11, 20 is inserted, then the pot discharge line 32 is in fluid connection with the buffer storage device 19 through the buffer storage device inlet opening 35.1. The buffer storage device 19 thus leads into the buffer storage device inlet opening 35.1 of the pot discharge line 32. The upwards pressed slide 48 releases the buffer storage device inlet opening 35.1 and blocks the filter inlet opening 35.

In case the plate 31 and the slide 48 are in the park position (FIG. 18), then gas flows through the pot feed line 16 and the openings 14 and 25 into the filter element 11 and subsequently through the openings 34 and 35 into the pot discharge line 32. The slide 48 prevents gas from reaching the buffer storage device 19. In case the plate 31 and the slide 48 are in the buffer storage device position (FIG. 19), then gas flows through the pot feed line 16 and the opening 14.1 into the buffer storage device 19 and through the opening 35.1 into the pot discharge line 32. The plate 31 largely prevents gas from being released upwards out of the buffer storage device 19.

FIG. 22 and FIG. 23 show an embodiment, which combines the spring-mounted plate 31 from FIG. 14 through FIG. 17 with the buffer storage device 23 from FIG. 20 and FIG. 21 and likewise comprises the pot feed line 16. In the situation shown in FIG. 22, the cartridge 20 with the filter element 11 is inserted, and the cartridge 20 is removed in the situation shown in FIG. 23. A sealing element or a sealing ring 40 is fastened to the plate 31. In addition, an additional circular sealing ring 40 is fastened to the pot 13 on the inside. The pot feed line 16 as well as a bracket 45 hold this sealing ring 40 in a suitable position.

The plate 31 is located in the park position in FIG. 22 and in the buffer storage device position in FIG. 23. A circular web at the bottom of the plate 31 contacts the bottom 44 when the plate 31 is in the park position and prevents gas from flowing through out of the feed line 6 under the plate 31 into the discharge line 8. As a result, gas is prevented from bypassing the anesthetic filter 11, 20. The gas flows, rather, through the opening 22.1 and is first carried into the intermediate space between the pot 13 and the cartridge 20 upwards through the pot feed line 16 up to the inlet opening 25, then flows through the filter 11, 20 and reaches the outlet opening 34. The gas flows through the opening 22.2 into the discharge line 8.

When the cartridge has been removed and the plate 31 is in the buffer storage device position (FIG. 23), then the sealing element 40 at the plate 31 and the sealing ring 40 on the inside of the pot 13 prevent the undesirable event that gas flows upwards from the buffer storage device cavity 36 past the plate 31 and escapes into the surrounding area. Rather, the plate 31 and the pot 13 largely separate the buffer storage device cavity 36 from the surrounding area.

In this variant as well, an opening 26 is formed in the bottom 44 of the pot 13, and the pot 13 is in fluid connection through this opening 26 with a rigid buffer storage device 23, which comprises a meandering tube. The inlet opening 25 of the cartridge 20 is arranged close to the cover 42 of the cartridge 20, and the outlet opening is arranged close to the bottom 39 of the cartridge 20. The sensor 15 and the measurement line 18 are arranged close to the cover 42 of the cartridge 20. When the cartridge 20 is inserted into the pot 13, the plate is pressed downwards against the force of the spring 33 and as a result diverts the gas into the cartridge 20. When the cartridge 20 is removed, then the springs 33 press the plate 31 upwards, without the plate 31 becoming jammed. When the cartridge 20 is inserted, then gas flows around the plate 31 into the buffer storage device cavity 36 and from there into the buffer storage device 23 and also back again, as a result of which the function of a buffer storage device is embodied.

FIG. 24 shows an embodiment, in which the rigid buffer storage device 23 is arranged downstream of the filter unit 4 and is in a fluid connection with the discharge line 8. The term "downstream" refers to the flow direction of the gas in front of the medical apparatus 1 towards the fluid taking up/receiving unit 7. The buffer storage device 23 may also be arranged upstream of the filter unit 4 and may be in a fluid connection with the feed line 6.

The embodiment according to FIG. 24 makes it possible to configure the filter unit 4 as smaller and/or to configure the filter 11, 20 as greater than in case of the embodiment according to FIG. 2 through FIG. 19 as well as FIG. 22 and FIG. 23, because a cavity, which functions as a buffer storage device, does not necessarily need to occur between the cartridge 20 and the pot 13. In addition, the vertical dimension is smaller compared with the embodiments described above. The discharge line 8 leads through the buffer storage device 23. The buffer storage device 23 is indirectly in fluid connection via the filter unit 4 with the feed line 6 as well. The volume flow sensor 9 and the suction pump 10 are preferably located downstream of the buffer storage device 23.

In the embodiment according to FIG. 24, the buffer storage device 23 is arranged downstream of the filter unit 4. In the variant shown in FIG. 13, the filter unit 4 is likewise arranged upstream or else downstream of the elastic buffer storage device 70. In this variant also, the optional volume flow sensor 9 and the suction pump 10 are preferably arranged downstream of the filter unit 4.

The embodiments described so far comprise a sensor 15 which measures an indicator of the quantity or concentration of the anesthetic in the cartridge 20. The event that the quantity of concentration is above a predefined anesthetic threshold indicates that the filter element 11 is no longer filtering enough anesthetic out of the gas flow flowing through. An alarm is outputted on the consumption indicator 17 as a response to the detection of this event. An alarm is then also preferably outputted when the pressure relief valve 50 has opened. A possible reason that the pressure relief valve 50 has opened is that the filter element 11 has become clogged, for example, because the filter element 11 is swollen because of moisture.

The consumption indicator or a consumption indicator 17 may be arranged at the filter unit 4 or at the pot 13. It is also possible that a consumption indicator or an alarm generation unit is arranged at a distance in space, for example, in a center. An alarm is indicated in the center when the sensor 15 has measured a high concentration of anesthetic or when the pressure relief valve 50 has opened and it is therefore necessary to check the filter 11, 20 and to replace it as needed.

An alternative embodiments avoids the need to provide a sensor 15 for the quantity or concentration of anesthetic in the interior of the pot 13. Rather, the quantity of anesthetic which flows through the feed line 6 to the anesthetic filter 11, 20 is determined approximately. According to one possible embodiment, the respective current volume flow into the feed line, i.e., the volume of gas per time unit, which the anesthesia apparatus 1 discharges into the feed line 6, is measured at a plurality of consecutive scanning times. Or the current volume flow is determined in a different manner. In addition, it is measured approximately or determined in a different manner what concentration the anesthetic currently has in this gas stream. The volume flow of anesthetic, which flows through the feed line 6 in the filter unit 4 at a defined scanning time and is ideally entirely taken up/received by the filter element 11, is calculated from these two values. Numerical integration is then performed via these values for the anesthetic volume flow. This procedure yields an approximate value for the quantity of anesthetic, which the filter element 11 has taken up/received so far. The approximate value calculated in this way may be greater than the quantity actually taken up/received, especially when the pressure relief valve 50 opens from time to time and when at least one leak occurs between the anesthesia apparatus 1 and the filter 11, 20.

In an alternative embodiment, an indicator of the quantity of the liquid anesthetic in the anesthetic tank 49 is measured repeatedly, for example, by means of a floater in the tank 49. This quantity decreases over time, because anesthetic from the tank 49 is added to the carrier gas. Some of the anesthetic, which leaves the tank 49, is added to the carrier gas, for example, by vaporizing, and reaches the feed line 6. The quantity of anesthetic, which has left the tank 49 so far, is an upper threshold for the quantity of anesthetic, which the filter element 11 has taken up/received so far.

The two embodiments just described may be combined, especially in order to reduce the inaccuracy.

The value for the taken up/received quantity is preferably set to zero when a new filter 11, 20 is inserted into the pot 13. For example, the filter 11, 20 comprises a data storage medium 92, for example, an RFID chip, the data storage medium 92 preferably being arranged at an outer wall of the cartridge 20. The taking up/receiving system 100 comprises a reader and writer for such a data storage medium, for example, an RFID reader and writer. In an alternative embodiment, a user inputs the information by means of a stationary or portable computer or by means of another input unit that a new filter 11, 20 has been inserted into the pot 13.

In one embodiment, the predefined concentration, which is set at the anesthetic vaporizer 2, is determined, cf. FIG. 1. In another embodiment, the actual concentration of anesthetic is measured at at least one measuring point in the anesthesia apparatus 1.

As a rule, the anesthetic vaporizer 2 comprises a storage tank 49 for liquid anesthetic. The fill level sensor in one embodiment measures an indicator of the quantity of the liquid anesthetic in this tank, for example, by means of a floater. What quantity of liquid anesthetic has been vaporized so far is derived from the measured values of this fill level sensor. This quantity vaporized so far is an upper threshold for the quantity of anesthetic which the filter element 11 has taken up/received so far.

In one embodiment, the anesthesia apparatus 1 discharges anesthetic into the feed line 6 only in a phase of exhalation. Hence, only values at such scanning times, which are in a phase of exhalation, are taken into consideration in the calculation of the quantity of anesthetic. Such a procedure may be provided as described, for example, in DE 10 2006 027 052 B3 (corresponding to U.S. Pat. No. 9,770,569 (B2), the entire contents of which are incorporated herein by reference). In another embodiment, the feed of breathing air or of another fresh gas is so great that the anesthesia apparatus 1 also discharges anesthetic in a phase of inhalation.

In one embodiment, the information about the maximum quantity of anesthetic the filter element 11 can take up/receive is stored in a memory, for example, in the just described memory 92 at the outer wall of the cartridge 20. This quantity is predefined. A comparator repeatedly compares the quantity of anesthetic, which this filter element 11 has taken up/received so far and which is calculated approximately, as was just described, with the predefined and stored maximum quantity which the filter element 11 can take up/receive. As soon as the actually taken up/received quantity differs from the predefined and stored maximum quantity by less than a predefined absolute or percent threshold, a warning is outputted in a form perceptible by a person, for example, on an output unit located at a distance in space, wherein the output unit is especially positioned in a center.

Figure 25:
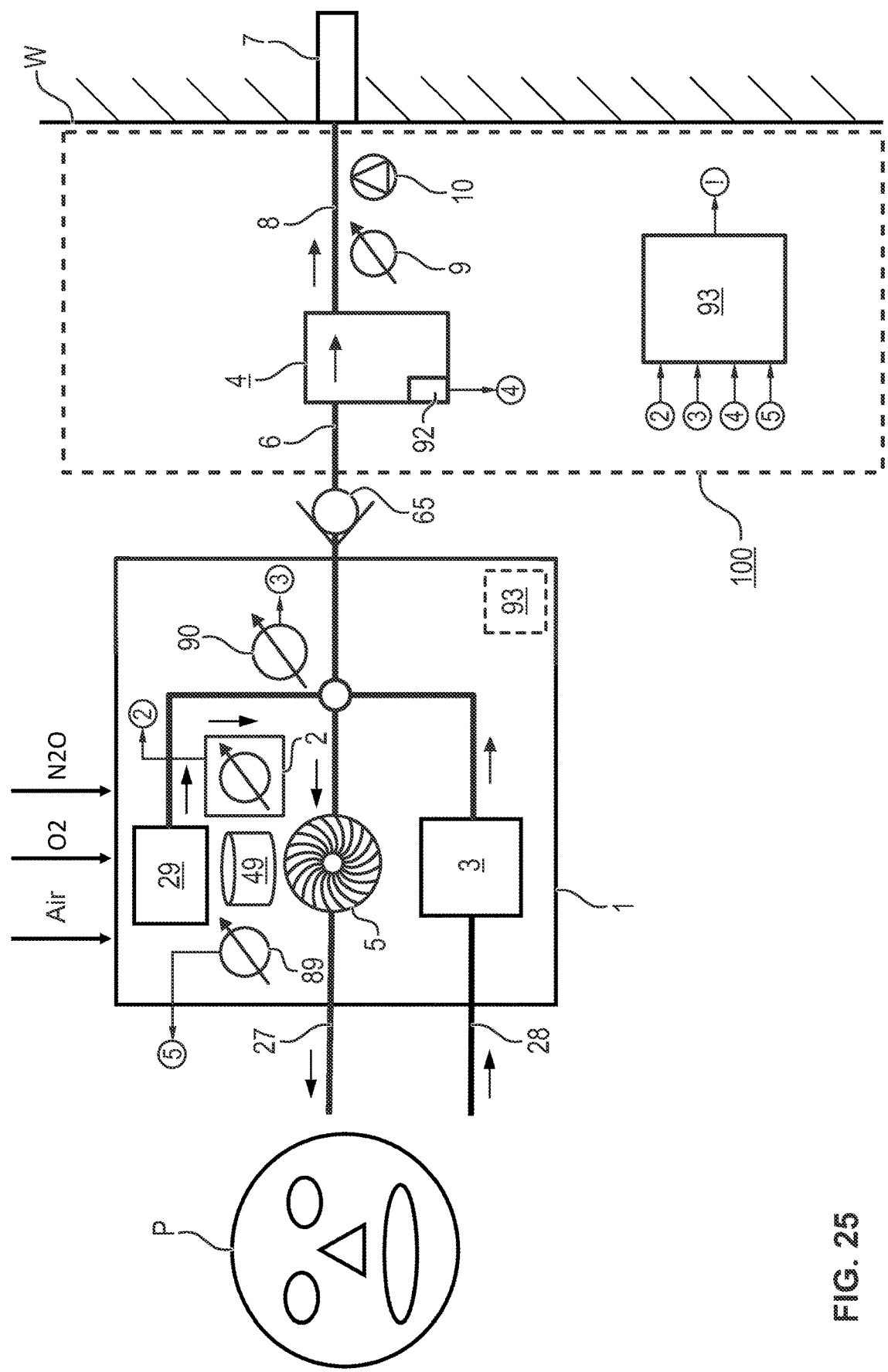
FIG. 25 is a schematic view showing a variant of the device according to FIG. 1, which additionally comprises an anesthetic quantity determination device and a memory at the filter unit.

FIG. 25 illustrates an exemplary embodiment, wherein the corresponding components are added compared to the system from FIG. 1. Identical components have the same reference numbers as in FIG. 1. Additionally shown are:

a fill level sensor 89, which measures an indicator of the current fill level in the anesthetic tank 49 and comprises, for example, a floater on the surface of the anesthetic in the tank 49 and/or a scale, a volume flow sensor 90, which belongs to the anesthesia apparatus 1 and measures the volume flow, i.e., the volume per time unit, of gas, which the anesthesia apparatus 1 discharges into the feed line 6, a concentration sensor 91, which measures the concentration of anesthetic, which is set at the anesthetic vaporizer 2 and/or which the anesthetic vaporizer 2 actually achieves, the memory 92 of a filter 11, 20 of the filter unit 4, and a data-processing anesthetic quantity determination device 93.

A nonreturn valve 65, which is arranged between the anesthesia apparatus 1 and the taking up/receiving system 100, i.e., upstream of the feed line 6, is shown as an example in FIG. 25. The nonreturn valve 65 lets gas pass from the anesthesia apparatus 1, but prevents gas from being able to flow out of the feed line 6 into the anesthesia apparatus 1. In particular, no gas can flow out of the fluid taking up/receiving unit 7 into the anesthesia apparatus 1.

In the example shown in FIG. 25, information about the maximum quantity of anesthetic, which the filter element 11 can take up/receive, is stored in the memory 92. This maximum quantity may be indicated as the volume of anesthetic in the gas or liquid form or even as the weight thereof.

The anesthetic quantity determination device 93 receives measured values from the sensors 89, 90 and 91 and information about the maximum quantity from the memory 92. The anesthetic quantity determination device 93 calculates, as just described, an indicator of the quantity of anesthetic, which the filter element 11 has taken up/received so far, compares the quantity taken up/received so far with the maximum quantity and outputs a warning when the quantity taken up/received so far is close to the maximum quantity of the filter element 11.

In one embodiment, the anesthetic quantity determination device 93 is embodied in the anesthesia apparatus 1, which is suggested in FIG. 25. It is also possible that the anesthetic quantity determination device 93 is implemented on a separate computer, for example, on a smartphone.

One embodiment takes into consideration the possibility that the same filter element 11 can take up/receive different anesthetics one after the other or even simultaneously. It is possible, for example, that the taking up/receiving system 100 is used in various operations, in which different anesthetics are used, one after the other. It is also possible that the taking up/receiving system 100 is used in an operation, in which a mixture of a plurality of anesthetics is used.

According to this embodiment, the information what maximum quantity of a reference anesthetic the filter element 11 can take up/receive is stored in the memory 92. In addition, a respective conversion factor is stored for each anesthetic, in which the filter element 11 can be used, especially in the memory 92 or in a different memory. The filter element 11 is capable of taking up/receiving a maximum quantity of an anesthetic, which is equal to the product of the conversion factor and the maximum quantity of the reference anesthetic.

During the use, the anesthetic quantity determination device 93 receives measured values from the sensors 90 and 91 as well as information about the maximum quantity of the reference anesthetic from the memory 92, the conversion factors, as well as the information, in what period which respective anesthetic is used. The anesthetic quantity determination device 93 is, for example, in a data connection with the anesthesia apparatus 1, and the anesthesia apparatus 1 transmits to the anesthetic quantity determination device 93 the information about which anesthetic is currently being used and hence is flowing or could flow through the filter element 11.

The anesthetic quantity determination device 93 calculates, as just described for each anesthetic used, what quantity of this anesthetic the filter element 11 has taken up/received so far. On the basis of the reciprocal values of the conversion factors, the anesthetic quantity determination device 93 converts for each possible anesthetic the quantity of this anesthetic taken up/received so far into the corresponding quantity of the reference anesthetic. The anesthetic quantity determination device 93 adds up the corresponding quantities of the reference anesthetic and thereby calculates an equivalent taken up/received total quantity of the reference anesthetic. The filter element 11 is spent and has to be replaced when this sum of the equivalent quantities reaches or exceeds the maximum quantity of the reference anesthetic.

What quantity of an anesthetic a filter element 11 is capable of taking up/receiving depends in many cases not only on the kind of the anesthetic, but also additionally on use conditions. In one embodiment, the just described conversion factor for an anesthetic additionally depends on at least one of the following measurable use conditions:
the temperature, the pressure and/or the humidity of the gas, which is flowing through the filter element 1,
the concentration of the anesthetic in this gas,
the temperature, the pressure and/or the humidity of the surrounding air.

In one embodiment, the warning that the filter element 11 is almost or entirely spent is outputted in the form of a traffic light. Green means that the actually taken up/received quantity is below the maximum quantity by more than a predefined distance. Yellow means that the actually taken up/received quantity is still below the maximum quantity, but by less than the predefined distance. Red means that the actually taken up/received quantity has reached or exceeded the maximum quantity. In another embodiment, the quantity of an anesthetic taken up/received so far is outputted as the percentage of the maximum possible quantity of this anesthetic, for example, separately for each anesthetic.

The just described embodiment uses information about the maximum possible quantity of anesthetic which the filter element 11 currently being used can take up/receive. In one embodiment, this information about the maximum quantity is stored in the memory 92 of the filter 11, 20 being used. A reader of the taking up/receiving system 100 is capable of reading out this memory. A reader inputs what type of filter 11, 20 is being used in another embodiment. The respective maximum quantity of anesthetic that a filter unit of this type can take up/receive is stored in a memory for each possible type of a filter unit 4.

The reader and writer stores the information about what quantity of this anesthetic the filter element 11 has taken up/received so far in the memory 92 for each anesthetic being used in one embodiment. This information is preferably updated continuously. This information can be used later to process the filter element 11 again and/or to obtain taken up/received anesthetic from the filter element 11. Process steps in the processing of a filter element 11 may depend especially on the type and quantity of the anesthetic taken up/received.

Optionally, information about the quantity of the reference anesthetic taken up/received so far is additionally stored in the memory 92 or in a central memory. This information is preferably updated continuously, so that a time curve of the spent quantity of reference anesthetic is generated. This time curve makes it possible to predict approximately a remaining use duration of the filter element 11.

In one embodiment, the quantity taken up/received so far is stored in the memory 92 or in a central memory for each anesthetic. This storage is preferably carried out anew after each operation or other use of the filter 11, 20. Before or at the beginning of an operation, the quantities taken up/received so far are read out or determined in a different way. The difference between the taken up/received quantities after and before the operation yield an indicator of the consumption during the operation.

Figure 26:
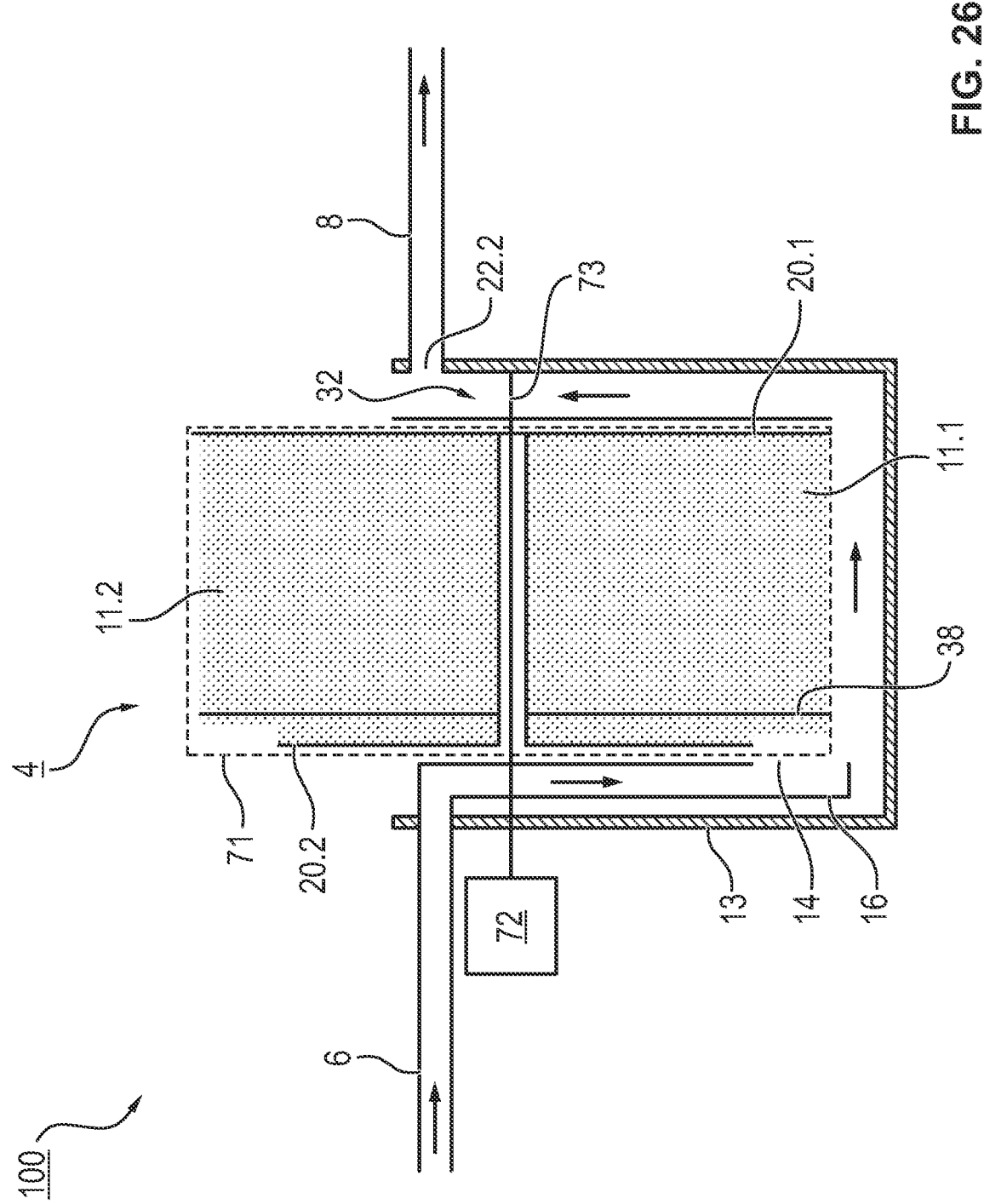
FIG. 26 is a schematic view showing a filter unit with two filters, which are inserted in a turret holder.

In all embodiments described so far, the filter unit 4 comprises a single filter element 11, optionally in a cartridge 20. FIG. 26 shows an exemplary embodiment, in which the filter unit 4 has two filter elements 11.1 and 11.2 in a respective cartridge 20.1, 20.2. Identical reference numbers have the same meanings as in the previous figures.

The two filters 11.1, 20.1 and 11.2, 20.2 are inserted into two corresponding mounts of a receiving unit 71, wherein the receiving unit 71 has the form of a turret holder and is rotatable about a axis of rotation 73. The horizontal axis of rotation 73 is connected rotatably to the lateral wall of the pot 13 and lies in the drawing plane of FIG. 26. As a result, the filter 11.1, 20.1 or the filter 11.2, 20.2 can be selectively brought into a position between the outlet opening 14 at the lower end of the pot feed line 16 and at the lower end of the pot discharge line 32. As a result, the filter 11.1, 20.1 or the filter 11.2, 20.2 is selectively in a position, in which gas flows through the feed line 6, through this filter 11.1, 20.1 or 11.2, 20.2 and the discharge line 8. In the situation shown in FIG. 26, gas can flow through the filter 11.1, 20.1, while the filter 11.2, 20.2 is in a park position.

The receiving unit 71 preferably snaps in, when it is in a position, in relation to the pot 13, in which the inlet opening 25 of the filter 11.1, 20.1 or 11.2, 20.2 overlaps the outlet opening 14. As a result, the risk that gas flows past a filter element 11.1 or 11.2 is reduced.

It is possible that a user manually rotates the receiving unit 71 about the axis 73. An optional motor 72 is, in another embodiment, capable of rotating the receiving unit 71 in relation to the pot 13 about the axis 73. In one embodiment, the motor 72 can be actuated from outside or be activated by a user input, for example, by a pushbutton. The actuated or activated motor 72 rotates the receiving unit 71 by one position further. As a result, the filter 11.1, 20.1 or the filter 11.2, 20.2 can also be caused to be selectively in a position in which gas flows through it due to an actuation or activation from outside.

In one embodiment, a control device receives measured values from the sensor 15 described above in the pot 13 and is capable of actuating the motor 72. As soon as the sensor 15 has measured a high concentration of an anesthetic, the control device actuates the motor 72, and the motor 72 rotates the receiving unit 71 by one position further.

In one embodiment, the two filters 11.1, 20.1 and 11.2, 20.2 have a similar configuration and are capable of filtering the same anesthetic or the same anesthetics out of a gas flowing through. The receiving unit 71 is rotated manually or by the motor 72, when a filter is spent. The filter element 11.1 is, in another embodiment, capable of filtering out a first anesthetic, the filter element 11.2 is capable of filtering out a second anesthetic. Depending on which anesthetic is currently being filtered out of a gas stream, the filter 11.1, 20.1 or the filter 11.2, 20.2 is brought into a position, in which the inlet opening 25 overlaps the outlet opening 14.

Of course, it is possible that the receiving unit 71 comprises mounts for more than two filters. It is also possible that the receiving unit 71 cannot be rotated in relation to the pot 13, but can be moved or pivoted linearly.

In an alternative, the taking up/receiving system 100 comprises a switch, which is arranged between the feed line 6 and the pot 13. This switch sends gas, which is flowing through the feed line 6, selectively to the first filter 11.1, 20.1 or to the second filter 11.2, 20.2 or to an optional third filter, not shown.

In the embodiments described so far, the taking up/receiving system 100 according to the present invention is connected to a single medical apparatus 1. FIG. 27 shows two alternative embodiments, in which the same taking up/receiving system 100 according to the present invention is connected or can be connected to two medical apparatuses 1 and 1.1. Identical reference numbers have the same meanings as in the embodiment described above.

The taking up/receiving system 100 can be selectively connected to the medical apparatus 1 or the medical apparatus 1.1 in the embodiment according to FIG. 27a. A line 6.1 leads from the medical apparatus 1 to a switch 96, which belongs to the taking up/receiving system 100. A line 6.2 leads from the medical apparatus 1.1 likewise to the switch 96. In the position shown in FIG. 27a, the switch 96 establishes a fluid connection between the line 6.1 and the feed line 6. The switch 96 can be adjusted into a position, in which it establishes a fluid connection between the line 6.2 of the feed line 6.

In the embodiment according to FIG. 27b, the taking up/receiving system 100 comprises a Y-piece 97 instead of a switch 96. The two legs of this Y-piece 97 are connected to the two lines 6.1 and 6.2. The bar of the Y-piece is connected to the feed line 6. Thanks to the Y-piece 97, both medical apparatuses 1 and 1.1 are simultaneously connected to the taking up/receiving system according to the present invention.

In the embodiments described so far, the taking up/receiving system 100 is connected to a stationary fluid taking up/receiving unit 7 in a wall W. FIG. 28 shows two alternative embodiments, in which the taking up/receiving system 100 is selectively or even simultaneously connected or can be connected to the stationary fluid taking up/receiving unit 7 or to an additional stationary fluid taking up/receiving unit 7.1.

In the embodiment according to FIG. 28a, a switch 98 connects the discharge line 8 selectively to a line 8.1 or to a line 8.2. The line 8.1 leads to the fluid taking up/receiving unit 7, the line 8.2 leads to the additional fluid taking up/receiving unit 7.1. In the position shown in FIG. 28a, the filter unit 4 is connected to the fluid taking up/receiving unit 7 via the lines 8 and 8.1.

In the embodiment according to FIG. 28b, the two legs of a Y-piece 99 are connected to the two lines 8.1 and 8.2. The bar of the Y-piece 99 is connected to the discharge line 8. As a result, the filter unit 4 is simultaneously in a fluid connection with the two fluid taking up/receiving units 7 and 71. Thanks to this embodiment, gas is taken up/received even if a stationary fluid taking up/receiving unit 7, 7.1 is defective or cannot alone take up/receive the entire quantity of the gas being discharged.

While specific embodiments of the invention have been shown and described in detail to illustrate the application of the principles of the invention, it will be understood that the invention may be embodied otherwise without departing from such principles.

LIST OF REFERENCE NUMBERS

1 Anesthesia apparatus, comprises the anesthetic vaporizer 2, the mixer 29, the lime filter 3 and the ventilator unit 5
2 Anesthetic vaporizer in the anesthesia apparatus 1, comprises the anesthetic tank 49
3 Lime filter, which filters CO2 out of the exhaled air
4 Filter unit, which filters anesthetic out of the gas discharged by the anesthesia apparatus 1, comprises the activated carbon filter 11 in the cartridge 20, the cartridge 20 and the pot 13, connected to the feed line 6 and the discharge line 8
5 Ventilator unit of the anesthesia apparatus 1, which moves gas in the ventilation circuit
6 Feed line, leads from the anesthesia apparatus 1 to the filter unit 4
6.1, 6.2 Lines, which connect the switch 96 or the Y-piece 97 to the medical apparatuses 1 and 1.1
7 Stationary gas taking up/receiving unit of the hospital infrastructure, accommodated by the wall W, connected to the filter unit 4 via the discharge line 8
7.1 Additional stationary gas taking up/receiving unit, accommodated by the wall W
8 Discharge line, leads from the filter unit 4 to the gas taking up/receiving unit 7
8.1, 8.2 Lines, which connect the switch 98 or the Y-piece 99 to the gas taking up/receiving units 7 and 7.1
9 Volume flow sensor in the discharge line 8
10 Suction pump at the discharge line 8 or in the fluid taking up/receiving unit 7, is in a fluid connection with the discharge line 8

11 Cylindrical activated carbon filter of the filter unit 4, functions as a filter element, is enclosed by the cartridge 20
11.1, 11.2 Cylindrical filter elements in the receiving unit 71
12 Circumferential projection of the cartridge 20, is supported at the upper edge of the pot 13
13 Pot, into which the feed line 6 leads and out of which the discharge line 8 leads, functions as a filter mount
14 Outlet opening of the pot feed line 16, arranged at the lower end of the pot feed line 16, overlaps the inlet opening 25 when the cartridge 20 has been inserted
14.1 Buffer storage device outlet opening of the pot feed line 16, arranged below the outlet opening 14, is in a fluid connection with the buffer storage device when no filter 11, 20 is inserted
15 Sensor, which measures the state of the activated carbon filter 11
16 Pot feed line in the interior of the pot 13, forms a fluid-tight continuation of the feed line 6, carries gas from the feed line 6 to the bottom 44 of the pot 13, ends in the outlet opening 14
17 Consumption indicator for the activated carbon filter 11
18 Signal line from the sensor 15 to the consumption indicator 17
19 Buffer storage device in the form of an intermediate space between the pot 13 and the cartridge 20
20 Cylindrical cartridge, encloses the activated carbon filter 11, comprises the circumferential projection 12, carries the memory 92
20.1, 20.2 Cylindrical cartridge for the filter element 11.1, 11.2
21 Openings in the pot 13, connected to the surrounding area
22.1 Opening in the pot 13, in which the feed line 6 ends
22.2 Opening in the pot 13, in which the discharge line 8 begins
23 Buffer storage device in the form of a meandering tube, has the opening 24
24 Opening of the buffer storage device 23, establishes a connection with the surrounding area
25 Inlet opening close to the bottom 39 or to the cover 42 of the cartridge 20, overlaps the outlet opening 14 when the filter 11, 20 is inserted
26 Opening of the buffer storage device 23, which is in connection with the inlet opening 25
27 Inhalation gas line, to supply the patient P with breathing air
28 Exhalation gas line, to suction breathing air exhaled by the patient P
29 Mixer of the anesthesia apparatus 1, generates the carrier gas for the anesthetic
30 Inlet opening in the cover 42 of the cartridge 20
31 Spring-mounted plate close to the bottom 44 of the pot 13, divides the pot into a filter cavity 37 and a buffer storage device cavity 36
32 Pot discharge line in the interior of the pot 13, carries gas from the bottom 44 of the pot 13 into the discharge line 8
33 Spring elements, which are supported at the bottom 44 of the pot 13 and aim to press the plate 31 upwards away from the bottom 44
34 Outlet opening close to the bottom 39 of the cartridge 20, overlaps the inlet opening 35 when the filter 11, 20 is inserted
35 Inlet opening of the pot discharge line 32, is in fluid connection with the outlet opening 34 when the filter 11, 20 is inserted
35.1 Buffer storage device inlet opening of the pot discharge line 32, is in fluid connection with the buffer storage device 19 when the filter 11, 20 has been removed
36 Buffer storage device cavity in a lower area of the pot 13, formed by the plate 31 and the wall and the bottom 44 of the pot 13, belongs to the buffer storage device, separated from the filter cavity 37 by the plate 31
37 Filter cavity in an upper area of the pot 13, is capable of accommodating the filter 11, 20, separated from the buffer storage device cavity 36 by the plate 31
38 Vertical partition in the interior of the filter 11, 20, separates the ascent area Au from the descent area Ab
39 Bottom of the cartridge 20
40 Lower sealing elements, prevent gas from flowing from the pot feed line 16 around the cartridge 20 to the pot discharge line 32
41 Upper sealing elements, between the upper edge of the pot 13 and the circumferential edge 12 of the cartridge 20
42 Cover of the cartridge 20
43 Lateral surface of the cartridge 20
44 Bottom of the pot 13
45 Holding element for a lower sealing element 40
47 Filter sensor in the pot 13, which determines whether or not a filter 11, 20 is inserted
48 Slide in the interior of the pot 13, connected to the plate 31
49 Anesthetic tank of the anesthetic vaporizer 2
50 Pressure relief valve in the feed line 6
50.1 Embodiment of the pressure relief valve 50, comprises the valve plate 51 and the valve crater 52
50.2 Embodiment of the pressure relief valve 50, comprises the valve plate 51, the valve crater 52 and the compression spring 55
50.3 Embodiment of the pressure relief valve 50, comprises the valve plate 51 and the valve ball 56
50.4 Embodiment of the pressure relief valve 50, comprises the valve crater 52 and the valve flap 57
50.5 Embodiment of the pressure relief valve 50, comprises the U-shaped tube 58 with the liquid 59
50.6 Embodiment of the pressure relief valve 50, comprises the pressure sensor 60 and the actuatable on-off valve 61
50.7 Embodiment of the pressure relief valve 50, comprises the valve crater 52 and the duck-bill-shaped area 62
51 Valve plate of the pressure relief valve 50, is located on the valve crater 52
52 Valve crater of the pressure relief valve 50
53 Partition in the pot 13 between the filter unit 4 and the buffer storage device 19
54 Space between the filter unit 4 and the partition 53
55 Compression spring, which aims to press the valve plate 51 upwards
56 Valve ball, is located on the valve crater 52
57 Valve flap, connected rotatably to the valve crater 52
58 U-shaped tube, in which the liquid 59 is located
59 Liquid in the tube 58
60 Pressure sensor in the feed line to the actuatable on-off valve 61
61 Actuatable on-off valve
62 Duck-bill-shaped area, is located on the valve crater 72

64 Hose, which connects the pressure relief valve 50 to the discharge line 8

65 Nonreturn valve in the discharge line 8, prevents gas from flowing from the fluid taking up/receiving unit 7 through the discharge line 8 back to the anesthesia apparatus 1

70 Elastic buffer storage device at the feed line 6

71 Receiving unit for the two filters 11.1, 20.1 and 11.2, 20.2, is configured as turret holder and is rotatable about the axis 73

72 Motor, which is capable of rotating the turret holder 71 about the axis 73

73 Axis of rotation of the turret holder 71, connected rotatably to the pot 13

80 Vacuum valve at the pot 13

89 Fill level sensor, measures an indicator of the current fill level in the anesthetic tank 49

90 Volume flow sensor of the anesthesia apparatus 1, measures the volume flow of gas, which the anesthesia apparatus 1 discharges into the feed line 6

91 Concentration sensor, measures the concentration of anesthetic, which is set at the anesthetic vaporizer 2 or which the anesthetic vaporizer 2 actually achieves 92 Memory of the filter 11, 20, on which information about the maximum quantity of anesthetic that the filter element 11 can take up/receive is stored, is an RFID chip or a barcode at the cartridge 20 in one embodiment 93 Anesthetic quantity determination unit, receives measured values from the volume flow sensor 90, from the concentration sensor 91 and the information about the maximum quantity from the memory 92, determines the quantity of anesthetic, which the filter element 11 has taken up/received so far, and compares the quantity taken up/received so far with the maximum quantity 96 Switch, which selectively connects the feed line 6 to the line 6.1 or to the line 6.2

97 Y-piece, which connects the lines 6.1 and 6.2 to the feed line 6

98 Switch, which selectively connects the discharge line 8 to the line 8.1 or to the line 8.2

99 Y-piece, which connects the lines 8.1 and 8.2 to the discharge line 8

100 Taking up/receiving system, comprises the filter unit 8, the feed line 6, the discharge line 8, the volume flow sensor 9 and the suction pump 10

Ab Descent area in the filter 11, 20, in which the gas in the cartridge 20 drops downwards to the bottom 39

Au Ascent area in the filter 11, 20, in which the gas in the cartridge 20 rises upwards to the cover 42

P Patient, who is connected to the anesthesia apparatus 1 and inhales at least one anesthetic W Wall, which accommodates the stationary gas taking up/receiving unit 7

What is claimed is:

1. A taking up system for the taking up of gas from a medical apparatus, the taking up system comprising:
    a feed line configured to establish a fluid connection with the medical apparatus;
    a discharge line configured to establish a fluid connection with a fluid taking up unit or with a surrounding area;
    a filter unit comprising a filter, wherein the filter is configured to filter at least one predefined gas component out of a gas which is passed through the filter, wherein a respective fluid connection is established or is establishable between the feed line and the filter unit and between the discharge line and the filter unit; and
    a buffer storage device in a respective fluid connection with the feed line and/or in a respective fluid connection with the discharge line, the buffer storage device being configured to temporarily store gas from the feed line and/or from the discharge line and later to discharge same into the feed line and/or into the discharge line, wherein the taking up in system is configured to:
        guide gas out of the medical apparatus through the feed line to the filter unit;
        pass the gas through the filter unit and at least partially through the filter; and
        guide the gas through the discharge line to the fluid taking up unit or into the surrounding area;
    the filter unit further comprises a filter mount in a fluid connection with the feed line and in a fluid connection with the discharge line;
    the filter is insertable or inserted into the filter mount;
    the filter unit is configured such that with the filter inserted into the filter mount, an intermediate space is formed between an impermeable surface of the filter and at least one inner wall of the filter mount; and
    the intermediate space is in a fluid connection with the feed line and is in a fluid connection with the discharge line and forms the buffer storage device or forms a portion of the buffer storage device or forms all or a portion of a further buffer storage device.

2. The taking up system in accordance with claim 1, wherein the buffer storage device is additionally in a fluid connection with the surrounding area and is configured to discharge gas into the surrounding area.

3. The taking up system in accordance with claim 1, wherein:
    the buffer storage device comprises a housing which is in a fluid connection with the filter unit; and
    the housing of the buffer storage device provides an interior for the taking up of gas.

4. The taking up system in accordance with claim 1, wherein:
    the buffer storage device is arranged downstream of the filter unit with respect to a direction of flow from the feed line to the discharge line; or
    the filter unit is arranged downstream from the buffer storage device with respect to a direction of flow from the feed line to the discharge line.

5. The taking up system in accordance with claim 1, wherein:
    the filter unit further comprises a plate movably arranged and fluid-tightly dividing the interior of the filter mount into a filter cavity and a buffer storage device cavity;
    the filter is inserted or is insertable into the filter mount;
    the filter cavity is configured to accommodate the filter;
    the buffer storage device cavity forms the buffer storage device or a portion of the buffer storage device or forms a further buffer storage device; and
    the buffer storage device cavity is in a fluid connection with the feed line and is in a fluid connection with the discharge line at least when no filter is inserted into the filter mount.

6. The taking up system in accordance with claim 5, wherein:
    the plate is moveable back and forth between a buffer storage device position and a park position in relation to the filter mount;
    the plate is in the buffer storage device position when no filter is inserted into the filter mount; and
    the plate is in the park position when a filter is inserted into the filter mount;

the feed line has at least one outlet opening;
the discharge line has at least one inlet opening;
with the plate in the buffer storage device position the at least one outlet opening connects the feed line to the buffer storage device cavity;
with the plate in the buffer storage device position the at least one inlet opening connects the discharge line to the buffer storage device cavity;
with the plate in the park position the at least one outlet opening connects the feed line to the filter cavity; and
with the plate in the park position the at least one inlet opening connects the discharge line to the filter cavity.

7. The taking up system in accordance with claim 5, further comprising a slide arranged in the interior of the filter mount, wherein:
the slide is moveable back and forth between a buffer storage device position and a park position in relation to the filter mount;
the feed line has a filter outlet opening and a buffer storage device outlet opening;
the discharge line has a filter inlet opening and a buffer storage device inlet opening;
with the slide in the buffer storage device position, the buffer storage device outlet opening connects the feed line to the buffer storage device cavity, the buffer storage device inlet opening connects the discharge line to the buffer storage device cavity, and the slide blocks the filter outlet opening and the filter inlet opening; and
with the slide in the park position, the filter outlet opening connects the feed line to the filter cavity, the filter inlet opening connects the discharge line to the filter cavity, and the slide blocks the buffer storage device outlet opening and the buffer storage device inlet opening.

8. The taking up system in accordance with claim 7, wherein the slide is mechanically connected to the plate.

9. The taking up system in accordance with claim 1, wherein
the filter unit further comprises a filter sensor;
the filter unit encloses an interior and is in a fluid connection with the feed line and is in a fluid connection with the discharge line; and
the filter sensor is configured to determine whether or not the filter is inserted into the filter mount.

10. The taking up system in accordance with claim 1, wherein
the volume of the buffer storage device is variable;
a feed of gas into the buffer storage device expands the buffer storage device; and
the expanded buffer storage device is configured to contract and as a result to discharge received gas.

11. The taking up system in accordance with claim 1, further comprising an pressure relief valve configured to open if a difference between the pressure in the feed line and a pressure around the feed line is above a predefined overpressure threshold.

12. The taking up system in accordance with claim 11, further comprising a fluid guide unit, wherein:
the pressure relief valve is connected to the discharge line by the fluid guide unit;
a fluid connection is established between the pressure relief valve and the fluid guide unit with the pressure relief valve open.

13. The taking up system in accordance with claim 11, further comprising a concentration sensor configured to determine a concentration of a gas component at a measurement position downstream of the filter wherein the taking up system is configured to generate a message when the pressure relief valve is open or the concentration sensor has detected a concentration above a predefined concentration threshold.

14. The taking up system in accordance with claim 1, further comprising a vacuum valve, wherein the vacuum valve opens when a difference between the pressure in the feed line or in an interior of the filter unit and a surrounding pressure is below a predefined vacuum threshold.

15. The taking up system in accordance with claim 14, wherein:
at least one opening is formed in a wall of the filter unit;
with the vacuum valve open, the interior of the filter unit is in a fluid connection with a surrounding area through the at least one opening of the filter unit; and
with the vacuum valve closed, the fluid connection between the interior of the filter unit and the surrounding area is closed.

16. The taking up system in accordance with claim 1, wherein:
the filter is removeable from the filter mount.

17. The taking up system in accordance with claim 1, further comprising a switching device wherein:
the filter is a first filter and the filter unit further comprises another filter as a second filter;
the switching device is configured to selectively bring the first filter or the second filter into a fluid connection with the feed line and with the discharge line.

18. The taking up system in accordance with claim 17, wherein:
the first filter is configured to filter out the at least one predefined gas component; and
the second filter is configured to filter out another predefined gas component.

19. The taking up system in accordance with claim 1, wherein the filter unit is configured such that gas is carried through the filter in a path from the feed line to the discharge line and is configured to prevent the gas from bypassing the filter.

20. The taking up system in accordance with claim 1, wherein
a wall divides the filter into a first area and into a second area;
the first area is in a fluid connection with the feed line and the second area is in a fluid connection with the discharge line; and
the filter unit is configured such that gas flows from the feed line through the first area and then through the second area into the discharge line.

21. The taking up system in accordance with claim 1, further comprising a memory reader, wherein
the filter unit further comprises a memory;
the memory reader is configured to read out the memory;
the memory has stored thereon at least one of a unique filter unit identifier, use information indicating whether the filter unit is new or has already been used, gas component information indicating gas components the filter unit can be used with and/or cannot be used with, and time information about a time, at which the use of the filter unit for filtering was started.

22. The taking up system in accordance with claim 1, further comprising a component quantity determination unit configured to:
receive a signal for the time-variable volume flow of fluid through the feed line towards the filter unit and a signal for the time-variable concentration of the at least one predefined gas component or of at least one other gas component in the feed line or a signal for what quantity of the at least one predefined gas component is being fed into the feed line;

determine, as a function of these two signals, an approximate quantity of the at least one predefined gas component, which the filter unit has taken up so far, as a quantity taken up so far;

compare the quantity taken up so far with a predefined maximum quantity, which the filter unit is capable of taking up; and generate a message as a function of the result of the comparison.

23. The taking up system in accordance with claim 22, wherein:

the filter unit comprises a memory having stored thereon information about the maximum quantity of the at least one predefined gas component or of at least one other gas component, which the filter is capable of taking up; and the component quantity determination unit is configured to use the information stored in the memory as the predefined maximum quantity during the comparison.

24. The taking up system in accordance with claim 1, further comprising a vacuum generator, wherein the discharge line is in a fluid connection with the vacuum generator; and the vacuum generator is configured to generate a vacuum in the discharge line.

25. The taking up system in accordance with claim 1, wherein:

the filter has a lateral surface and an end face;

the intermediate space adjoins both the lateral surface and the end face of the filter.

26. The taking up system in accordance with claim 1, wherein:

the intermediate space is separate from the feed line and the discharge line.

27. A medical system comprising:

a medical apparatus; and a taking up system comprising:

a feed line configured to establish a fluid connection with the medical apparatus;

a discharge line configured to establish a fluid connection with a fluid taking up unit or with a surrounding area;

a filter unit comprising a filter, wherein the filter is configured to filter at least one predefined gas component out of a gas which is passed through the filter, wherein a respective fluid connection is established or is establishable between the feed line and the filter unit and between the discharge line and the filter unit; and a buffer storage device in a respective fluid connection with the feed line and/or in a respective fluid connection with the discharge line, the buffer storage device being configured to temporarily store gas from the feed line and/or from the discharge line and later to discharge same into the feed line and/or into the discharge line, wherein the taking up system is configured to:

guide gas out of the medical apparatus through the feed line to the filter unit;

pass the gas through the filter unit and at least partially through the filter; and guide the gas through the discharge line to the fluid taking up unit or into the surrounding area;

the filter unit further comprises a filter mount in a fluid connection with the feed line and in a fluid connection with the discharge line;

the filter is insertable or inserted into the filter mount;

the filter unit is configured such that with the filter inserted into the filter mount, an intermediate space is formed between an impermeable surface of the filter and at least one inner wall of the filter mount; and the intermediate space is in a fluid connection with the feed line and is in a fluid connection with the discharge line and forms the buffer storage device or forms a portion of the buffer storage device or forms all or a portion of a further buffer storage device.

28. The medical system in accordance with claim 27, further comprising an additional medical apparatus, wherein a fluid connection is selectively or simultaneously establishable one of between the medical apparatus and the feed line of the taking up system, or between the additional medical apparatus and the feed line of the taking up system.

29. The medical system in accordance with claim 27, wherein the taking up system is arranged in an interior of the medical apparatus.

30. The medical system according to claim 27, further comprising the fluid taking up unit, wherein the discharge line of the taking up system is in a fluid connection with the fluid taking up unit.

31. The medical system according to claim 30, wherein:

the medical system further comprises an additional fluid taking up unit; and a fluid connection is selectively or simultaneously establishable one of between the fluid taking up unit and the discharge line, or between the additional fluid taking up unit and the discharge line.

32. A process for the taking up of gas from a medical apparatus, the process comprising the steps of:

providing a taking up system, wherein the taking up system comprises: a feed line; a discharge line; a filter unit comprising a filter and a buffer storage device;

establishing a fluid connection between the medical apparatus and the feed line;

establishing a fluid connection between the discharge line and a fluid taking up unit or a surrounding area;

at least one of releasing, discharging and suctioning gas from the medical apparatus;

guiding, with the taking up system, the gas through the feed line, the filter unit and the discharge line to the fluid taking up unit or into the surrounding area, wherein all the gas or at least some of the gas is guided through the filter during the passing through the filter unit;

filtering, with the filter, at least one predefined gas component out of the gas, which is guided through the filter;

temporarily storing gas in the buffer storage device when more gas is released from the medical apparatus than is sent into the fluid taking up unit or into the surrounding area by sending gas from at least one of the feed line and the discharge line into the buffer storage device; and releasing the temporarily stored gas by sending the temporarily stored gas from the buffer storage device into at least one of one of the discharge line and the feed line;

the filter unit additionally comprises:

a filter mount enclosing an interior and being in a fluid connection with the feed line at least from time to time and being in a fluid connection with the discharge line at least from time to time;

the filter unit being configured such that with the filter inserted into the filter mount, an intermediate space is formed between an impermeable surface of the filter and at least one inner wall of the filter mount;

the intermediate space being in a fluid connection with the feed line and being in a fluid connection with the discharge line and forming the buffer storage device or forming a portion of the buffer storage device or forming all or a portion of a further buffer storage device.

33. The process in accordance with claim 32, wherein the filter unit additionally comprises:

a plate arranged to be movable and to fluid-tightly divide the interior of the filter mount into a filter cavity and a buffer storage device cavity, wherein:

the filter is inserted into the filter cavity;

the filter is removed from the filter mount at least one time; and the buffer storage device cavity is in a fluid connection with the feed line and in a fluid connection with the discharge line at least when the filter has been removed.

34. The process according to claim 32 wherein:

the medical apparatus is an anesthesia apparatus; and the at least one predefined gas component is at least one anesthetic from the anesthesia apparatus.

35. A taking up system for the taking up of gas from a medical apparatus, the taking up system comprising:

a feed line configured to establish a fluid connection with the medical apparatus;

a discharge line configured to establish a fluid connection with a fluid taking up unit or with a surrounding area;

a filter unit comprising a filter, wherein the filter is configured to filter at least one predefined gas component out of a gas which is passed through the filter, wherein a respective fluid connection is established or is establishable between the feed line and the filter unit and between the discharge line and the filter unit; and a buffer storage device in a respective fluid connection with the feed line and/or in a respective fluid connection with the discharge line, the buffer storage device being configured to temporarily store gas from the feed line and/or from the discharge line and later to discharge same into the feed line and/or into the discharge line, wherein the taking up system is configured to:

guide gas out of the medical apparatus through the feed line to the filter unit;

pass the gas through the filter unit and at least partially through the filter; and guide the gas through the discharge line to the fluid taking up unit or into the surrounding area;

the filter unit further comprises a filter mount enclosing an interior and being in a fluid connection with the feed line and in a fluid connection with the discharge line;

the filter unit further comprises a plate movably arranged and fluid-tightly dividing the interior of the filter mount into a filter cavity and a buffer storage device cavity;

the filter is inserted or is insertable into the filter mount;

the filter cavity is configured to accommodate the filter;

the buffer storage device cavity forms the buffer storage device or a portion of the buffer storage device or forms a further buffer storage device; and the buffer storage device cavity is in a fluid connection with the feed line and is in a fluid connection with the discharge line at least when no filter is inserted into the filter mount;

a slide arranged in the interior of the filter mount, wherein:

the slide is moveable back and forth between a buffer storage device position and a park position in relation to the filter mount;

the feed line has a filter outlet opening and a buffer storage device outlet opening;

the discharge line has a filter inlet opening and a buffer storage device inlet opening;

with the slide in the buffer storage device position, the buffer storage device outlet opening connects the feed line to the buffer storage device cavity, the buffer storage device inlet opening connects the discharge line to the buffer storage device cavity, and the slide blocks the filter outlet opening and the filter inlet opening; and with the slide in the park position, the filter outlet opening connects the feed line to the filter cavity, the filter inlet opening connects the discharge line to the filter cavity, and the slide blocks the buffer storage device outlet opening and the buffer storage device inlet opening.

* * * * *